US 9,447,038 B2

(12) United States Patent
Bata et al.

(10) Patent No.: US 9,447,038 B2
(45) Date of Patent: Sep. 20, 2016

(54) SUBSTITUTED B-AMINO ACID DERIVATIVES AS CXCR3 RECEPTOR ANTAGONISTS

(71) Applicant: SANOFI, Paris (FR)

(72) Inventors: Imre Bata, Budapest (HU); Veronika Bartane Bodor, Budapest (HU); Attila Vasas, Dunakeszi (HU); Peter Buzder-Lantos, Budapest (HU); Gyorgy Ferenczy, Budapest (HU); Zsuzsanna Tomoskozi, Budapest (HU); Gabor Szeleczky, Budapest (HU); Zsuzsanna Szamosvolgyi, Budapest (HU)

(73) Assignee: Sanofi, Paris (FR)

( * ) Notice: Subject to any disclaimer, the term of this patent is extended or adjusted under 35 U.S.C. 154(b) by 11 days.

(21) Appl. No.: 14/546,087

(22) Filed: Nov. 18, 2014

(65) Prior Publication Data

US 2015/0073004 A1  Mar. 12, 2015

Related U.S. Application Data

(63) Continuation of application No. PCT/EP2013/001418, filed on May 14, 2013.

(30) Foreign Application Priority Data

May 23, 2012  (EP) .................................... 12462009

(51) Int. Cl.
| C07D 409/12 | (2006.01) |
| C07D 405/12 | (2006.01) |
| C07D 207/404 | (2006.01) |
| C07D 233/72 | (2006.01) |
| C07D 407/12 | (2006.01) |
| C07D 239/54 | (2006.01) |
| C07D 233/74 | (2006.01) |

(52) U.S. Cl.
CPC ......... *C07D 207/404* (2013.01); *C07D 233/72* (2013.01); *C07D 233/74* (2013.01); *C07D 239/54* (2013.01); *C07D 405/12* (2013.01); *C07D 407/12* (2013.01); *C07D 409/12* (2013.01)

(58) Field of Classification Search
CPC .......................... C07D 409/12; C07D 405/12
See application file for complete search history.

(56) References Cited

FOREIGN PATENT DOCUMENTS

| WO | WO 03/087063 | 10/2003 |
| WO | WO 2006/004924 | 1/2006 |
| WO | WO 2007/002742 | 1/2007 |
| WO | WO 2009/094168 | 7/2009 |
| WO | WO 2009/105435 | 8/2009 |
| WO | WO 2011/084985 | 7/2011 |

OTHER PUBLICATIONS

International Search Report for WO2013/174485 dated Nov. 28, 2013.
Crosignani, et al., Discovery of a Novel Series of CXCR3 Antagonists, Bioorganic & Medicinal Chemistry Letters, vol. 20, (2010), 3614-3617.
Wijtmans, et al., Towards Small-Molecule CXCR3 Ligands With Clinical Potential, ChemMedChem, vol. 3, pp. 861-872, (2008).
Groom, et al., CXCR3 in T Cell Function, Experimental Cell Research, vol. 317, (2011), pp. 620-631.
Liu, et al., CXCL10/IP-10 in Infectious Diseases Pathogenesis and Potential Therapeutic Implications, Cytokine & Growth Factor Reviews, vol. 22, (2011), pp. 121-130.
Vandercappellen, et al., The Role of the CXC Chemokines Platelet Factor-4 (CXCL4/PF-4) and its Variant (CXCL4L1/PF-4var) in Inflammation, Angiogenesis and Cancer, Cytokine & Growth Factor Reviews, vol. 22, (2011), pp. 1-18.
Romagnani, et al., CXC Chemokines: The Regulatory Link Between Inflammation and Angiogenesis, TRENDS in Immunology, vol. 25, No. 4. (2004), pp. 201-209.
Campanella, et al., CXCL10 Can Inhibit Endothelial Cell Proliferation Independently of CXCR3, PLOS ONE, vol. 5, No. 9, (2010), e12700, pp. 1-10.
Strieter, et al., CXC Chemokines in Angiogenesis, Cytokine & Growth Factor Reviews, vol. 16 (2005), pp. 593-609.
Muller, et al., Review: The Chemokine Receptor CXCR3 and its Ligand CXCL9, CXCL10 and CXCL11 in Neuroimmunity —A Tale of Conflict and Conundrum, Neuropathology and Applied Neurobiology, (2010), vol. 36, pp. 368-387.
Pease, et al., The Attraction of Chemokines as a Target for Specific Anti-inflammatory Therapy, British Journal of Pharmacology, (2006), vol. 147, pp. S212-221.
Donnelly, et al., Chemokine Receptors as Therapeutic Targets in Chronic Obstructive Pulmonary Disease, TRENDS in Pharmacological Science, vol. 27, No. 10, pp. 546-553, (2006).
Uno, et al., Expression of Chemokines, CXC Chemokine Ligand 10 (CXCL10) and CXCR3 in the Inflamed Islets of Patients With Recent-Onset Autoimmune Type 1 Diabetes. Endocrine Journal, (2010), vol. 57, No. 11, pp. 991-996.

(Continued)

*Primary Examiner* — Shawquia Jackson
(74) *Attorney, Agent, or Firm* — Kelly L. Bender

(57) ABSTRACT

The present invention relates to compounds of formula 1 that are useful for the preventive and/or therapeutic treatment of diseases caused by abnormal activation of CXCR3 chemokines. The invention relates furthermore to a process for the preparation of said compounds, to pharmaceutical compositions containing said compounds and to novel intermediates used in the preparation of said compounds.

17 Claims, No Drawings

(56) References Cited

OTHER PUBLICATIONS

Singh, et al., CXCL10 T Cells and NK Cells Assist in the Recruitment and Activation of CXCR3 and CXCRL11 Leukocytes During Mycobacteria-Enhanced Colitis, BMC Immunology, (2008), vol. 9, No. 25, pp. 1-13.

Pease, et al., Chemokine Receptor Antagonists: Part 2, Expert Opin. Ther. Patents. (2009), vol. 19, No. 2, pp. 199-221.

Hansel, et al., New Drugs for Exacerbations of Chronic Obstructive Pulmonary Disease, Lancet, vol. 374, (2009), pp. 744-755.

Krueger, et al., Psoriasis Pathophysiology: Current Concepts of Pathogenesis, Ann. Rheum. Dis., vol. 64, Suppl. II, pp. ii30-ii36, (2005).

Hancock, et al., Requirement of the Chemokine Receptor CXCR3 for Acute Allograft Rejection, J. Exp. Med., vol. 192, No. 10, pp. 1515-1519, (2000).

Lammers, et al., Identification of a Novel Immunomodulatory Gliadin Peptide That Cause Interleukin-8 Release in a Chemokine Receptor CXCR3-Dependent Manner Only in Patients With Coeliac Disease, Immunology, vol. 132, pp. 432-440, (2010).

Brightling, et al., The CXCL10/CXCR3 Axis Mediates Human Lung Mast Cell Migration to Asthmatic Airway Smooth Muscle, American Journal of Respiratory and Critical Care Medicine, vol. 171, pp. 1103-1108, (2005).

Meller, et al., Chemokines in the Pathogenesis of Lichenoid Tissue Reactions, J. Investigative Dermatology, vol. 129, pp. 315-319, (2009).

Sonogashira, et al., A Convenient Synthesis of Acetylenes : Catalytic Substitution of Acetylenic Hydrogen With Bromoalkenes, lodoarenes, and Bromopyridines, Tetrahedron Letters, vol. 50, pp. 4467-4470, (1975).

Miyaura, et al., A New Stereospecific Cross-Coupling by the Palladium-Catalyzed Reaction of 1-Alkenylboranes With 1-Alkenyl or 1-Alkynyl Halides, Tetrahedron Letter, vol. 36, pp. 3437-3440, (1979).

Hoerning, et al., Subsets of Human CD4+ Regulatory T Cells Express the Peripheral Homing Receptor CXCR3, Eur. J. Immunol., (2011), vol. 41, pp. 2291-2302.

Groom, et al., CXCR3 Ligands: Redundant, Collabarative and Antagonistic Functions, Immunology and Cell Biology, (2011), vol. 89, pp. 207-215.

Chen, et al., Expression of Chemokine Receptor CXCR3 by Lymphocytes and Plasmacytoid Dendritic Cells in Human Psoriatic Lessions, Arch Dermatol Res., vol. 302, pp. 113-123, (2010).

Wenzel, et al., CXCR3 <-> Ligand —Mediated Skin Inflammation in Cutaneous Lichenoid Graft-Versus-Host Disease, J. Am. Acad. Dermatol., vol. 58, pp. 437-442, (2008).

Sorensen, et al., Optic Neuritis: Chemckine Receptor CXCR3 and its Ligands, Br. J. Ophthalmol., vol. 88, pp. 1146-1148, (2004).

Nishimura et al., Chemokines as Novel Therapeutic Targets for Inflammatory Bowel Disease, Annals of New York Acad. Sci., vol. 1173, pp. 350-356, (2009).

Lacotte, et al,. CXCR3, Inflammation, and Autoimmune Diseases, Annal of N.Y. Acad. Sci., vol. 1173, pp. 310-317, (2009).

Shimada, et al., The Role of the CXC L 10/ CXCR3 System in Type Diabetes, Review of Diabetic Studies, vol. 6 No. 2, pp. 81-84, (2009).

Inoue, et al., N-Allylation of Imides Catalyzed by Palladium (0), Bull. Chem. Soc. Jpn., vol. 57, pp. 3021-3022, (1984).

Sauty, et al., CXCR3 Internationalization Following T Cell-Endothelial Cell Contact: Preferential Role of IFN-Inducible T Cell a Chemoattractant (CXCL11), J Immunol, (2001), vol. 167, pp. 7084-7093.

SUBSTITUTED B-AMINO ACID DERIVATIVES AS CXCR3 RECEPTOR ANTAGONISTS

The present invention relates to compounds that are useful as an active ingredient of a medicament for preventive and/or therapeutic treatment of diseases caused by abnormal activation of CXCR3 chemokines.

Chemokines are a large family of small soluble proteins of about 8 to 10 kDa in size. One of the major roles of chemokines is to direct the migration of immune cells. The mechanism by which the movement of cells is guided is the chemical attraction of the cells expressing the relevant chemokine receptor on their surface toward the concentration gradient of the corresponding chemokine.

Some chemokines are homeostatic in function as they regulate the trafficking of cells in a day to day manner. Such homeostatic chemokines, for example direct the homing of lymphocytes to the lymph nodes or they have effect on development by promoting or inhibiting the growth of new blood vessels—thus exerting angiogenic or angiostatic effects.

Other chemokines are expressed in response to inflammation or injury. These inflammatory chemokines regulate the recruitment of specific leukocyte populations into the inflamed tissue that in turn they can elicit the release of specific regulatory and enzymatic factors from the activated immune cells. The expression of these inflammatory chemokines is typically induced by interleukin-1 (IL-1) or interferon-γ (IFN-γ) from various types of cells.

Chemokines exert their function via binding to specific chemokine receptors that are expressed on the cell surface. The chemokine receptors are about 340-360 amino acids long, and they belong to the G-protein coupled receptor (GPCR) super family. To date, approximately 50 chemokines have been identified. Many of them can bind to the same receptor and particular chemokines can also bind to several chemokine receptors. Presently we know altogether 20 different chemokine receptors for these 50 known chemokines [Groom, J. R. and Luster, A. D. 2011. Immunology and Cell Biology, 1-9]. More recently different splice variants have also been described for some chemokine receptors that may have different expression patterns and different physiological or pathophysiological roles.

CXCR3 is an inflammatory chemokine receptor which is predominantly expressed on activated immune cells such as the CD4$^+$ (Th1 helper) and CD8$^+$ (CTL cytotoxic or Tc) T lymphocytes. CXCR3 is absent on naïve T lymphocytes, but its cell surface expression is rapidly induced following T cell activation by dendritic cells. CXCR3 is also expressed on innate lymphocytes such as natural killer cells (NK) and NKT cells, on plasmacytoid dendritic cells (pDC) [Groom, J. R. and Luster, A. D. 2011. Immunology and Cell Biology, 1-9], on inflammatory neutrophils and macrophages.

CXCR3 is selectively activated by three interferon-inducible chemokines, CXCL9 (also termed as Mig), CXCL10 (IP-10) and CXCL11 (I-TAC). Activation of CXCR3 by these endogenous agonists elicits intracellular Ca$^{2+}$ mobilization via phospholipases C (PLC) and, in addition, activation of both mitogen-activated protein kinase (MAP-kinase) and PI3-kinase [Liu, M; Guo, S; Hibbert, J. M; Jain, V; Sinh, N Wilson, N. O; and Stiles, J. K. 2011. Cytokine & Growth Factor Reviews, 22: 121-130.]. These intracellular events finally result in stimulation of lymphocyte migration and proliferation. CXCR3 plays a key role in selective recruitment of activated immune cells to the site of inflammation. Once recruited, cytotoxic T cells (CTL), through the release of perforin and granzyme B, induce apoptosis, thereby contributing to local tissue damage and subsequent remodelling. At the site of inflammation the recruited Th1 and CTL cells release IFN-gamma that stimulates epithelial cells and macrophages to further release of CXCR3 agonists that leads to a persistent inflammatory activation.

Strong Th1 and CTL responses are beneficial during acute infection, but these responses must be counterbalanced to prevent unwanted tissue destruction and chronic immunopathological changes [Groom, J. R. and Luster, A. D. 2011. Experimental Cell Research 317: 620-631]. In this respect CXCR3 antagonists are suggested to have significant therapeutic relevance.

More recent studies demonstrated that CXCR3 is also expressed on human CD25+FOXP3+ regulatory CD4+ T cells (Treg) and the level of CXCR3 increases on Treg cells following activation [Vandercappellen, J et al, 2011. Cytokine & Growth Factor Reviews 22: 1-18.]. This observation suggests that CXCR3 may participate in mediation of trafficking of Treg cells. Treg cells migrate to the peripheral sites of inflammation, where they exert suppressive activity on CD4+ Th1 and CD8+ CTL cells [Hoerning, A et al 2011. Eur J Immunol, online manuscript, accepted: Apr. 26, 2011. DOI: 10.1002/eji.201041095]. Thus Treg cells are important for suppressing the immune responses, maintaining immune tolerance and preventing autoimmune responses.

For the time being little is known about the expression pattern of CXCR3 on Treg subsets or the association of CXCR3 with Treg immunoregulatory functions. However, this finding may explain some reported variable functional effects of CXCR3 blockade in different animal models [Hoerning, A et al 2011. Eur J Immunol, online manuscript, accepted: Apr. 26, 2011. DOI: 10.1002/eji.201041095] or the variable effects of CXCR3 blockade in different types of allograft rejection.

As of today, there are three splice variants for CXCR3 described in humans: CXCR3-A, CXCR3-B [Romagnani, P; Lasagni, L; Annunziato, F; Serio, M. and Romagnani, S. 2004. TRENDS in Immunology, 25: 201-209.] and CXCR3-alt. CXCR3-A is the most abundant variant, it couples to Gi/o type of G-proteins and it mediates chemotaxis and cell proliferation.

The splice variant CXCR3-B is thought to be expressed on endothelial and vascular smooth muscle cells and mediates angiostatic effects [Strieter, R. M; Burdick, M. D; Gomperts, B. N; Belperio, A.; Keane, M. P. 2011. Cytokine & Growth Factor Reviews 16:593-609.]. CXCR3-B can bind not only the three well known CXCR3 agonists, CXCL9 (Mig), CXCL10 (IP-10) and CXCL11 (I-TAC) but also a forth one, CXCL4 (PF-4), which is a selective, CXCR3-B specific chemokine agonist. Activation of CXCR3-B is supposed to mediate the activation of the Gs, the stimulatory type of G-proteins that in turn causes an intracellular cAMP rise, which finally results in angiostatic effects and inhibition of cell proliferation. More recent studies, however, showed that the alternative CXCR3-B splice variant does not exist in mice [Campanella, G. S. V; Colvin, R. A; and Luster, A. D. 2010. PLoS ONE 5(9): e12700. doi:10.1371/journal.pone.0012700] and, in addition to it, the same authors in their experiments with human endothelial cells also demonstrated that CXCL10 can inhibit endothelial cell proliferation independently of CXCR3 receptors. As of today, there are some controversial observations on the putative roles of the different alternative CXCR3 splice variants and thus further studies are still needed in order to clarify and understand their physiological and pathophysiological roles.

On the other hand, it is widely accepted that T lymphocytes play crucial regulatory function in the immune system [Wijtmans, M; Verzijl, D; Leurs, R; de Esch, I. J. P; and Smit, M. J. 2008. ChemMedChem. 3:861-872.] and [Müller, M; Carter, M. J; Hofert, J; and Campbell, I. L. 2010. Neuropathology and Applied Neurobiology, 36:368-387.]. Their special roles are also indicated by the fact that 15 chemokine receptors out of the 20 known ones, are expressed among the different subpopulations of T lymphocytes [Pease and Williams, Br. J. Pharmacol. 2006. 147, S212]. T cells are implicated in many inflammatory diseases.

Clinical evidences showed significant overexpression of CXCR3 receptor and/or its endogenous agonists (CXCL10, CXCL11) in multiple autoimmune or inflammatory diseases, such as e.g.

(i) in peripheral airways of COPD patients [Donnelly, L. E. and Barnes, P. J. Trends in Pharmacol Sci 27(10): 564-553.],
(ii) in skin biopsies from patients with moderate to severe psoriasis [Chen, S-C; Groot, M.; Kinsley, D; Laverty, M; McClanahan, T; Arreaza, M; Gustafson, E. L; Teunissen, M. B. M; Rie, M. A; Jay, S. F; and Kraan, M. 2010. Arch. Dermatol. Rev. 302: 113-123],
(iii) in lymph nodes and islets of type 1 diabetic patients [Uno, S; Imagawa, A; Saisho, K; Okita, K; Iwahashi, H; Hanafusai, T; and Shimomura, I. 2010. Endocrine Journal. 57(11): 991-996.]
(iv) in acute allograft rejection (lung, heart, kidney and skin grafts) [Wenczel, J. Lucas, S; Zahn, S; Mikus, S; Metze, D; Stadter, S, et al, 2008. J. Am. Acad. Dermatol. 58:437-442.]
(v) in colon biopsies of patients with ulcerative colitis [Singh, U. P. Singh, R; Singh, S; Karls, R. K; Quinn, F. D; Taub, D. D; and Lillard Jr J. W. 2008. BMC Immunology 9:25]
and (vi) in thymus from myasthenia gravis patients [Pease, J. E and Horuk, R. 2009. Expert Opin Ther Patents, 19 (2): 199-221].

In animals, CXCR3-KO mice display blocked T cell migration into bronchoalveolar space following noxious stimuli such as cigarette smoke (murine model of COPD). CXCL10-gene deficient or CXCR3-KO mice showed prolonged allograft survival in murine models of transplant rejection (cardiac and pancreatic island allografts).

Blocking the activation of CXCR3 by antagonists represents a possible approach for the treatment of diseases such as COPD [Hansel, T. T. and Barnes, P. J. 2009. Lancet, 374:744-755], psoriasis [Krueger, J. G. and Bowcock, A. 2005. Ann. Rheum. Dis. 64: Suppl.II.: ii30-ii36.], graft/transplant rejection [Hancock, W. W; Lu, B; Gao, W; Cziszmadia, V; Faia, K; King, J. A; Smileey, S. T; Ling, M; Gearad, N. P; and Gerard, C. 2000. J Exp Med 192:1515-1519.], ophthalmological diseases [Sorensen, T. L; Roed, H; Sellebjerg, F. 2004. Br. J. Opthalmol. 88:1146-1148.], celiac disease [Lammers, K. M; Khandelwal, S; Chaudhry, F; Kryszak, D; Puppa, E. L; Casolaro; V; and Fasano, A. 2010. Immunology, 132:432-440.], inflammatory bowel disease (IBD) [Nishimura, M; Kuboi, Y; Muramato, K; Kawano, T; and Imai, T. 2009. Autoimmunity: Ann N.Y. Acad. Sci. 1173:350-356.], type 1 diabetes [Shimida, A; Oikawa, Y; Yamada, Y; Okubo, Y; and Narumi, S. 2009. Review of Diabetic Studies, 6(2): 81-84], myasthenia gravis (MG) [Pease, J. E and Horuk, R. 2009. Expert Opin Ther Patents, 19 (2): 199-221], multiple sclerosis (MS) and other neuroinflammatory diseases [Müller, M; Carter, M. J; Hofert, J; and Campbell, I. L. 2010. Neuropathology and Applied Neurobiology, 36:368-387.], lupus [Lacotte, S; Brun, S; Muller, S; and Dumortier, H. 2009. Autoimmunity: Ann N.Y. Acad. Sci. 1173:310-317.], rheumatoid arthritis (RA) [Brightling, C; Ammit, A. J; Kaur, D; Black, J. L; Wardlaw, A. J; Hughes, J. M; and Bradding, P. 2005. Am J Respir Crit Care Med. 171: 1103-1108.], lichen planus [Meller, S; Gillier, M; and Homey, B. 2009. J. Investigative Dermatology. 129: 315-319.].

Targeting CXCR3 appears a more straightforward way to treat the condition as this abrogates the effects of all three endogenous CXCR3 chemokines at the same time.

Assorted patent applications and granted patents disclose inhibitors of chemokines or CXCR3 receptor, such as WO2003087063, WO200604924, WO2009094168 and WO2009105435 but the known compounds are structurally very different from the compounds according to the present invention.

We aimed to prepare new CXCR3 receptor antagonist compounds, which have strong antagonistic effect and are selective to the CXCR3 receptor. We also aimed that the stability, bioavailability, metabolism, therapeutic index, toxicity and solubility of the new compounds allow their development into a drug substance. A further aim was that the compounds, due to their favourable enteric absorption, can be administered orally.

Thus, the inventors of the present invention have identified compounds represented by the following formula 1 possessing inhibitory activity against CXCR3 receptors.

The present invention thus provides a compound of formula 1

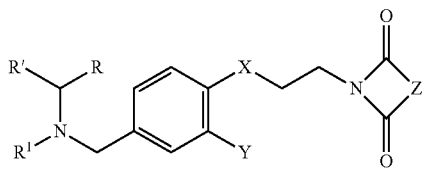

wherein
R represents hydrogen, $C_{1-4}$ alkyl, $C_{3-8}$ cycloalkyl, $C_{1-4}$ halogenalkyl or halogenphenyl group;
R' represents H, or
R and R' represent together with the carbon atom attached a $C_4$ aliphatic ring;
$R^1$ represents a group selected from the group consisting of

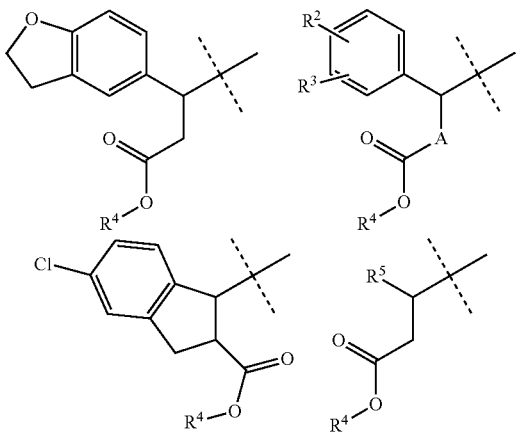

wherein
- A represents a direct bond or CH$_2$, CH(CH$_3$), C(CH$_3$)$_2$ or C(CH$_2$)$_2$ group;
- R$_2$ represents Cl, Me or CF$_3$;
- R$_3$ represents H, Cl or F;
- R$_4$ represents H or C$_{1-4}$ alkyl group;
- R$_5$ represents heteroaryl group selected from the group consisting of

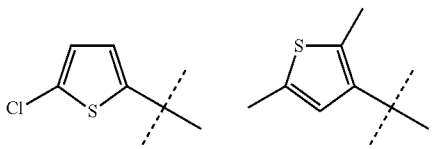

X represents O, S or CH$_2$ group;
Y represents hydrogen, halogen, C$_{1-4}$ alkyl C$_{1-4}$ alkoxy or C$_{1-4}$ hydroxyalkyl group;
Z represents a C$_{1-4}$ aliphatic hydrocarbon bridge optionally containing one double bond, and/or one or more heteroatom selected from O, S, NH and N(CH$_3$) or represents a C$_{2-4}$ aliphatic hydrocarbon bridge optionally containing N fused with a C$_{3-6}$ cycloalkyl ring optionally containing one or more double bond or with a phenyl ring or represents a C$_{1-4}$ aliphatic hydrocarbon bridge substituted with a spiro C$_{3-6}$ cycloalkyl ring optionally containing one or more double bond;
or a pharmaceutically acceptable salt thereof, stereoisomer thereof or a pharmaceutically acceptable salt of the stereoisomer.

According to another aspect of the present invention, there is provided a process for the preparation of a compound of formula 1 or a pharmaceutically acceptable salt, stereoisomer or a pharmaceutically acceptable salt of the stereoisomer, comprising the steps of reductive amination of a benzaldehyde of formula 4

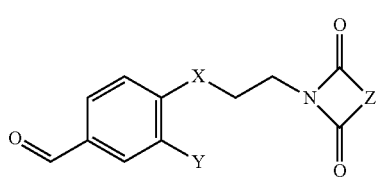

wherein X, Y and Z have the meaning as defined above—
with a primary amine of formula 5

R$^1$—NH$_2$   

wherein R$^1$ has the meaning as defined above—
reacting the obtained secondary amine of formula 2

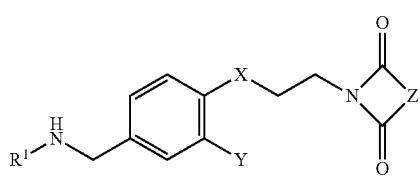

wherein X, Y, Z and R$^1$ have the meaning as defined above— with an aldehyde or cycloalkylketone of formula 3

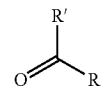

wherein R and R' have the meaning as defined above—
and optionally hydrolyzing the obtained ester of formula 1.

According to another aspect of the present invention there is provided a pharmaceutical composition containing at least one compound of formula 1 or a pharmaceutically acceptable salt, stereoisomer or a pharmaceutically acceptable salt of the stereoisomer and at least one pharmaceutically acceptable excipient.

According to a further aspect the present invention is directed to the compounds of formula 1 or a pharmaceutically acceptable salt, stereoisomer or a pharmaceutically acceptable salt of the stereoisomer for use in the preventive and/or therapeutic treatment of a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) and lichen planus.

In addition the present invention is directed to a method of treating a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) and lichen planus comprising administering an effective amount of a compound of formula 1 or a pharmaceutically acceptable salt or stereoisomer thereof or a pharmaceutically acceptable salt of the stereoisomer to a patient in need thereof.

As used above and throughout the description of the invention, the following terms, unless otherwise indicated, are to be understood to have the following meanings:

The C$_{1-4}$ alkyl group represents a straight or branched alkyl group having 1 to 4 carbon atoms, for example, methyl group, ethyl group, n-propyl group, isopropyl group, n-butyl group, isobutyl group, sec-butyl group, tert-butyl group, and the like.

The C$_{1-4}$ alkoxy group represents an above identified alkyl group having 1 to 4 carbon atoms and attached through an oxygen atom, for example, methoxy group, ethoxy group, propoxy group, isopropoxy group, butoxy group, isobutoxy group, sec-butoxy group, tert-butoxy group, and the like.

The C$_{1-4}$ hydroxyalkyl group represents an above identified alkyl group having 1 to 4 carbon atoms and bearing one or more hydroxy group, for example, hydroxymethyl group, 1-hydroxy-ethyl group, 2-hydroxy-ethyl group, 1-, 2- or 3-hydroxy-n-propyl group, 1- or 2-hydroxy-isopropyl group, and the like The C$_{3-8}$ cycloalkyl group represents a cyclic alkyl group having 3 to 8 carbon atoms in the ring, for example cyclopropyl group, cyclobutyl group, cyclopentyl group, cyclohexyl group, cycloheptyl group or cyclooctyl group.

The halogen atom represents a fluorine, chlorine, bromine or iodine atom.

The $C_{1-4}$ halogenalkyl group represents an above identified alkyl group having 1 to 4 carbon atoms and bearing one or more halogen atom, such as fluorine, chlorine, bromine or iodine atom, particularly fluorine or chlorine atom, for example chloromethyl group, fluoromethyl group, 1- or 2-chloro- or -fluoro-ethyl group, 1-, 2- or 3-chloro- or -fluoro-proyl group, 1- or 2-dichloro- or -difluoro-ethyl group, 1-, 2- or 3-dichloro- or -difluoro-propyl group, 1-trichloro- or -trifluoro-ethyl group or 1-trichloro- or -trifluoro-propyl group and the like.

The halogenphenyl group represents a phenyl moiety bearing on the ring one or more halogen atom, such as fluorine, chlorine, bromine or iodine atom, particularly fluorine or chlorine atom in any position, for example o-, m- or p-chloro-phenyl group, o-, m- or p-fluoro-pehnyl group, 2,3-, 2,4- or 2,5-dichloro- or -difluoro-phenyl group, 2,3,4-, 2,4,5- or 3,4,5-trichloro- or -trifluoro-phenyl group, 2-chloro-3-, -4- or -5-fluoro-phenyl group or 2-fluoro-3-, -4- or -5-chloro-phenyl group and the like.

The $C_4$ aliphatic ring represents a cyclobutyl ring.

The $C(CH_2)_2$ group means 1,1-cyclopropanediyl group

The $C_{1-4}$ aliphatic hydrocarbon bridge optionally containing one double bond and/or one or more heteroatom selected from O, S, NH and $N(CH_3)$ means an alkandiyl group having 1 to 4 carbon atoms and optionally containing one double bond and/or one or more heteroatom selected from O, S, NH and $N(CH_3)$, for example $—CH_2—CH_2—$, $—CH_2—O—$, $—CH_2—S—$, $—CH_2—NH—$, $—CH_2—N(CH_3)—$, $—CH_2—CH_2—CH_2—$, $—CH=CH—N(CH_3)—$, $—N=CH—N(CH_3)—$, and the like.

The $C_{2-4}$ aliphatic hydrocarbon bridge optionally containing N fused with a $C_{3-6}$ cycloalkyl ring optionally containing one or more double bond or with a phenyl ring means an alkandiyl group having 2 to 4 carbon atoms which optionally contains N as heteroatom, and which is fused with a cycloalkyl ring having 3 to 6 carbon atoms and optionally containing one or more double bond or with a phenyl ring for example $—CH(CH_2)CH—$,

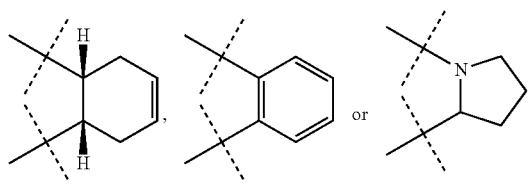

The $C_{1-4}$ aliphatic hydrocarbon bridge substituted with a spiro $C_{3-6}$ cycloalkyl ring optionally containing one or more double bond means an alkandiyl group having 1 to 4 carbon atoms and substituted with a spiro cycloalkyl ring having 3 to 6 carbon atoms and optionally containing one or more double bond, means for example

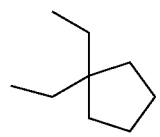

By salts of the compounds of the formula 1 we mean salts formed with inorganic and organic acids. Preferred salts are those given with pharmaceutically acceptable acids as for instance hydrochloric acid, and the like. The salts formed during purification or isolation are also subject of the invention.

The compounds represented by the aforementioned formula 1 may have one or more asymmetric carbon atoms. Thus, they can exist in the form of optical isomers, enantiomers or diastereoisomers. These optical isomers, enantiomers and diastereoisomers as well as their mixtures, including the racemates, are also subject of the invention.

An embodiment of the invention includes the compound of formula 1 wherein

R represents hydrogen, $C_{1-4}$ alkyl, $C_{3-8}$ cycloalkyl, $C_{1-4}$ halogenalkyl or halogenphenyl group;

R' represents hydrogen or

R and R' represent together with the carbon atom attached a $C_4$ aliphatic ring;

$R^1$ represents a group selected from the group consisting of

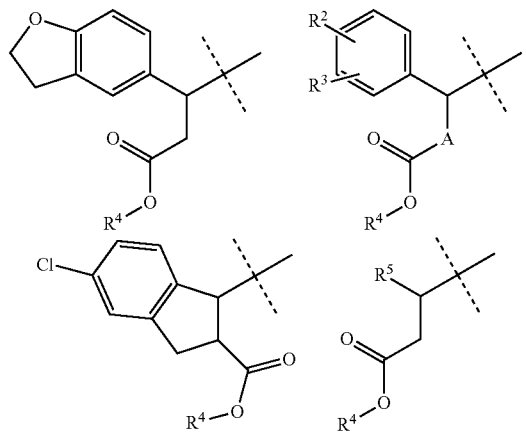

wherein
A represents a direct bond or $CH_2$, $CH(CH_3)$, $C(CH_3)_2$ or $C(CH_2)_2$ group;
$R_2$ represents Cl, Me or $CF_3$;
$R_3$ represents hydrogen, Cl or F;
$R_4$ represents hydrogen or $C_{1-4}$ alkyl group;
$R_5$ represents heteroaryl group selected from the group consisting of

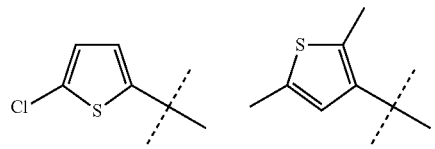

X represents O, S or $CH_2$ group;
Y represents halogen, $C_{1-4}$ alkyl or $C_{1-4}$ alkoxygroup;
Z represents $(CH_2)_2$, $CH_2N(CH_3)$ or $CH=CH—N(CH_3)$ group;
or a pharmaceutically acceptable salt thereof, stereoisomer thereof or a pharmaceutically acceptable salt of the stereoisomer.

Another embodiment of the invention includes a compound of formula 1, wherein $R^4$ represents hydrogen, or a pharmaceutically acceptable salt or stereoisomer thereof or a pharmaceutically acceptable salt of the stereoisomer.

Another embodiment of the invention includes a compound of formula 1, wherein $R^1$ represents a group selected from the group consisting of

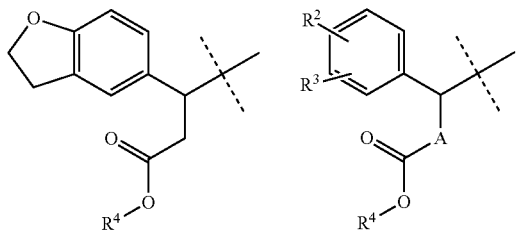

wherein A represents $CH_2$ group;
$R_2$ represents Cl, Me or $CF_3$;
$R_3$ represents hydrogen, Cl, or F;
$R_4$ represents hydrogen;
or a pharmaceutically acceptable salt or stereoisomer thereof or a pharmaceutically acceptable salt of the stereoisomer.

Another embodiment of the invention includes a compound of formula 1, wherein $R^1$ represents a group selected from the group consisting of

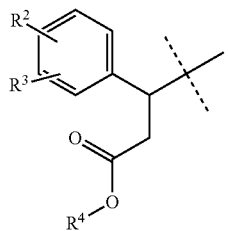

wherein $R_2$ represents Cl;
$R_3$ represents hydrogen, Cl, or F;
$R_4$ represents hydrogen;
or a pharmaceutically acceptable salt or stereoisomer thereof or a pharmaceutically acceptable salt of the stereoisomer.

Another embodiment of the invention includes a compound of formula 1, wherein X represents an O atom- or a pharmaceutically acceptable salt or stereoisomer thereof or a pharmaceutically acceptable salt of the stereoisomer.

Another embodiment of the invention includes a compound of formula 1, wherein Y represents halogen, $CH_3$, $C_2H_5$ or $OCH_3$ group or a pharmaceutically acceptable salt or stereoisomer thereof or a pharmaceutically acceptable salt of the stereoisomer.

Another embodiment of the invention includes a compound of formula 1, wherein Y represents Cl, F, $CH_3$, $C_2H_5$ or $OCH_3$ group or a pharmaceutically acceptable salt or stereoisomer thereof or a pharmaceutically acceptable salt of the stereoisomer.

Another embodiment of the invention includes a compound of formula 1, wherein Z represents $(CH_2)_2CH_2N(CH_3)$, $CH=N(CH_3)$ group or a pharmaceutically acceptable salt or stereoisomer thereof or a pharmaceutically acceptable salt of the stereoisomer. Another embodiment of the invention includes a compound of formula 1, wherein Z represents $(CH_2)_2$ group or a pharmaceutically acceptable salt or stereoisomer thereof or a pharmaceutically acceptable salt of the stereoisomer.

Another embodiment of the invention includes a compound of formula 1, wherein

R represents hydrogen, $C_{1-4}$ alkyl group, $C_{3-6}$ cycloalkyl or fluorophenyl group;
R' represents hydrogen;
or a pharmaceutically acceptable salt or stereoisomer thereof or a pharmaceutically acceptable salt of the stereoisomer.

An other embodiment of the invention includes a compound of formula 1, wherein
R represents hydrogen, $C_{1-4}$ alkyl, $C_{3-6}$ cycloalkyl or fluorophenyl group;
R' represents hydrogen;
$R^1$ represents a group selected from the group consisting of

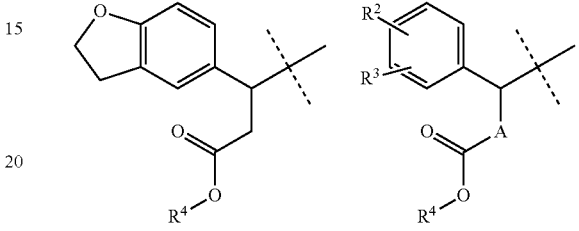

wherein A represents $CH_2$ group;
$R_2$ represents Cl, Me or $CF_3$;
$R_3$ represents hydrogen, Cl, or F;
$R_4$ represents hydrogen;
X represents O, S or $CH_2$ group;
Y halogen, $CH_3$, $C_2H_5$ or $OCH_3$ group;
Z represents $(CH_2)_2$, $CH_2N(CH_3)$ or $CH=CH-N(CH_3)$ group;
or a pharmaceutically acceptable salt thereof, stereoisomer thereof or a pharmaceutically acceptable salt of the stereoisomer.

Particularly compounds of the present invention represented by formula 1 include compounds selected from the group consisting of:

1. 3-(2,3-Dihydro-benzofuran-5-yl)-3-({4-[2-(2,5-dioxo-pyrrolidin-1-yl)-ethoxy]-3-methoxy-benzyl}-isobutyl-amino)-propionic acid
1.1 3-(2,3-Dihydro-benzofuran-5-yl)-3-({4-[2-(2,5-dioxo-pyrrolidin-1-yl)-ethoxy]-3-ethoxy-benzyl}-isobutyl-amino)-propionic acid ethyl ester naphthalene-1,5-disulfonic acid salt
2. 3-(4-Chloro-phenyl)-3-({4-[2-(2,5-dioxo-pyrrolidin-1-yl)-ethoxy]-3-methoxy-benzyl}-isobutyl-amino)-propionic acid
3. 3-(Cyclopentylmethyl-{4-[2-(2,5-dioxo-pyrrolidin-1-yl)-ethoxy]-3-methoxy-benzyl}-amino)-3-(2,4-dichloro-phenyl)-propionic acid
4. 3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid
5. (S)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid
6. (R)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid
7. 3-(4-Chloro-phenyl)-3-(cyclobutyl-{3-methyl-4-[2-(3-methyl-2,6-dioxo-3,6-dihydro-2H-pyrimidin-1-yl)-ethoxy]-benzyl}-amino)-propionic acid
8. 1-[(4-Chloro-phenyl)-({4-[2-(2,5-dioxo-pyrrolidin-1-yl)-ethoxy]-3-methyl-benzyl}-propyl-amino)-methyl]-cyclopropanecarboxylic acid 9. (S)-3-(4-Chloro-phenyl)-3-({4-[2-(2,5-dioxo-pyrrolidin-1-yl)-ethoxy]-3-methyl-benzyl}-propyl-amino)-propionic acid
10. (R)-3-(4-Chloro-phenyl)-3-({4-[2-(2,5-dioxo-pyrrolidin-1-yl)-ethoxy]-3-methyl-benzyl}-propyl-amino)-propionic acid
11. (S)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid; hydrochloride
12. (R)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid; hydrochloride
13. (S)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid; hydrochloride
14. (R)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid; hydrochloride
15. (S)-3-({3-Chloro-4-[2-(2,5-dioxo-pyrrolidin-1-yl)-ethoxy]-benzyl}-cyclopropyl-ethyl-amino)-3-(4-chloro-3-fluoro-phenyl)-propionic acid; hydrochloride
16. (R)-3-({3-Chloro-4-[2-(2,5-dioxo-pyrrolidin-1-yl)-ethoxy]-benzyl}-cyclopropyl-ethyl-amino)-3-(4-chloro-3-fluoro-phenyl)-propionic acid; hydrochloride
17. (S)-3-(4-Chloro-3-fluoro-phenyl)-3-(cyclopentylmethyl-{4-[2-(2,5-dioxo-pyrrolidin-1-yl)-ethoxy]-3-methoxy-benzyl}-amino)-propionic acid
18. (R)-3-(4-Chloro-3-fluoro-phenyl)-3-(cyclopentylmethyl-{4-[2-(2,5-dioxo-pyrrolidin-1-yl)-ethoxy]-3-methoxy-benzyl}-amino)-propionic acid
19. (S)-3-(4-Chloro-3-fluoro-phenyl)-3-(cyclopropylmethyl-{4-[2-(2,5-dioxo-pyrrolidin-1-yl)-ethoxy]-3-fluoro-benzyl}-amino)-propionic acid; hydrochloride
20. (R)-3-(4-Chloro-3-fluoro-phenyl)-3-(cyclopropylmethyl-{4-[2-(2,5-dioxo-pyrrolidin-1-yl)-ethoxy]-3-fluoro-benzyl}-amino)-propionic acid; hydrochloride
21. (S)-3-(4-Chloro-3-fluoro-phenyl)-3-({4-[2-(2,5-dioxo-pyrrolidin-1-yl)-ethoxy]-3-fluoro-benzyl}-isobutyl-amino)-propionic acid; hydrochloride
22. (R)-3-(4-Chloro-3-fluoro-phenyl)-3-({4-[2-(2,5-dioxo-pyrrolidin-1-yl)-ethoxy]-3-fluoro-benzyl}-isobutyl-amino)-propionic acid; hydrochloride
23. (S)-3-(4-Chloro-phenyl)-3-(cyclopropylmethyl-{4-[2-(2,5-dioxo-pyrrolidin-1-yl)-ethoxy]-3-methyl-benzyl}-amino)-propionic acid
24. (S)-3-(4-Chloro-3-fluoro-phenyl)-3-({4-[2-(2,5-dioxo-pyrrolidin-1-yl)-ethoxy]-3-methyl-benzyl}-isobutyl-amino)-propionic acid; hydrochloride
25. (R)-3-(4-Chloro-3-fluoro-phenyl)-3-({4-[2-(2,5-dioxo-pyrrolidin-1-yl)-ethoxy]-3-methyl-benzyl}-isobutyl-amino)-propionic acid; hydrochloride
26. (S)-3-(Cyclopropylmethyl-{4-[2-(2,5-dioxo-pyrrolidin-1-yl)-ethoxy]-3-methyl-benzyl}-amino)-3-(3,4-dichloro-phenyl)-propionic acid
27. (R)-3-(Cyclopropylmethyl-{4-[2-(2,5-dioxo-pyrrolidin-1-yl)-ethoxy]-3-methyl-benzyl}-amino)-3-(3,4-dichloro-phenyl)-propionic acid
28. (S)-3-(4-Chloro-phenyl)-3-(cyclopentylmethyl-{4-[2-(2,5-dioxo-pyrrolidin-1-yl)-ethoxy]-3-ethyl-benzyl}-amino)-propionic acid
29. (R)-3-(4-Chloro-phenyl)-3-(cyclopentylmethyl-{4-[2-(2,5-dioxo-pyrrolidin-1-yl)-ethoxy]-3-ethyl-benzyl}-amino)-propionic acid
30. (S)-3-(4-Chloro-phenyl)-3-(cyclohexylmethyl-{3-methyl-4-[2-(3-methyl-2,5-dioxo-imidazolidin-1-yl)-ethoxy]-benzyl}-amino)-propionic acid
31. (R)-3-(4-Chloro-phenyl)-3-(cyclohexylmethyl-{3-methyl-4-[2-(3-methyl-2,5-dioxo-imidazolidin-1-yl)-ethoxy]-benzyl}-amino)-propionic acid
32. (S)-3-(4-Chloro-3-fluoro-phenyl)-3-(cyclopentylmethyl-{3-methyl-4-[2-(3-methyl-2,5-dioxo-imidazolidin-1-yl)-ethoxy]-benzyl}-amino)-propionic acid
33. (R)-3-(4-Chloro-3-fluoro-phenyl)-3-(cyclopentylmethyl-{3-methyl-4-[2-(3-methyl-2,5-dioxo-imidazolidin-1-yl)-ethoxy]-benzyl}-amino)-propionic acid
34. (S)-3-(4-Chloro-3-fluoro-phenyl)-3-(cyclohexylmethyl-{3-methyl-4-[2-(3-methyl-2,5-dioxo-imidazolidin-1-yl)-ethoxy]-benzyl}-amino)-propionic acid
35. (R)-3-(4-Chloro-3-fluoro-phenyl)-3-(cyclohexylmethyl-{3-methyl-4-[2-(3-methyl-2,5-dioxo-imidazolidin-1-yl)-ethoxy]-benzyl}-amino)-propionic acid
36. 3-(4-Chloro-phenyl)-3-(cyclopropylmethyl-{4-[2-(2,5-dioxo-pyrrolidin-1-yl)-ethoxy]-3-methoxy-benzyl}-amino)-propionic acid
37. 3-(4-Chloro-phenyl)-3-({4-[2-(2,5-dioxo-pyrrolidin-1-yl)-ethoxy]-3-methoxy-benzyl}-propyl-amino)-propionic acid
38. 3-(Butyl-{4-[2-(2,5-dioxo-pyrrolidin-1-yl)-ethoxy]-3-methoxy-benzyl}-amino)-3-(4-chloro-phenyl)-propionic acid
39. 3-(4-Chloro-phenyl)-3-(cyclopentylmethyl-{4-[2-(2,5-dioxo-pyrrolidin-1-yl)-ethoxy]-3-methoxy-benzyl}-amino)-propionic acid
40. 3-(4-Chloro-phenyl)-3-(cyclohexylmethyl-{4-[2-(2,5-dioxo-pyrrolidin-1-yl)-ethoxy]-3-methoxy-benzyl}-amino)-propionic acid
41. 3-(4-Chloro-3-fluoro-phenyl)-3-({4-[2-(2,5-dioxo-pyrrolidin-1-yl)-ethoxy]-3-methoxy-benzyl}-propyl-amino)-propionic acid
42. 3-(4-Chloro-3-fluoro-phenyl)-3-({4-[2-(2,5-dioxo-pyrrolidin-1-yl)-ethoxy]-3-methoxy-benzyl}-isobutyl-amino)-propionic acid
43. 3-(Butyl-{4-[2-(2,5-dioxo-pyrrolidin-1-yl)-ethoxy]-3-methoxy-benzyl}-amino)-3-(4-chloro-3-fluoro-phenyl)-propionic acid
44. 3-(4-Chloro-3-fluoro-phenyl)-3-(cyclohexylmethyl-{4-[2-(2,5-dioxo-pyrrolidin-1-yl)-ethoxy]-3-methoxy-benzyl}-amino)-propionic acid
45. 3-(Cyclopropylmethyl-{4-[2-(2,5-dioxo-pyrrolidin-1-yl)-ethoxy]-3-methoxy-benzyl}-amino)-3-(3,4-dichloro-phenyl)-propionic acid
46. 3-(3,4-Dichloro-phenyl)-3-({4-[2-(2,5-dioxo-pyrrolidin-1-yl)-ethoxy]-3-methoxy-benzyl}-propyl-amino)-propionic acid
47. 3-(3,4-Dichloro-phenyl)-3-({4-[2-(2,5-dioxo-pyrrolidin-1-yl)-ethoxy]-3-methoxy-benzyl}-isobutyl-amino)-propionic acid
48. 3-(Butyl-{4-[2-(2,5-dioxo-pyrrolidin-1-yl)-ethoxy]-3-methoxy-benzyl}-amino)-3-(3,4-dichloro-phenyl)-propionic acid
49. 3-(Cyclopentylmethyl-{4-[2-(2,5-dioxo-pyrrolidin-1-yl)-ethoxy]-3-methoxy-benzyl}-amino)-3-(3,4-dichloro-phenyl)-propionic acid
50. 3-(Cyclohexylmethyl-{4-[2-(2,5-dioxo-pyrrolidin-1-yl)-ethoxy]-3-methoxy-benzyl}-amino)-3-(3,4-dichloro-phenyl)-propionic acid
51. 3-(4-Chloro-phenyl)-3-(cyclopropylmethyl-{4-[2-(2,5-dioxo-pyrrolidin-1-yl)-ethoxy]-3-fluoro-benzyl}-amino)-propionic acid
52. (R)-3-(4-Chloro-phenyl)-3-({4-[2-(2,5-dioxo-pyrrolidin-1-yl)-ethoxy]-3-fluoro-benzyl}-propyl-amino)-propionic acid 53. 3-(4-Chloro-phenyl)-3-({4-[2-(2,5-dioxo-pyrrolidin-1-yl)-ethoxy]-3-fluoro-benzyl}-isobutyl-amino)-propionic acid
54. 3-(Butyl-{4-[2-(2,5-dioxo-pyrrolidin-1-yl)-ethoxy]-3-fluoro-benzyl}-amino)-3-(4-chloro-phenyl)-propionic acid
55. (R)-3-(4-Chloro-phenyl)-3-(cyclobutylmethyl-{4-[2-(2,5-dioxo-pyrrolidin-1-yl)-ethoxy]-3-fluoro-benzyl}-amino)-propionic acid
56. 3-(4-Chloro-phenyl)-3-(cyclopentylmethyl-{4-[2-(2,5-dioxo-pyrrolidin-1-yl)-ethoxy]-3-fluoro-benzyl}-amino)-propionic acid
57. 3-(4-Chloro-phenyl)-3-(cyclohexylmethyl-{4-[2-(2,5-dioxo-pyrrolidin-1-yl)-ethoxy]-3-fluoro-benzyl}-amino)-propionic acid
58. 3-(4-Chloro-3-fluoro-phenyl)-3-({4-[2-(2,5-dioxo-pyrrolidin-1-yl)-ethoxy]-3-fluoro-benzyl}-propyl-amino)-propionic acid
59. 3-(Butyl-{4-[2-(2,5-dioxo-pyrrolidin-1-yl)-ethoxy]-3-fluoro-benzyl}-amino)-3-(4-chloro-3-fluoro-phenyl)-propionic acid
60. 3-(4-Chloro-3-fluoro-phenyl)-3-(cyclopentylmethyl-{4-[2-(2,5-dioxo-pyrrolidin-1-yl)-ethoxy]-3-fluoro-benzyl}-amino)-propionic acid
61. 3-(4-Chloro-3-fluoro-phenyl)-3-(cyclohexylmethyl-{4-[2-(2,5-dioxo-pyrrolidin-1-yl)-ethoxy]-3-fluoro-benzyl}-amino)-propionic acid
62. 3-(3,4-Dichloro-phenyl)-3-({4-[2-(2,5-dioxo-pyrrolidin-1-yl)-ethoxy]-3-fluoro-benzyl}-propyl-amino)-propionic acid
63. 3-(3,4-Dichloro-phenyl)-3-({4-[2-(2,5-dioxo-pyrrolidin-1-yl)-ethoxy]-3-fluoro-benzyl}-isobutyl-amino)-propionic acid
64. 3-(Butyl-{4-[2-(2,5-dioxo-pyrrolidin-1-yl)-ethoxy]-3-fluoro-benzyl}-amino)-3-(3,4-dichloro-phenyl)-propionic acid
65. 3-(Cyclopentylmethyl-{4-[2-(2,5-dioxo-pyrrolidin-1-yl)-ethoxy]-3-fluoro-benzyl}-amino)-3-(3,4-dichloro-phenyl)-propionic acid
66. 3-(Cyclohexylmethyl-{4-[2-(2,5-dioxo-pyrrolidin-1-yl)-ethoxy]-3-fluoro-benzyl}-amino)-3-(3,4-dichloro-phenyl)-propionic acid
67. 3-(4-Chloro-phenyl)-3-({4-[2-(2,5-dioxo-pyrrolidin-1-yl)-ethoxy]-3-methyl-benzyl}-ethyl-amino)-propionic acid
68. 3-(4-Chloro-phenyl)-3-(cyclobutyl-{4-[2-(2,5-dioxo-pyrrolidin-1-yl)-ethoxy]-3-methyl-benzyl}-amino)-propionic acid
69. 3-(4-Chloro-phenyl)-3-({4-[2-(2,5-dioxo-pyrrolidin-1-yl)-ethoxy]-3-methyl-benzyl}-isobutyl-amino)-propionic acid
70. 3-(Butyl-{4-[2-(2,5-dioxo-pyrrolidin-1-yl)-ethoxy]-3-methyl-benzyl}-amino)-3-(4-chloro-phenyl)-propionic acid
71. (S)-3-(4-Chloro-phenyl)-3-(cyclobutylmethyl-{4-[2-(2,5-dioxo-pyrrolidin-1-yl)-ethoxy]-3-methyl-benzyl}-amino)-propionic acid
72. 3-(4-Chloro-phenyl)-3-(cyclopentylmethyl-{4-[2-(2,5-dioxo-pyrrolidin-1-yl)-ethoxy]-3-methyl-benzyl}-amino)-propionic acid
73. 3-(4-Chloro-phenyl)-3-(cyclohexylmethyl-{4-[2-(2,5-dioxo-pyrrolidin-1-yl)-ethoxy]-3-methyl-benzyl}-amino)-propionic acid
74. 3-(4-Chloro-3-fluoro-phenyl)-3-(cyclopropylmethyl-{4-[2-(2,5-dioxo-pyrrolidin-1-yl)-ethoxy]-3-methyl-benzyl}-amino)-propionic acid
75. 3-(4-Chloro-3-fluoro-phenyl)-3-({4-[2-(2,5-dioxo-pyrrolidin-1-yl)-ethoxy]-3-methyl-benzyl}-propyl-amino)-propionic acid
76. 3-(Butyl-{4-[2-(2,5-dioxo-pyrrolidin-1-yl)-ethoxy]-3-methyl-benzyl}-amino)-3-(4-chloro-3-fluoro-phenyl)-propionic acid
77. 3-(4-Chloro-3-fluoro-phenyl)-3-(cyclopentylmethyl-{4-[2-(2,5-dioxo-pyrrolidin-1-yl)-ethoxy]-3-methyl-benzyl}-amino)-propionic acid
78. 3-(4-Chloro-3-fluoro-phenyl)-3-(cyclohexylmethyl-{4-[2-(2,5-dioxo-pyrrolidin-1-yl)-ethoxy]-3-methyl-benzyl}-amino)-propionic acid
79. 3-(3,4-Dichloro-phenyl)-3-({4-[2-(2,5-dioxo-pyrrolidin-1-yl)-ethoxy]-3-methyl-benzyl}-propyl-amino)-propionic acid
80. 3-(3,4-Dichloro-phenyl)-3-({4-[2-(2,5-dioxo-pyrrolidin-1-yl)-ethoxy]-3-methyl-benzyl}-isobutyl-amino)-propionic acid
81. 3-(Butyl-{4-[2-(2,5-dioxo-pyrrolidin-1-yl)-ethoxy]-3-methyl-benzyl}-amino)-3-(3,4-dichloro-phenyl)-propionic acid
82. 3-(Cyclopentylmethyl-{4-[2-(2,5-dioxo-pyrrolidin-1-yl)-ethoxy]-3-methyl-benzyl}-amino)-3-(3,4-dichloro-phenyl)-propionic acid
83. 3-(Cyclohexylmethyl-{4-[2-(2,5-dioxo-pyrrolidin-1-yl)-ethoxy]-3-methyl-benzyl}-amino)-3-(3,4-dichloro-phenyl)-propionic acid
84. 3-(4-Chloro-phenyl)-3-(cyclopropylmethyl-{4-[2-(2,5-dioxo-pyrrolidin-1-yl)-ethoxy]-3-ethyl-benzyl}-amino)-propionic acid
85. 3-(4-Chloro-phenyl)-3-({4-[2-(2,5-dioxo-pyrrolidin-1-yl)-ethoxy]-3-ethyl-benzyl}-propyl-amino)-propionic acid
86. 3-(4-Chloro-phenyl)-3-({4-[2-(2,5-dioxo-pyrrolidin-1-yl)-ethoxy]-3-ethyl-benzyl}-isobutyl-amino)-propionic acid
87. 3-(Butyl-{4-[2-(2,5-dioxo-pyrrolidin-1-yl)-ethoxy]-3-ethyl-benzyl}-amino)-3-(4-chloro-phenyl)-propionic acid
88. (S)-3-(4-Chloro-phenyl)-3-(cyclobutylmethyl-{4-[2-(2,5-dioxo-pyrrolidin-1-yl)-ethoxy]-3-ethyl-benzyl}-amino)-propionic acid
89. 3-(4-Chloro-phenyl)-3-(cyclohexylmethyl-{4-[2-(2,5-dioxo-pyrrolidin-1-yl)-ethoxy]-3-ethyl-benzyl}-amino)-propionic acid
90. 3-(4-Chloro-3-fluoro-phenyl)-3-(cyclopropylmethyl-{4-[2-(2,5-dioxo-pyrrolidin-1-yl)-ethoxy]-3-ethyl-benzyl}-amino)-propionic acid
91. 3-(4-Chloro-3-fluoro-phenyl)-3-({4-[2-(2,5-dioxo-pyrrolidin-1-yl)-ethoxy]-3-ethyl-benzyl}-propyl-amino)-propionic acid
92. 3-(4-Chloro-3-fluoro-phenyl)-3-({4-[2-(2,5-dioxo-pyrrolidin-1-yl)-ethoxy]-3-ethyl-benzyl}-isobutyl-amino)-propionic acid
93. 3-(Butyl-{4-[2-(2,5-dioxo-pyrrolidin-1-yl)-ethoxy]-3-ethyl-benzyl}-amino)-3-(4-chloro-3-fluoro-phenyl)-propionic acid
94. 3-(4-Chloro-3-fluoro-phenyl)-3-(cyclopentylmethyl-{4-[2-(2,5-dioxo-pyrrolidin-1-yl)-ethoxy]-3-ethyl-benzyl}-amino)-propionic acid
95. 3-(4-Chloro-3-fluoro-phenyl)-3-(cyclohexylmethyl-{4-[2-(2,5-dioxo-pyrrolidin-1-yl)-ethoxy]-3-ethyl-benzyl}-amino)-propionic acid
96. 3-(Cyclopropylmethyl-{4-[2-(2,5-dioxo-pyrrolidin-1-yl)-ethoxy]-3-ethyl-benzyl}-amino)-3-(3,4-dichloro-phenyl)-propionic acid 97. 3-(3,4-Dichloro-phenyl)-3-({4-[2-(2,5-dioxo-pyrrolidin-1-yl)-ethoxy]-3-ethyl-benzyl}-propyl-amino)-propionic acid
98. 3-(3,4-Dichloro-phenyl)-3-({4-[2-(2,5-dioxo-pyrrolidin-1-yl)-ethoxy]-3-ethyl-benzyl}-isobutyl-amino)-propionic acid
99. 3-(Butyl-{4-[2-(2,5-dioxo-pyrrolidin-1-yl)-ethoxy]-3-ethyl-benzyl}-amino)-3-(3,4-dichloro-phenyl)-propionic acid
100. 3-(Cyclopentylmethyl-{4-[2-(2,5-dioxo-pyrrolidin-1-yl)-ethoxy]-3-ethyl-benzyl}-amino)-3-(3,4-dichloro-phenyl)-propionic acid
101. 3-(Cyclohexylmethyl-{4-[2-(2,5-dioxo-pyrrolidin-1-yl)-ethoxy]-3-ethyl-benzyl}-amino)-3-(3,4-dichloro-phenyl)-propionic acid
102. 3-({3-Chloro-4-[2-(2,5-dioxo-pyrrolidin-1-yl)-ethoxy]-benzyl}-cyclopropylmethyl-amino)-3-(4-chloro-phenyl)-propionic acid; hydrochloride
103. 3-({3-Chloro-4-[2-(2,5-dioxo-pyrrolidin-1-yl)-ethoxy]-benzyl}-propyl-amino)-3-(4-chloro-phenyl)-propionic acid
104. (S)-3-({3-Chloro-4-[2-(2,5-dioxo-pyrrolidin-1-yl)-ethoxy]-benzyl}-cyclobutylmethyl-amino)-3-(4-chloro-phenyl)-propionic acid
105. 3-({3-Chloro-4-[2-(2,5-dioxo-pyrrolidin-1-yl)-ethoxy]-benzyl}-propyl-amino)-3-(4-chloro-3-fluoro-phenyl)-propionic acid
106. 3-({3-Chloro-4-[2-(2,5-dioxo-pyrrolidin-1-yl)-ethoxy]-benzyl}-cyclopropylmethyl-amino)-3-(3,4-dichloro-phenyl)-propionic acid; hydrochloride
107. 3-({3-Chloro-4-[2-(2,5-dioxo-pyrrolidin-1-yl)-ethoxy]-benzyl}-propyl-amino)-3-(3,4-dichloro-phenyl)-propionic acid
108. (S)-(Cyclopropylmethyl-{4-[2-(2,5-dioxo-pyrrolidin-1-yl)-ethoxy]-3-methoxy-benzyl}-amino)-(3,4-dichloro-phenyl)-acetic acid
109. (S)-(3,4-Dichloro-phenyl)-({4-[2-(2,5-dioxo-pyrrolidin-1-yl)-ethoxy]-3-methoxy-benzyl}-propyl-amino)-acetic acid
110. (R)-(3,4-Dichloro-phenyl)-({4-[2-(2,5-dioxo-pyrrolidin-1-yl)-ethoxy]-3-methoxy-benzyl}-isobutyl-amino)-acetic acid
111. (R)-(Cyclopropylmethyl-{4-[2-(2,5-dioxo-pyrrolidin-1-yl)-ethoxy]-3-methoxy-benzyl}-amino)-(3,4-dichloro-phenyl)-acetic acid
112. 3-(4-Chloro-phenyl)-3-(ethyl-{3-methyl-4-[2-(3-methyl-2,6-dioxo-3,6-dihydro-2H-pyrimidin-1-yl)-ethoxy]-benzyl}-amino)-propionic acid
113. 3-(4-Chloro-phenyl)-3-({3-methyl-4-[2-(3-methyl-2,6-dioxo-3,6-dihydro-2H-pyrimidin-1-yl)-ethoxy]-benzyl}-propyl-amino)-propionic acid
114. 3-(4-Chloro-phenyl)-3-(cyclopropylmethyl-{3-methyl-4-[2-(3-methyl-2,6-dioxo-3,6-dihydro-2H-pyrimidin-1-yl)-ethoxy]-benzyl}-amino)-propionic acid
115. 3-(4-Chloro-phenyl)-3-(ethyl-{3-methoxy-4-[2-(3-methyl-2,6-dioxo-3,6-dihydro-2H-pyrimidin-1-yl)-ethoxy]-benzyl}-amino)-propionic acid
116. 3-(4-Chloro-phenyl)-3-(cyclopropylmethyl-{3-methoxy-4-[2-(3-methyl-2,6-dioxo-3,6-dihydro-2H-pyrimidin-1-yl)-ethoxy]-benzyl}-amino)-propionic acid
117. 3-(4-Chloro-phenyl)-3-({3-methoxy-4-[2-(3-methyl-2,6-dioxo-3,6-dihydro-2H-pyrimidin-1-yl)-ethoxy]-benzyl}-propyl-amino)-propionic acid
118. 3-(Butyl-{3-methoxy-4-[2-(3-methyl-2,6-dioxo-3,6-dihydro-2H-pyrimidin-1-yl)-ethoxy]-benzyl}-amino)-3-(4-chloro-phenyl)-propionic acid
119. 3-(4-Chloro-phenyl)-3-cyclobutyl-{3-methoxy-4-[2-(3-methyl-2,6-dioxo-3,6-dihydro-2H-pyrimidin-1-yl)-ethoxy]-benzyl}-amino)-propionic acid
120. 3-(Cyclopropylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
121. 3-(2,3-Dihydro-benzofuran-5-yl)-3-(isobutyl-{3-methoxy-4-[2-(3-methyl-2,6-dioxo-3,6-dihydro-2H-pyrimidin-1-yl)-ethoxy]-benzyl}-amino)-propionic acid
122. 3-(Butyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
123. 3-(2,3-Dihydro-benzofuran-5-yl)-3-({3-methoxy-4-[2-(3-methyl-2,6-dioxo-3,6-dihydro-2H-pyrimidin-1-yl)-ethoxy]-benzyl}-propyl-amino)-propionic acid
124. 3-(Cyclopropylmethyl-{3-methoxy-4-[2-(3-methyl-2,6-dioxo-3,6-dihydro-2H-pyrimidin-1-yl)-ethoxy]-benzyl}-amino)-3-(3,4-dichloro-phenyl)-propionic acid
125. 3-(3,4-Dichloro-phenyl)-3-({3-methoxy-4-[2-(3-methyl-2,6-dioxo-3,6-dihydro-2H-pyrimidin-1-yl)-ethoxy]-benzyl}-propyl-amino)-propionic acid
126. 3-(3,4-Dichloro-phenyl)-3-(ethyl-{3-methoxy-4-[2-(3-methyl-2,6-dioxo-3,6-dihydro-2H-pyrimidin-1-yl)-ethoxy]-benzyl}-amino)-propionic acid
127. 3-(Cyclopentylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
128. 3-(Cyclohexylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
129. 3-(4-Chloro-phenyl)-3-[{3-methyl-4-[2-(3-methyl-2,6-dioxo-3,6-dihydro-2H-pyrimidin-1-yl)-ethoxy]-benzyl}-(3,3,3-trifluoro-propyl)-amino]-propionic acid
130. 3-(4-Chloro-phenyl)-3-[{3-methoxy-4-[2-(3-methyl-2,6-dioxo-3,6-dihydro-2H-pyrimidin-1-yl)-ethoxy]-benzyl}-(3,3,3-trifluoro-propyl)-amino]-propionic acid
131. 3-(Cyclopropylmethyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
132. 3-(4-Chloro-phenyl)-3-(cyclopropylmethyl-{4-[3-(2,5-dioxo-pyrrolidin-1-yl)-propyl]-3-methoxy-benzyl}-amino)-propionic acid
133. 3-(4-Chloro-phenyl)-3-({4-[3-(2,5-dioxo-pyrrolidin-1-yl)-propyl]-3-methoxy-benzyl}-propyl-amino)-propionic acid
134. 3-(4-Chloro-phenyl)-3-({4-[3-(2,5-dioxo-pyrrolidin-1-yl)-propyl]-3-methoxy-benzyl}-isobutyl-amino)-propionic acid
135. 3-(Butyl-{4-[3-(2,5-dioxo-pyrrolidin-1-yl)-propyl]-3-methoxy-benzyl}-amino)-3-(4-chloro-phenyl)-propionic acid
136. 3-(4-Chloro-phenyl)-3-(cyclopentylmethyl-{4-[3-(2,5-dioxo-pyrrolidin-1-yl)-propyl]-3-methoxy-benzyl}-amino)-propionic acid
137. 3-(4-Chloro-phenyl)-3-({4-[3-(2,5-dioxo-pyrrolidin-1-yl)-propyl]-3-methyl-benzyl}-isobutyl-amino)-propionic acid
138. 3-(4-Chloro-phenyl)-3-(cyclobutyl-{4-[3-(2,5-dioxo-pyrrolidin-1-yl)-propyl]-3-methoxy-benzyl}-amino)-propionic acid
139. 3-(Cyclopentylmethyl-{4-[3-(2,5-dioxo-pyrrolidin-1-yl)-propyl]-3-methoxy-benzyl}-amino)-3-(2,3-dihydro-benzofuran-5-yl)-propionic acid 140. 3-(Butyl-{4-[3-(2,5-dioxo-pyrrolidin-1-yl)-propyl]-3-methoxy-benzyl}-amino)-3-(2,3-dihydro-benzofuran-5-yl)-propionic acid
141. 3-(2,3-Dihydro-benzofuran-5-yl)-3-({4-[3-(2,5-dioxo-pyrrolidin-1-yl)-propyl]-3-methoxy-benzyl}-isobutyl-amino)-propionic acid
142. 3-(Cyclopropylmethyl-{4-[3-(2,5-dioxo-pyrrolidin-1-yl)-propyl]-3-methyl-benzyl}-amino)-3-(2,3-dihydro-benzofuran-5-yl)-propionic acid
143. 3-(Cyclohexylmethyl-{4-[3-(2,5-dioxo-pyrrolidin-1-yl)-propyl]-3-methyl-benzyl}-amino)-3-(2,3-dihydro-benzofuran-5-yl)-propionic acid
144. 3-(2,3-Dihydro-benzofuran-5-yl)-3-({4-[2-(2,5-dioxo-pyrrolidin-1-yl)-ethoxy]-3-methyl-benzyl}-isobutyl-amino)-propionic acid
145. 3-(Butyl-{4-[2-(2,5-dioxo-pyrrolidin-1-yl)-ethoxy]-3-methyl-benzyl}-amino)-3-(2,3-dihydro-benzofuran-5-yl)-propionic acid
146. 3-(Cyclopentylmethyl-{4-[2-(2,5-dioxo-pyrrolidin-1-yl)-ethoxy]-3-methoxy-benzyl}-amino)-3-(2,3-dihydro-benzofuran-5-yl)-propionic acid
147. 3-(Cyclopentylmethyl-{4-[2-(2,5-dioxo-pyrrolidin-1-yl)-ethoxy]-3-methyl-benzyl}-amino)-3-(2,3-dihydro-benzofuran-5-yl)-propionic acid
148. 3-(Cyclohexylmethyl-{4-[2-(2,5-dioxo-pyrrolidin-1-yl)-ethoxy]-3-methoxy-benzyl}-amino)-3-(2,3-dihydro-benzofuran-5-yl)-propionic acid
149. 3-(Cyclohexylmethyl-{4-[2-(2,5-dioxo-pyrrolidin-1-yl)-ethoxy]-3-methyl-benzyl}-amino)-3-(2,3-dihydro-benzofuran-5-yl)-propionic acid
150. 3-(Butyl-{4-[2-(2,5-dioxo-pyrrolidin-1-yl)-ethoxy]-3-methoxy-benzyl}-amino)-3-(2,4-dichloro-phenyl)-propionic acid
151. 3-(2,4-Dichloro-phenyl)-3-({4-[2-(2,5-dioxo-pyrrolidin-1-yl)-ethoxy]-3-methoxy-benzyl}-isobutyl-amino)-propionic acid
152. 3-(4-Chloro-phenyl)-3-({3-methoxy-4-[2-(3-methyl-2,6-dioxo-3,6-dihydro-2H-pyrimidin-1-yl)-ethoxy]-benzyl}-methyl-amino)-2-methyl-propionic acid
153. 3-(4-Chloro-phenyl)-3-(ethyl-{3-methoxy-4-[2-(3-methyl-2,6-dioxo-3,6-dihydro-2H-pyrimidin-1-yl)-ethoxy]-benzyl}-amino)-2-methyl-propionic acid
154. 3-(2,3-Dihydro-benzofuran-5-yl)-3-(ethyl-{3-methyl-4-[2-(3-methyl-2,6-dioxo-3,6-dihydro-2H-pyrimidin-1-yl)-ethoxy]-benzyl}-amino)-propionic acid
155. 3-(2,3-Dihydro-benzofuran-5-yl)-3-({3-methyl-4-[2-(3-methyl-2,6-dioxo-3,6-dihydro-2H-pyrimidin-1-yl)-ethoxy]-benzyl}-propyl-amino)-propionic acid
156. 3-(Cyclopropylmethyl-{3-methoxy-4-[2-(3-methyl-2,6-dioxo-3,6-dihydro-2H-pyrimidin-1-yl)-ethoxy]-benzyl}-amino)-3-(2,4-dichloro-phenyl)-propionic acid
157. 3-(4-Chloro-phenyl)-3-[{4-[2-(2,5-dioxo-pyrrolidin-1-yl)-ethoxy]-3-methyl-benzyl}-(3,3,3-trifluoro-propyl)-amino]-propionic acid
158. 3-(2,3-Dihydro-benzofuran-5-yl)-3-(isobutyl-{3-methyl-4-[2-(3-methyl-2,6-dioxo-3,6-dihydro-2H-pyrimidin-1-yl)-ethoxy]-benzyl}-amino)-propionic acid
159. 3-(2,4-Dichloro-phenyl)-3-({3-methoxy-4-[2-(3-methyl-2,6-dioxo-3,6-dihydro-2H-pyrimidin-1-yl)-ethoxy]-benzyl}-propyl-amino)-propionic acid
160. 3-(Cyclopentylmethyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
161. 3-(Butyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
162. 3-(2,4-Dichloro-phenyl)-3-({4-[2-(2,5-dioxo-pyrrolidin-1-yl)-ethoxy]-3-methyl-benzyl}-isobutyl-amino)-propionic acid
163. 3-(Cyclopropylmethyl-{4-[2-(2,5-dioxo-pyrrolidin-1-yl)-ethoxy]-3-methyl-benzyl}-amino)-3-(2,4-dichloro-phenyl)-propionic acid
164. 3-(Butyl-{4-[2-(2,5-dioxo-pyrrolidin-1-yl)-ethoxy]-3-methyl-benzyl}-amino)-3-(2,4-dichloro-phenyl)-propionic acid
165. 3-(4-Chloro-phenyl)-3-[{4-[2-(2,5-dioxo-pyrrolidin-1-yl)-ethoxy]-3-methoxy-benzyl}-(4-fluoro-benzyl)-amino]-propionic acid; hydrochloride
166. 3-(4-Chloro-phenyl)-3-[{4-[2-(2,5-dioxo-pyrrolidin-1-yl)-ethoxy]-3-methyl-benzyl}-(4-fluoro-benzyl)-amino]-propionic acid; hydrochloride
167. 3-(3,4-Dichloro-phenyl)-3-[{4-[2-(2,5-dioxo-pyrrolidin-1-yl)-ethoxy]-3-methyl-benzyl}-(3,3,3-trifluoro-propyl)-amino]-propionic acid
168. 1-(Butyl-{4-[2-(2,5-dioxo-pyrrolidin-1-yl)-ethoxy]-3-methoxy-benzyl}-amino)-5-chloro-indan-2-carboxylic acid
169. 5-Chloro-1-(cyclohexylmethyl-{4-[2-(2,5-dioxo-pyrrolidin-1-yl)-ethoxy]-3-methoxy-benzyl}-amino)-indan-2-carboxylic acid
170. 5-Chloro-1-({4-[2-(2,5-dioxo-pyrrolidin-1-yl)-ethoxy]-3-methoxy-benzyl}-isobutyl-amino)-indan-2-carboxylic acid
171. 5-Chloro-1-(cyclopentylmethyl-{4-[2-(2,5-dioxo-pyrrolidin-1-yl)-ethoxy]-3-methoxy-benzyl}-amino)-indan-2-carboxylic acid
172. 5-Chloro-1-({4-[2-(2,5-dioxo-pyrrolidin-1-yl)-ethoxy]-3-methyl-benzyl}-propyl-amino)-indan-2-carboxylic acid
173. 1-(Butyl-{4-[2-(2,5-dioxo-pyrrolidin-1-yl)-ethoxy]-3-methyl-benzyl}-amino)-5-chloro-indan-2-carboxylic acid
174. 5-Chloro-1-({4-[2-(2,5-dioxo-pyrrolidin-1-yl)-ethoxy]-3-methyl-benzyl}-isobutyl-amino)-indan-2-carboxylic acid
175. 3-(4-Chloro-phenyl)-3-({4-[2-(2,5-dioxo-pyrrolidin-1-yl)-ethoxy]-3-methyl-benzyl}-ethyl-amino)-2-methyl-propionic acid
176. 3-(4-Chloro-phenyl)-3-({4-[2-(2,5-dioxo-pyrrolidin-1-yl)-ethoxy]-3-methyl-benzyl}-ethyl-amino)-2-methyl-propionic acid
177. 3-(Butyl-{4-[3-(2,5-dioxo-pyrrolidin-1-yl)-propyl]-3-methyl-benzyl}-amino)-3-(2,3-dihydro-benzofuran-5-yl)-propionic acid
178. 3-({4-[2-(2,5-Dioxo-pyrrolidin-1-yl)-ethoxy]-3-methyl-benzyl}-propyl-amino)-3-p-tolyl-propionic acid
179. 3-(Cyclopentylmethyl-{4-[2-(2,5-dioxo-pyrrolidin-1-yl)-ethoxy]-3-methoxy-benzyl}-amino)-3-p-tolyl-propionic acid
180. 3-(Cyclopentylmethyl-{4-[2-(2,5-dioxo-pyrrolidin-1-yl)-ethoxy]-3-methoxy-benzyl}-amino)-3-(4-trifluoromethyl-phenyl)-propionic acid
181. 3-(Cyclohexylmethyl-{4-[2-(2,5-dioxo-pyrrolidin-1-yl)-ethoxy]-3-methoxy-benzyl}-amino)-3-(4-trifluoromethyl-phenyl)-propionic acid
182. (4-Chloro-phenyl)-({4-[2-(2,5-dioxo-pyrrolidin-1-yl)-ethoxy]-3-methoxy-benzyl}-ethyl-amino)-acetic acid
183. (4-Chloro-phenyl)-({4-[2-(2,5-dioxo-pyrrolidin-1-yl)-ethoxy]-3-methoxy-benzyl}-propyl-amino)-acetic acid
184. Butyl-{4-[2-(2,5-dioxo-pyrrolidin-1-yl)-ethoxy]-3-methoxy-benzyl}-amino)-(4-chloro-phenyl)-acetic acid
185. (4-Chloro-phenyl)-(cyclopentylmethyl-{4-[2-(2,5-dioxo-pyrrolidin-1-yl)-ethoxy]-3-methoxy-benzyl}-amino)-acetic acid 186. 3-(4-Chloro-phenyl)-3-({4-[2-(2,5-dioxo-pyrrolidin-1-yl)-ethoxy]-3-methoxy-benzyl}-propyl-amino)-2-methyl-propionic acid
187. 3-(4-Chloro-phenyl)-3-(cyclopropylmethyl-{4-[2-(2,5-dioxo-pyrrolidin-1-yl)-ethoxy]-3-methoxy-benzyl}-amino)-2-methyl-propionic acid
188. 3-(4-Chloro-phenyl)-3-(cyclopentylmethyl-{4-[2-(2,5-dioxo-pyrrolidin-1-yl)-ethylsulfanyl]-3-methoxy-benzyl}-amino)-propionic acid
189. 3-(4-Chloro-3-fluoro-phenyl)-3-(cyclopropylmethyl-{4-[2-(2,5-dioxo-pyrrolidin-1-yl)-ethylsulfanyl]-3-methoxy-benzyl}-amino)-propionic acid
190. 3-(4-Chloro-3-fluoro-phenyl)-3-(cyclopentylmethyl-{4-[2-(2,5-dioxo-pyrrolidin-1-yl)-ethylsulfanyl]-3-methoxy-benzyl}-amino)-propionic acid
191. 3-(Cyclopropylmethyl-{4-[2-(2,5-dioxo-pyrrolidin-1-yl)-ethylsulfanyl]-3-methoxy-benzyl}-amino)-3-(3,4-dichloro-phenyl)-propionic acid
192. 3-(3,4-Dichloro-phenyl)-3-({4-[2-(2,5-dioxo-pyrrolidin-1-yl)-ethylsulfanyl]-3-methoxy-benzyl}-propyl-amino)-propionic acid
193. 3-(3,4-Dichloro-phenyl)-3-({4-[2-(2,5-dioxo-pyrrolidin-1-yl)-ethylsulfanyl]-3-methoxy-benzyl}-isobutyl-amino)-propionic acid
194. 3-(4-Chloro-phenyl)-3-({4-[2-(2,5-dioxo-pyrrolidin-1-yl)-ethoxy]-3-methyl-benzyl}-propyl-amino)-2-methyl-propionic acid
195. 3-(4-Chloro-phenyl)-3-({4-[2-(2,5-dioxo-pyrrolidin-1-yl)-ethoxy]-3-fluoro-benzyl}-propyl-amino)-2-methyl-propionic acid
196. 1-[(4-Chloro-phenyl)-({4-[2-(2,5-dioxo-pyrrolidin-1-yl)-ethoxy]-3-ethyl-benzyl}-propyl-amino)-methyl]-cyclopropanecarboxylic acid
197. 3-(4-Chloro-phenyl)-3-({4-[2-(2,5-dioxo-pyrrolidin-1-yl)-ethoxy]-3-methoxy-benzyl}-ethyl-amino)-2,2-dimethyl-propionic acid
198. (S)-3-(Cyclohexylmethyl-{3-methoxy-4-[2-(3-methyl-2,5-dioxo-imidazolidin-1-yl)-ethoxy]-benzyl}-amino)-3-(3,4-dichloro-phenyl)-propionic acid; hydrochloride
199. (S)-3-(4-Chloro-phenyl)-3-(cyclopentylmethyl-{3-methyl-4-[2-(3-methyl-2,5-dioxo-imidazolidin-1-yl)-ethoxy]-benzyl}-amino)-propionic acid
200. (S)-3-(Cyclopentylmethyl-{3-methyl-4-[2-(3-methyl-2,5-dioxo-imidazolidin-1-yl)-ethoxy]-benzyl}-amino)-3-(3,4-dichloro-phenyl)-propionic acid; hydrochloride
201. (R)-3-({3-Chloro-4-[2-(3-methyl-2,5-dioxo-imidazolidin-1-yl)-ethoxy]-benzyl}-cyclopentylmethyl-amino)-3-(4-chloro-phenyl)-propionic acid
202. (R)-3-({3-Chloro-4-[2-(3-methyl-2,5-dioxo-imidazolidin-1-yl)-ethoxy]-benzyl}-cyclohexylmethyl-amino)-3-(4-chloro-phenyl)-propionic acid
203. 3-(5-Chloro-thiophen-2-yl)-3-({4-[2-(2,5-dioxo-pyrrolidin-1-yl)-ethoxy]-3-methyl-benzyl}-propyl-amino)-propionic acid
204. 3-(2,5-Dimethyl-thiophen-3-yl)-3-({4-[2-(2,5-dioxo-pyrrolidin-1-yl)-ethoxy]-3-methoxy-benzyl}-propyl-amino)-propionic acid; hydrochloride or a pharmaceutically acceptable salt thereof or stereoisomer thereof or a pharmaceutically acceptable salt of the stereoisomer.

A particular group of the compounds of the present invention represented by formula 1 include compounds selected from the group consisting of:

1. 3-(2,3-Dihydro-benzofuran-5-yl)-3-({4-[2-(2,5-dioxo-pyrrolidin-1-yl)-ethoxy]-3-methoxy-benzyl}-isobutyl-amino)-propionic acid
2. 3-(4-Chloro-phenyl)-3-({4-[2-(2,5-dioxo-pyrrolidin-1-yl)-ethoxy]-3-methoxy-benzyl}-isobutyl-amino)-propionic acid
3. (S)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid
4. (S)-3-(4-Chloro-phenyl)-3-({4-[2-(2,5-dioxo-pyrrolidin-1-yl)-ethoxy]-3-methyl-benzyl}-propyl-amino)-propionic acid
5. (S)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid; hydrochloride
6. (S)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid; hydrochloride
7. (S)-3-({3-Chloro-4-[2-(2,5-dioxo-pyrrolidin-1-yl)-ethoxy]-benzyl}-cyclopropyl-ethyl-amino)-3-(4-chloro-3-fluoro-phenyl)-propionic acid; hydrochloride
8. (S)-3-(4-Chloro-3-fluoro-phenyl)-3-(cyclopentylmethyl-{4-[2-(2,5-dioxo-pyrrolidin-1-yl)-ethoxy]-3-methoxy-benzyl}-amino)-propionic acid
9. (S)-3-(4-Chloro-3-fluoro-phenyl)-3-(cyclopropylmethyl-{4-[2-(2,5-dioxo-pyrrolidin-1-yl)-ethoxy]-3-fluoro-benzyl}-amino)-propionic acid; hydrochloride
10. (S)-3-(4-Chloro-phenyl)-3-(cyclopropylmethyl-{4-[2-(2,5-dioxo-pyrrolidin-1-yl)-ethoxy]-3-methyl-benzyl}-amino)-propionic acid
11. (S)-3-(4-Chloro-3-fluoro-phenyl)-3-({4-[2-(2,5-dioxo-pyrrolidin-1-yl)-ethoxy]-3-methyl-benzyl}-isobutyl-amino)-propionic acid; hydrochloride
12. (S)-3-(Cyclopropylmethyl-{4-[2-(2,5-dioxo-pyrrolidin-1-yl)-ethoxy]-3-methyl-benzyl}-amino)-3-(3,4-dichloro-phenyl)-propionic acid
13. (R)-3-(4-Chloro-phenyl)-3-(cyclopentylmethyl-{4-[2-(2,5-dioxo-pyrrolidin-1-yl)-ethoxy]-3-ethyl-benzyl}-amino)-propionic acid
14. 3-(4-Chloro-phenyl)-3-(cyclopropylmethyl-{4-[2-(2,5-dioxo-pyrrolidin-1-yl)-ethoxy]-3-methoxy-benzyl}-amino)-propionic acid
15. 3-(4-Chloro-phenyl)-3-({4-[2-(2,5-dioxo-pyrrolidin-1-yl)-ethoxy]-3-methoxy-benzyl}-propyl-amino)-propionic acid
16. 3-(Butyl-{4-[2-(2,5-dioxo-pyrrolidin-1-yl)-ethoxy]-3-methoxy-benzyl}-amino)-3-(4-chloro-phenyl)-propionic acid
17. 3-(4-Chloro-phenyl)-3-(cyclohexylmethyl-{4-[2-(2,5-dioxo-pyrrolidin-1-yl)-ethoxy]-3-methoxy-benzyl}-amino)-propionic acid
18. 3-(Butyl-{4-[2-(2,5-dioxo-pyrrolidin-1-yl)-ethoxy]-3-methoxy-benzyl}-amino)-3-(4-chloro-3-fluoro-phenyl)-propionic acid
19. 3-(4-Chloro-3-fluoro-phenyl)-3-(cyclohexylmethyl-{4-[2-(2,5-dioxo-pyrrolidin-1-yl)-ethoxy]-3-methoxy-benzyl}-amino)-propionic acid
20. 3-(4-Chloro-phenyl)-3-(cyclopentylmethyl-{4-[2-(2,5-dioxo-pyrrolidin-1-yl)-ethoxy]-3-fluoro-benzyl}-amino)-propionic acid
21. 3-(4-Chloro-phenyl)-3-({4-[2-(2,5-dioxo-pyrrolidin-1-yl)-ethoxy]-3-methyl-benzyl}-isobutyl-amino)-propionic acid
22. 3-(4-Chloro-phenyl)-3-(cyclopentylmethyl-{4-[2-(2,5-dioxo-pyrrolidin-1-yl)-ethoxy]-3-methyl-benzyl}-amino)-propionic acid
23. 3-(4-Chloro-3-fluoro-phenyl)-3-(cyclopropylmethyl-{4-[2-(2,5-dioxo-pyrrolidin-1-yl)-ethoxy]-3-methyl-benzyl}-amino)-propionic acid 24. 3-(4-Chloro-3-fluoro-phenyl)-3-({4-[2-(2,5-dioxo-pyrrolidin-1-yl)-ethoxy]-3-methyl-benzyl}-propyl-amino)-propionic acid
25. 3-(Butyl-{4-[2-(2,5-dioxo-pyrrolidin-1-yl)-ethoxy]-3-methyl-benzyl}-amino)-3-(4-chloro-3-fluoro-phenyl)-propionic acid
26. 3-(4-Chloro-phenyl)-3-(cyclopropylmethyl-{4-[2-(2,5-dioxo-pyrrolidin-1-yl)-ethoxy]-3-ethyl-benzyl}-amino)-propionic acid
27. 3-(4-Chloro-phenyl)-3-({4-[2-(2,5-dioxo-pyrrolidin-1-yl)-ethoxy]-3-ethyl-benzyl}-isobutyl-amino)-propionic acid
28. 3-(Butyl-{4-[2-(2,5-dioxo-pyrrolidin-1-yl)-ethoxy]-3-ethyl-benzyl}-amino)-3-(4-chloro-phenyl)-propionic acid
29. 3-(4-Chloro-phenyl)-3-(cyclohexylmethyl-{4-[2-(2,5-dioxo-pyrrolidin-1-yl)-ethoxy]-3-ethyl-benzyl}-amino)-propionic acid
30. 3-(4-Chloro-3-fluoro-phenyl)-3-(cyclopropylmethyl-{4-[2-(2,5-dioxo-pyrrolidin-1-yl)-ethoxy]-3-ethyl-benzyl}-amino)-propionic acid
31. 3-(4-Chloro-3-fluoro-phenyl)-3-({4-[2-(2,5-dioxo-pyrrolidin-1-yl)-ethoxy]-3-ethyl-benzyl}-propyl-amino)-propionic acid
32. 3-(Cyclopropylmethyl-{3-methoxy-4-[2-(3-methyl-2,6-dioxo-3,6-dihydro-2H-pyrimidin-1-yl)-ethoxy]-benzyl}-amino)-3-(3,4-dichloro-phenyl)-propionic acid
33. 3-(Cyclopentylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
34. 3-(Cyclopropylmethyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid
35. 3-(Cyclopentylmethyl-{4-[3-(2,5-dioxo-pyrrolidin-1-yl)-propyl]-3-methoxy-benzyl}-amino)-3-(2,3-dihydro-benzofuran-5-yl)-propionic acid
36. 3-(Butyl-{4-[3-(2,5-dioxo-pyrrolidin-1-yl)-propyl]-3-methoxy-benzyl}-amino)-3-(2,3-dihydro-benzofuran-5-yl)-propionic acid
37. 3-(2,3-Dihydro-benzofuran-5-yl)-3-({4-[3-(2,5-dioxo-pyrrolidin-1-yl)-propyl]-3-methoxy-benzyl}-isobutyl-amino)-propionic acid
38. 3-(Butyl-{4-[2-(2,5-dioxo-pyrrolidin-1-yl)-ethoxy]-3-methyl-benzyl}-amino)-3-(2,3-dihydro-benzofuran-5-yl)-propionic acid
39. 3-(Cyclopentylmethyl-{4-[2-(2,5-dioxo-pyrrolidin-1-yl)-ethoxy]-3-methoxy-benzyl}-amino)-3-(2,3-dihydro-benzofuran-5-yl)-propionic acid
40. 3-(Cyclopentylmethyl-{4-[2-(2,5-dioxo-pyrrolidin-1-yl)-ethoxy]-3-methyl-benzyl}-amino)-3-(2,3-dihydro-benzofuran-5-yl)-propionic acid
41. 3-(Cyclohexylmethyl-{4-[2-(2,5-dioxo-pyrrolidin-1-yl)-ethoxy]-3-methoxy-benzyl}-amino)-3-(2,3-dihydro-benzofuran-5-yl)-propionic acid
42. 3-(2,3-Dihydro-benzofuran-5-yl)-3-(ethyl-{3-methyl-4-[2-(3-methyl-2,6-dioxo-3,6-dihydro-2H-pyrimidin-1-yl)-ethoxy]-benzyl}-amino)-propionic acid
43. 3-(4-Chloro-phenyl)-3-(cyclopentylmethyl-{4-[2-(2,5-dioxo-pyrrolidin-1-yl)-ethylsulfanyl]-3-methoxy-benzyl}-amino)-propionic acid
44. 3-(4-Chloro-3-fluoro-phenyl)-3-(cyclopropylmethyl-{4-[2-(2,5-dioxo-pyrrolidin-1-yl)-ethylsulfanyl]-3-methoxy-benzyl}-amino)-propionic acid
45. 3-(Cyclopropylmethyl-{4-[2-(2,5-dioxo-pyrrolidin-1-yl)-ethylsulfanyl]-3-methoxy-benzyl}-amino)-3-(3,4-dichloro-phenyl)-propionic acid or a pharmaceutically acceptable salt thereof or stereoisomer thereof or a pharmaceutically acceptable salt of the stereoisomer.

A further embodiment of the invention includes compounds of formula 2

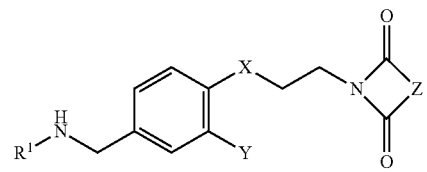

wherein $R^1$ represents a group selected from the group consisting of;

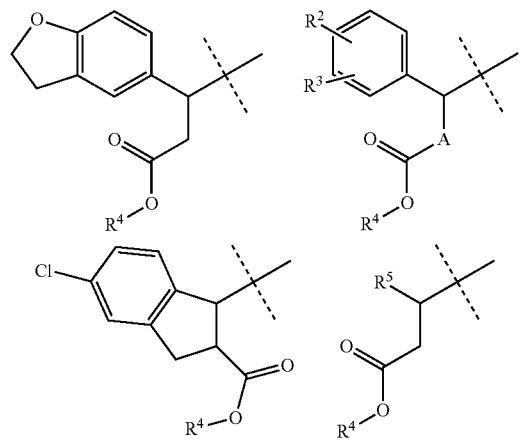

wherein

A represents a direct bond or, $CH_2$, $CH(CH_3)$, $C(CH_3)_2$ or $C(CH_2)_2$ group;

$R_2$ represents Cl, Me or $CF_3$;

$R_3$ represents H, Cl, or F;

$R_4$ represents Me or Et group;

$R_5$ represents heteroaryl group selected from the group existing of

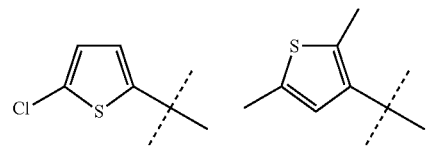

X represents O, S or $CH_2$ group;

Y represents halogen, $C_{1-4}$ alkyl, or $C_{1-4}$ alkoxy group;

Z represents $(CH_2)_2$, $CH_2N(CH_3)$ or $CH=CH-N(CH_3)$ group;

or a salt thereof.

The intermediates of general formula 2 listed in Table 1 are prepared.

TABLE 1

| Example | Structure | Chemical name |
|---|---|---|
| 2.1. | 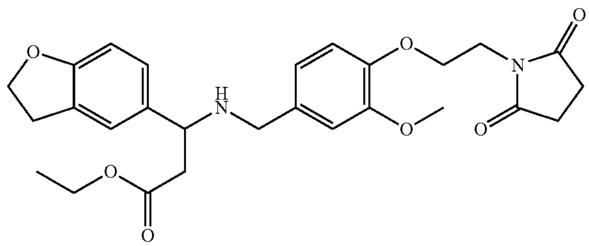 [SMILES: CCOC(=O)CC(NCc1ccc(OCCN2C(=O)CCC2=O)c(OC)c1)c1ccc2c(c1)CCO2] | 3-(2,3-Dihydro-benzofuran-5-yl)-3-{4-[2-(2,5-dioxo-pyrrolidin-1-yl)-ethoxy]-3-methoxy-benzylamino}-propionic acid ethyl ester |
| 2.2. | 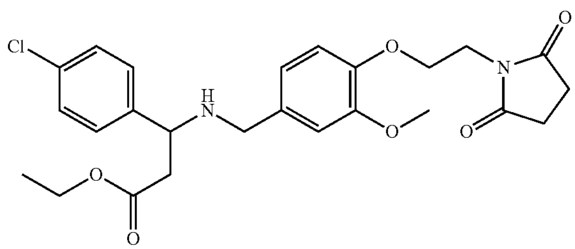 [SMILES: CCOC(=O)CC(NCc1ccc(OCCN2C(=O)CCC2=O)c(OC)c1)c1ccc(Cl)cc1] | 3-(4-Chloro-phenyl)-3-{4-[2-(2,5-dioxo-pyrrolidin-1-yl)-ethoxy]-3-methoxy-benzylamino}-propionic acid ethyl ester |
| 2.3. | 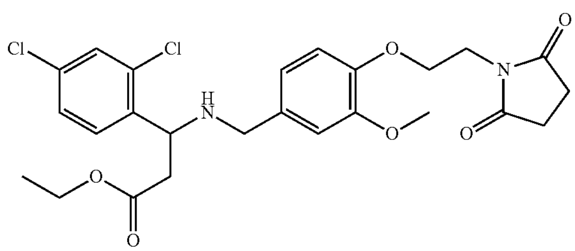 [SMILES: CCOC(=O)CC(NCc1ccc(OCCN2C(=O)CCC2=O)c(OC)c1)c1ccc(Cl)cc1Cl] | 3-(2,4-Dichloro-phenyl)-3-{4-[2-(2,5-dioxo-pyrrolidin-1-yl)-ethoxy]-3-methoxy-benzylamino}-propionic acid ethyl ester |
| 2.4. | 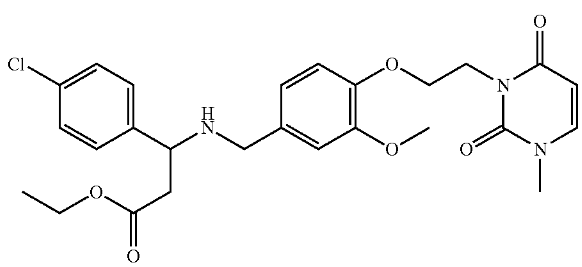 [SMILES: CCOC(=O)CC(NCc1ccc(OCCn2c(=O)ccn(C)c2=O)c(OC)c1)c1ccc(Cl)cc1] | 3-(4-Chloro-phenyl)-3-{3-methoxy-4-[2-(3-methyl-2,6-dioxo-3,6-dihydro-2H-pyrimidin-1-yl)-ethoxy]-benzylamino}-propionic acid ethyl ester |
| 2.5. | 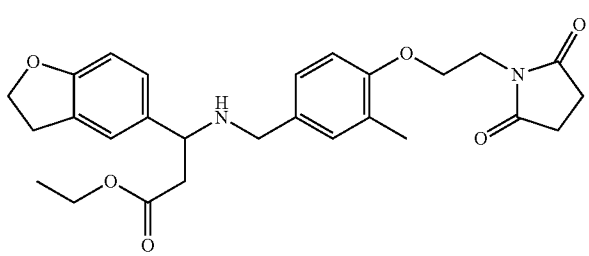 [SMILES: CCOC(=O)CC(NCc1ccc(OCCN2C(=O)CCC2=O)c(C)c1)c1ccc2c(c1)CCO2] | 3-(2,3-Dihydro-benzofuran-5-yl)-3-{4-[2-(2,5-dioxo-pyrrolidin-1-yl)-ethoxy]-3-methyl-benzylamino}-propionic acid ethyl ester |
| 2.6. | 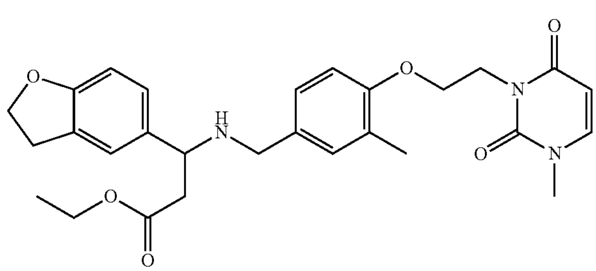 [SMILES: CCOC(=O)CC(NCc1ccc(OCCn2c(=O)ccn(C)c2=O)c(C)c1)c1ccc2c(c1)CCO2] | 3-(2,3-Dihydro-benzofuran-5-yl)-3-{3-methyl-4-[2-(3-methyl-2,6-dioxo-3,6-dihydro-2H-pyrimidin-1-yl)-ethoxy]-benzylamino}-propionic acid ethyl ester |

TABLE 1-continued

| Example | Structure | Chemical name |
|---|---|---|
| 2.7. | 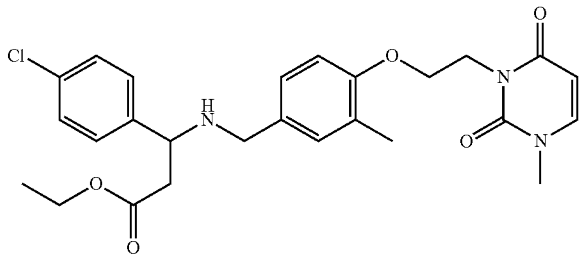 [SMILES: CCOC(=O)CC(NCc1ccc(OCCn2c(=O)ccn(C)c2=O)c(C)c1)c1ccc(Cl)cc1] | 3-(4-Chloro-phenyl)-3-{3-methyl-4-[2-(3-methyl-2,6-dioxo-3,6-dihydro-2H-pyrimidin-1-yl)-ethoxy]-benzylamino}-propionic acid ethyl ester |
| 2.8. | 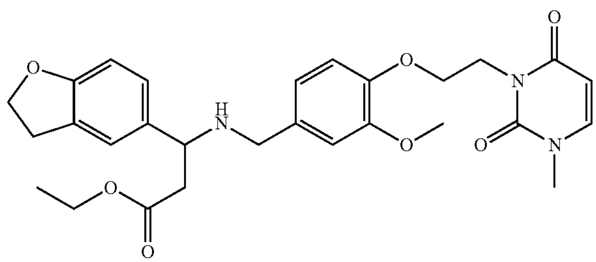 [SMILES: CCOC(=O)CC(NCc1ccc(OCCn2c(=O)ccn(C)c2=O)c(OC)c1)c1ccc2c(c1)CCO2] | 3-(2,3-Dihydro-benzofuran-5-yl)-3-{3-methoxy-4-[2-(3-methyl-2,6-dioxo-3,6-dihydro-2H-pyrimidin-1-yl)-ethoxy]-benzylamino}-propionic acid ethyl ester |
| 2.9. | 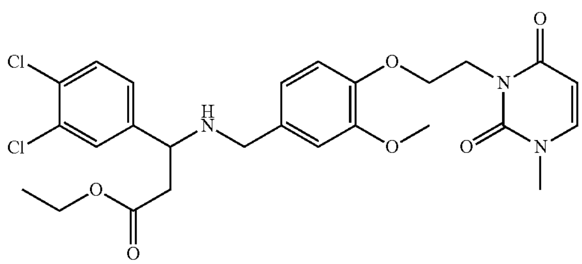 [SMILES: CCOC(=O)CC(NCc1ccc(OCCn2c(=O)ccn(C)c2=O)c(OC)c1)c1ccc(Cl)c(Cl)c1] | 3-(3,4-Dichloro-phenyl)-3-{3-methoxy-4-[2-(3-methyl-2,6-dioxo-3,6-dihydro-2H-pyrimidin-1-yl)-ethoxy]-benzylamino}-propionic acid ethyl ester |
| 2.10. | 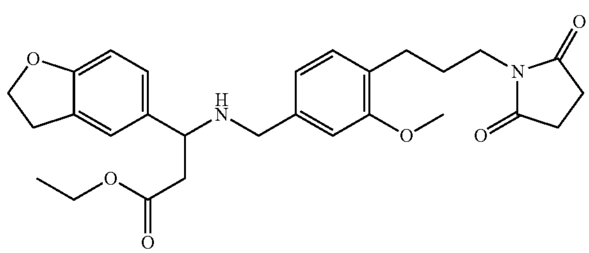 [SMILES: CCOC(=O)CC(NCc1ccc(CCCN2C(=O)CCC2=O)c(OC)c1)c1ccc2c(c1)CCO2] | 3-(2,3-Dihydro-benzofuran-5-yl)-3-{4-[3-(2,5-dioxo-pyrrolidin-1-yl)-propyl]-3-methoxy-benzylamino}-propionic acid ethyl ester |
| 2.11. | 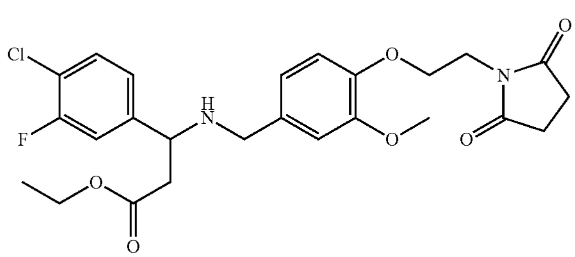 [SMILES: CCOC(=O)CC(NCc1ccc(OCCN2C(=O)CCC2=O)c(OC)c1)c1ccc(Cl)c(F)c1] | 3-(4-Chloro-3-fluoro-phenyl)-3-{4-[2-(2,5-dioxo-pyrrolidin-1-yl)-ethoxy]-3-methoxy-benzylamino}-propionic acid ethyl ester |
| 2.12. | 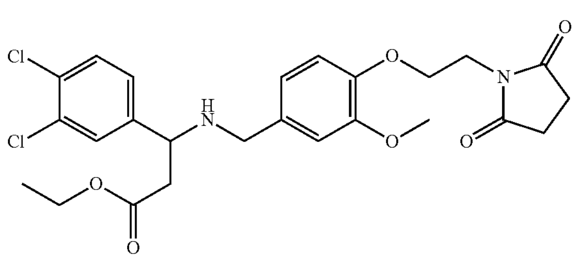 | 3-(3,4-Dichloro-phenyl)-3-{4-[2-(2,5-dioxo-pyrrolidin-1-yl)-ethoxy]-3-methoxy-benzylamino}-propionic acid ethyl ester |

TABLE 1-continued

| Example | Structure | Chemical name |
|---|---|---|
| 2.13. | 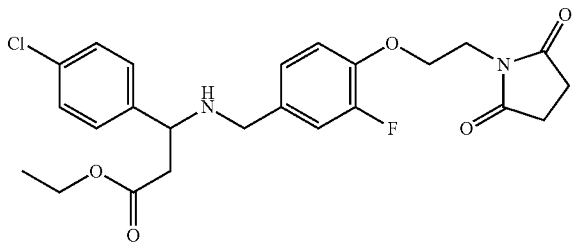 [SMILES: CCOC(=O)CC(NCc1ccc(OCCN2C(=O)CCC2=O)c(F)c1)c1ccc(Cl)cc1] | 3-(4-Chloro-phenyl)-3-{4-[2-(2,5-dioxo-pyrrolidin-1-yl)-ethoxy]-3-fluoro-benzylamino}-propionic acid ethyl ester |
| 2.14. | 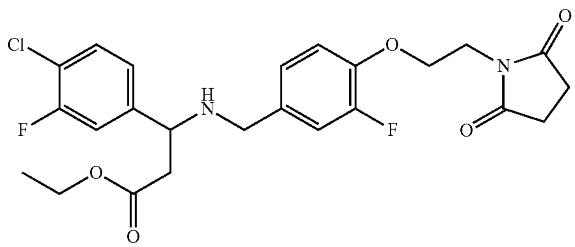 [SMILES: CCOC(=O)CC(NCc1ccc(OCCN2C(=O)CCC2=O)c(F)c1)c1ccc(Cl)c(F)c1] | 3-(4-Chloro-3-fluoro-phenyl)-3-{4-[2-(2,5-dioxo-pyrrolidin-1-yl)-ethoxy]-3-fluoro-benzylamino}-propionic acid ethyl ester |
| 2.15. | 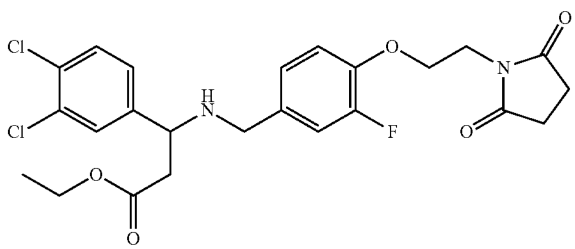 [SMILES: CCOC(=O)CC(NCc1ccc(OCCN2C(=O)CCC2=O)c(F)c1)c1ccc(Cl)c(Cl)c1] | 3-(3,4-Dichloro-phenyl)-3-{4-[2-(2,5-dioxo-pyrrolidin-1-yl)-ethoxy]-3-fluoro-benzylamino}-propionic acid ethyl ester |
| 2.16. | 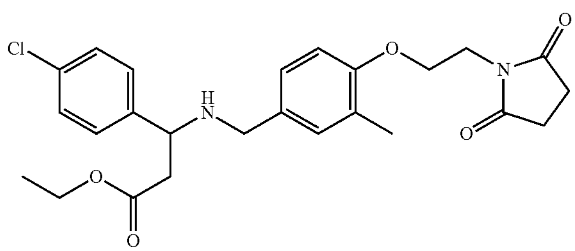 [SMILES: CCOC(=O)CC(NCc1ccc(OCCN2C(=O)CCC2=O)c(C)c1)c1ccc(Cl)cc1] | 3-(4-Chloro-phenyl)-3-{4-[2-(2,5-dioxo-pyrrolidin-1-yl)-ethoxy]-3-methyl-benzylamino}-propionic acid ethyl ester |
| 2.17. | 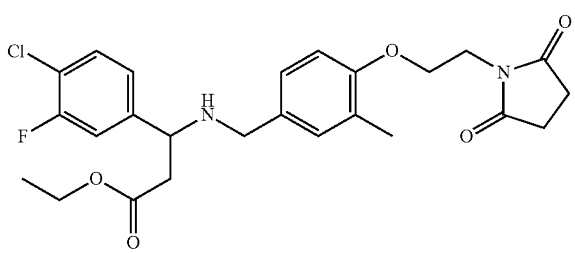 [SMILES: CCOC(=O)CC(NCc1ccc(OCCN2C(=O)CCC2=O)c(C)c1)c1ccc(Cl)c(F)c1] | 3-(4-Chloro-3-fluoro-phenyl)-3-{4-[2-(2,5-dioxo-pyrrolidin-1-yl)-ethoxy]-3-methyl-benzylamino}-propionic acid ethyl ester |
| 2.18. | 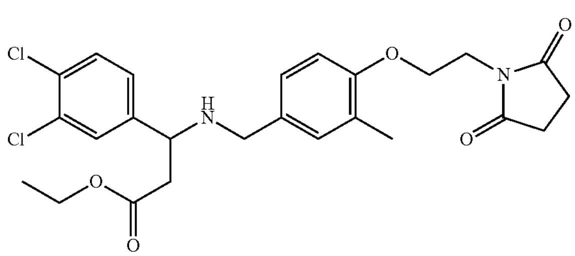 [SMILES: CCOC(=O)CC(NCc1ccc(OCCN2C(=O)CCC2=O)c(C)c1)c1ccc(Cl)c(Cl)c1] | 3-(3,4-Dichloro-phenyl)-3-{4-[2-(2,5-dioxo-pyrrolidin-1-yl)-ethoxy]-3-methyl-benzylamino}-propionic acid ethyl ester |

TABLE 1-continued

| Example | Structure | Chemical name |
|---|---|---|
| 2.19. | 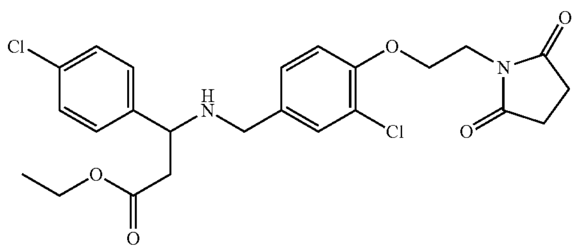 | 3-{3-Chloro-4-[2-(2,5-dioxo-pyrrolidin-1-yl)-ethoxy]-benzylamino}-3-(4-chloro-phenyl)-propionic acid ethyl ester |
| 2.20. | 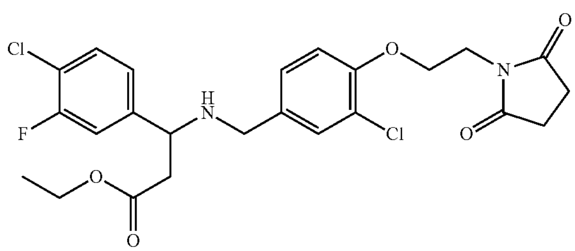 | 3-{3-Chloro-4-[2-(2,5-dioxo-pyrrolidin-1-yl)-ethoxy]-benzylamino}-3-(4-chloro-3-fluoro-phenyl)-propionic acid ethyl ester |
| 2.21. | 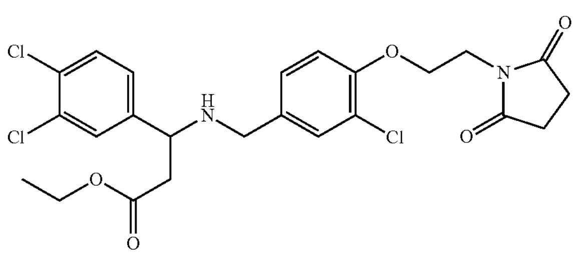 | 3-{3-Chloro-4-[2-(2,5-dioxo-pyrrolidin-1-yl)-ethoxy]-benzylamino}-3-(3,4-dichloro-phenyl)-propionic acid ethyl ester |
| 2.22. | 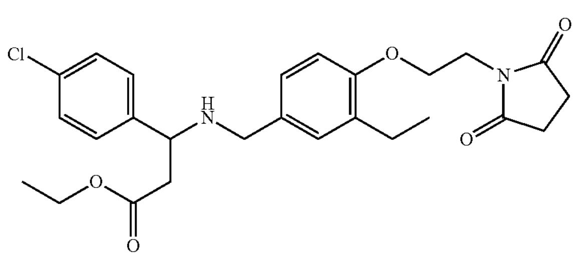 [SMILES: CCOC(=O)CC(NCc1ccc(OCCN2C(=O)CCC2=O)c(CC)c1)c1ccc(Cl)cc1] | 3-(4-Chloro-phenyl)-3-{4-[2-(2,5-dioxo-pyrrolidin-1-yl)-ethoxy]-3-ethyl-benzylamino}-propionic acid ethyl ester |
| 2.23. | 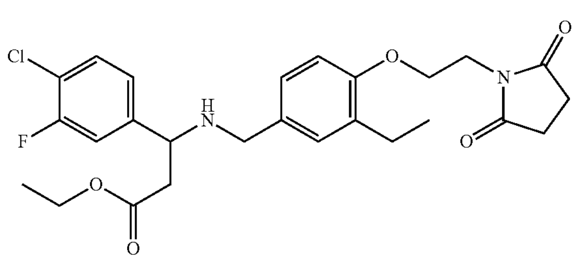 [SMILES: CCOC(=O)CC(NCc1ccc(OCCN2C(=O)CCC2=O)c(CC)c1)c1ccc(Cl)c(F)c1] | 3-(4-Chloro-3-fluoro-phenyl)-3-{4-[2-(2,5-dioxo-pyrrolidin-1-yl)-ethoxy]-3-ethyl-benzylamino}-propionic acid ethyl ester |
| 2.24. | 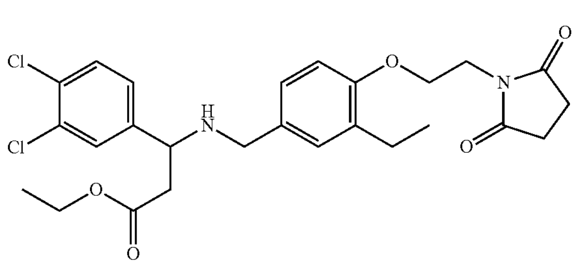 [SMILES: CCOC(=O)CC(NCc1ccc(OCCN2C(=O)CCC2=O)c(CC)c1)c1ccc(Cl)c(Cl)c1] | 3-(3,4-Dichloro-phenyl)-3-{4-[2-(2,5-dioxo-pyrrolidin-1-yl)-ethoxy]-3-ethyl-benzylamino}-propionic acid ethyl ester |

TABLE 1-continued

| Example | Structure | Chemical name |
|---------|-----------|---------------|
| 2.25. | 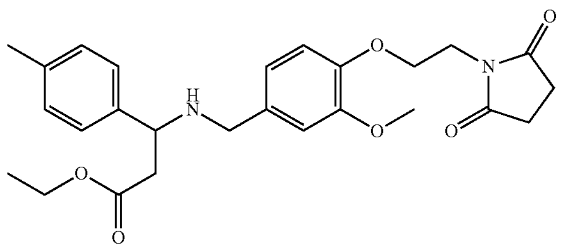 [SMILES: CCOC(=O)CC(NCc1ccc(OCCN2C(=O)CCC2=O)c(OC)c1)c1ccc(C)cc1] | 3-{4-[2-(2,5-Dioxo-pyrrolidin-1-yl)-ethoxy]-3-methyl-benzylamino}-3-p-tolyl-propionic acid ethyl ester |
| 2.26. | 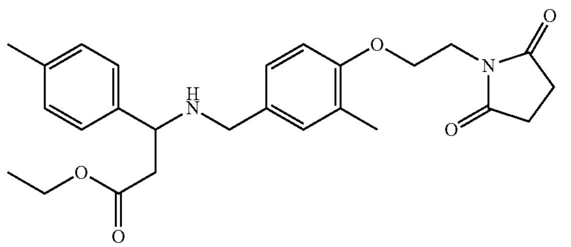 [SMILES: CCOC(=O)CC(NCc1ccc(OCCN2C(=O)CCC2=O)c(C)c1)c1ccc(C)cc1] | 3-{4-[2-(2,5-Dioxo-pyrrolidin-1-yl)-ethoxy]-3-methyl-benzylamino}-3-p-tolyl-propionic acid ethyl ester |
| 2.27. | 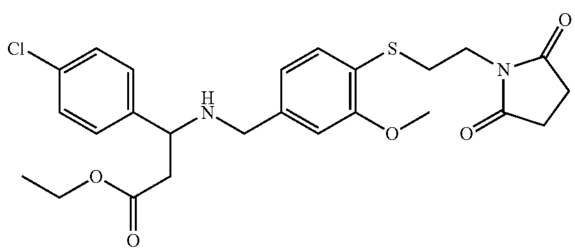 [SMILES: CCOC(=O)CC(NCc1ccc(SCCN2C(=O)CCC2=O)c(OC)c1)c1ccc(Cl)cc1] | 3-(4-Chloro-phenyl)-3-{4-[2-(2,5-dioxo-pyrrolidin-1-yl)-ethylsulfanyl]-3-methoxy-benzylamino}-propionic acid ethyl ester |
| 2.28. | 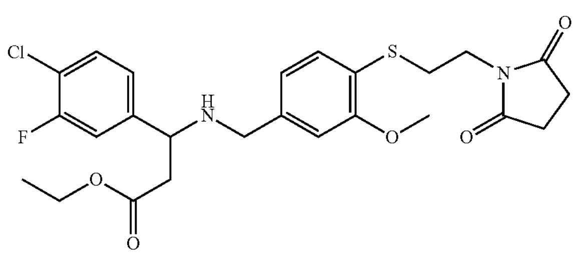 [SMILES: CCOC(=O)CC(NCc1ccc(SCCN2C(=O)CCC2=O)c(OC)c1)c1ccc(Cl)c(Cl)c1] | 3-(4-Chloro-3-fluoro-phenyl)-3-{4-[2-(2,5-dioxo-pyrrolidin-1-yl)-ethylsulfanyl]-3-methoxy-benzylamino}-propionic acid ethyl ester |
| 2.29. | 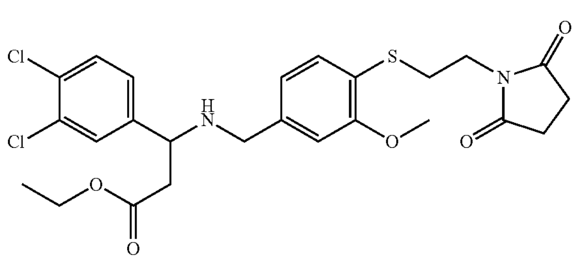 | 3-(3,4-Dichloro-phenyl)-3-{4-[2-(2,5-dioxo-pyrrolidin-1-yl)-ethylsulfanyl]-3-methoxy-benzylamino}-propionic acid ethyl ester |

General Procedures:

Starting materials and solvents used in the synthesis are obtained from chemical vendors such as ABCR, Aldrich, Acros, Apollo, Fluka, Netchem, Lancaster and others.

The crude product is purified by column chromatography or flash chromatography.

In first step the appropriate benzaldehydes (4=4a and 4b) are synthesized in different way depending on the side chain of dioxoamide derivatives. The synthesis of compound formula 4a, wherein X represents oxygen or sulphur atom is done by alkylation of 4-hydroxy- or 4-mercapto-benzaldehydes 6 with dibromoethane and dioxoamide (route via 6a, 7a) or bromo-ethyldioxoamide derivatives (route via 7) in the presence of a base, preferably $K_2CO_3$, TEA or sodium hydride using acetonitrile, DMF or MEK as solvent as described on Scheme 1.

Scheme 1

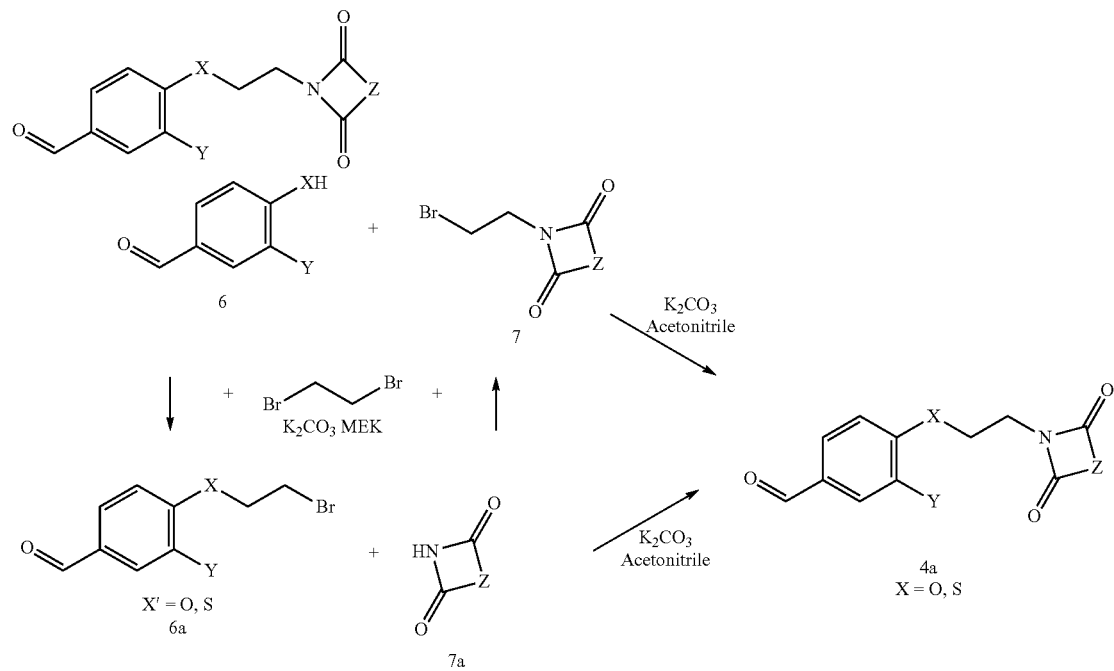

Compounds of formula 4b, wherein X represents —CH$_2$— is synthesized by two methods (Scheme 2):

1.) Appropriate aldehyde (6.1) is converted to a triflate (6.1a) then a triple-bound containing intermediate (4c), which is produced in a Sonogashira reaction (Sonogashira, K. et al. *Tetrahedron Lett.* 1975, 16 (50), 4467), is hydrogenated to saturated aldehyde (4b).

2.) Triflate (6.1a) is protected with ethyleneglycol (6.1b) and coupled in a Suzuki reaction (Suzuki, A. *Tetrahedron Lett.* 1979, 20 (36), 3437) then the formed vinyl intermediate (4d) is hydrogenated to saturated aldehyde (4b).

Scheme 2
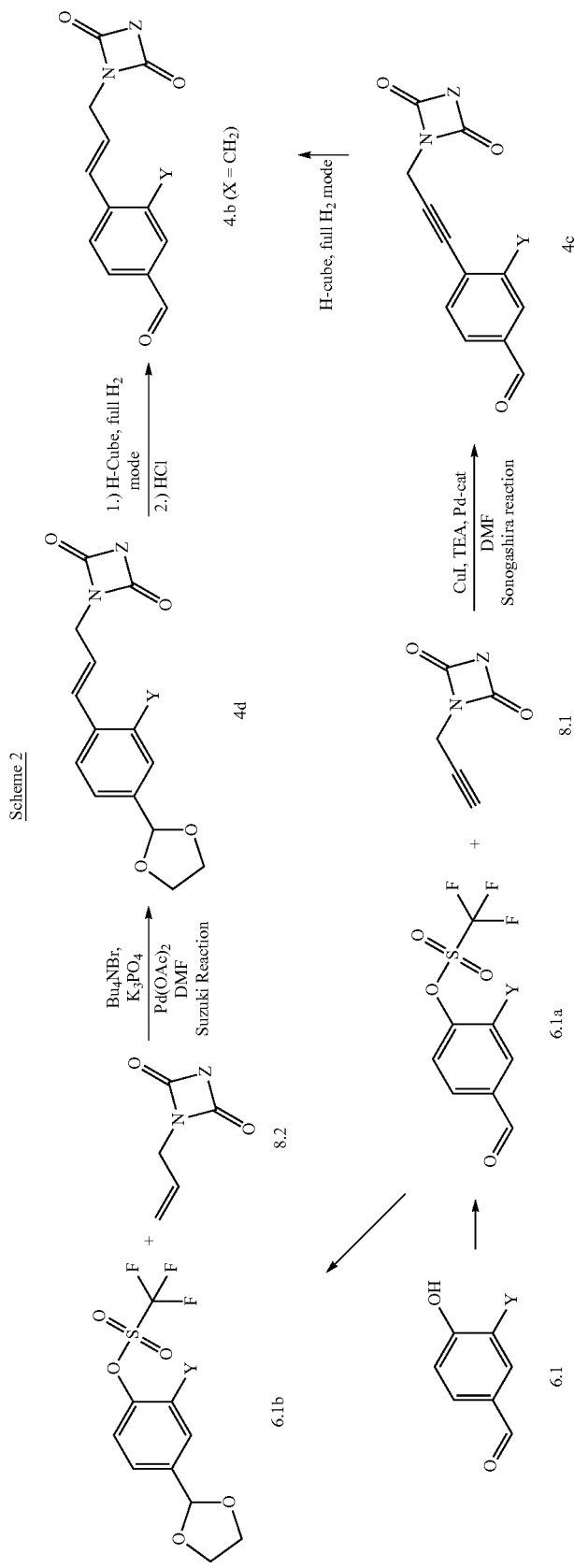

In second step synthesized benzaldehydes (4) are reacted with β-aminoacid esters or free acids (5) in mild reductive amination conditions (sodium triacetoxy borohydride in THF or 2-picoline borane complex in EtOH). The resulted secondary amines (2) are reacted with different aldehydes (3, R'=H) or cyclic ketones (3, R and R'=aliphatic ring) in reductive amination step again, the formed esters (1, R⁴=Me, Et) are hydrolyzed in acidic circumstances. The crude I (R⁴=H) is purified by chromatography, crystallization or via salt formation (Scheme 3).

The pure enantiomers of 1 are synthesized via chiral separation from racemic 1 or using chiral β-aminoacid esters or acids (5) as starting materials.

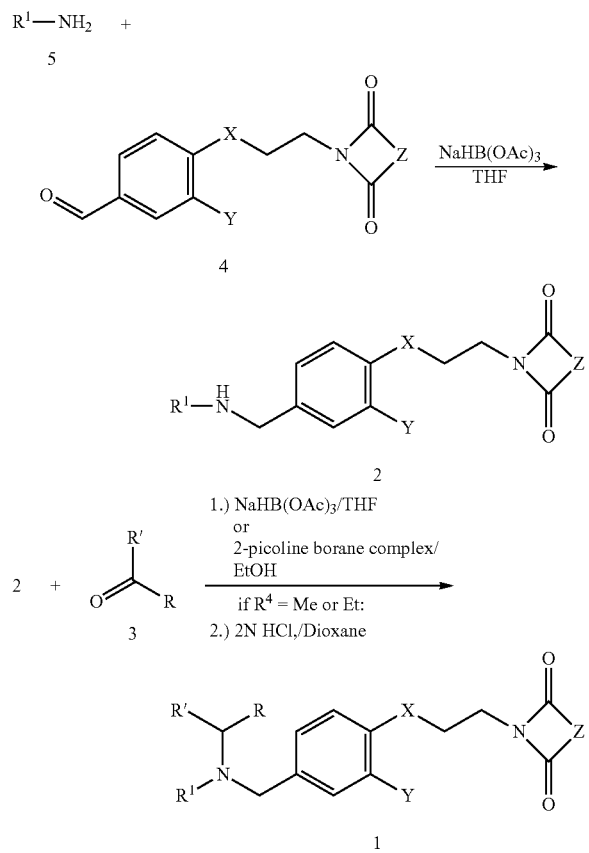

Starting materials of formula 3, 5, 6, 7 and 8 are commercially available or can be prepared by known methods.

As mentioned above the compounds of formula 1 or a pharmaceutically acceptable salt, stereoisomer or a pharmaceutically acceptable salt of the stereoisomer can be used as active ingredient of a medicament in the preventive and/or therapeutic treatment of a CXCR3 receptor mediated disease or disorder, especially of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) and lichen planus.

As the active ingredient of the medicament of the present invention, a substance may be used which is selected from the group consisting of the compound represented by the aforementioned formula 1 and pharmacologically acceptable salts, or stereoisomer thereof or a pharmaceutically acceptable salt of the stereoisomer. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

The present invention will be explained more specifically with reference to the following examples, however, the scope of the present invention is not limited to these examples.

Unless otherwise stated, the following abbreviations have the stated meanings in the examples below:
abs.=absolute
AcOH=Acetic acid
[(C₆H₅)₃P]₂PdCl₂=Bis(triphenylphosphine)palladium(II) dichloride
cc. HCl=concentrated hydrogen chloride solution
CuI=copper1 iodide
DCM=dichloromethane
Diazald=N-methyl-N-nitroso-p-toluenesulfonamide
DMF=N,N-dimethylformamide equiv.=equivalent
Et=ethyl
EtOH=ethanol
Et₂O=diethyl ether
EtOAc=ethyl acetate
HCCOH=formic acid
HPLC=high performance liquid chromatography
Ipam=isopropyl amine
K₂CO₃=potassium carbonate
K₃PO₄=potassium phosphate
KBr=potassium bromide
KOH=potassium hydroxide
LC/MS=liquid chromatography-mass spectrometry
MEK32 methyl-ethyl ketone
Me=methyl
MeOH=methanol
NaHCO₃=sodium bicarbonate
Na₂SO₄=sodium sulfate
NaBH(OAc)₃=sodium triacetoxy borohydride
nM=nanomole
NaOH=sodium hydroxide
NMR=nuclear magnetic spectroscopy
Pd(OAc)₂=palladium(II) acetate
r.t.=room temperature
TBAB=tetrabutylammonium bromide
TEA=triethylamine
THF=tetrahydrofuran
TsOH=p-toluenesulfonic acid monohydrate Analytical LC/MS is performed using Waters Alliance 2695+2996 PDA at 220 nm.

A system) MS:Waters LCT Premier XE; Column: Atlantis dC18 (3 μm) 2.1×50 mm; flow 0.7 ml/min of acetonitrile/water/0.05% TFA gradient in ESI+ mode B system) MS: Micromass ZQ; Column: Purospher-STAR RP18e (3 μm) 4.6×55 mm; flow 1.6 ml/min of water/acetonitrile/20 mM NH₄OH gradient or Xterra MS-C18 (3.5 μM) 2.1×50 mm; flow: 1.0 ml/min of water/acetonitrile/20 mM NH₄OH gradient in ESI+ mode.

Preparative chiral HPLC is performed using Berger Prep SFC at 210 nm;

C system) Column: Chiralpack IC 250×21 mm (5 μm) Flow: 50 ml/min; CO2/[Methanol/+0.5% Ipam] 70%/30% (other circumstances are detailed in examples).

For structural confirmation NMR spectra are measured for all compounds as well. The NMR spectra are recorded on a Bruker Advance II 400 MHz spectrometer at ambient temperature in DMSO-d₆ solution. The chemical shifts are referred to tetramethylsilane (δ, ppm). In some cases not only ¹H but ¹³C, ed-HSQC, zqs-TOCSY and HMBC spectra are also recorded.

PRECURSOR PREPARATIONS

Intermediate 4.1

4-[2-(2,5-Dioxo-pyrrolidin-1-yl)-ethoxy]-3-methoxy-benzaldehyde

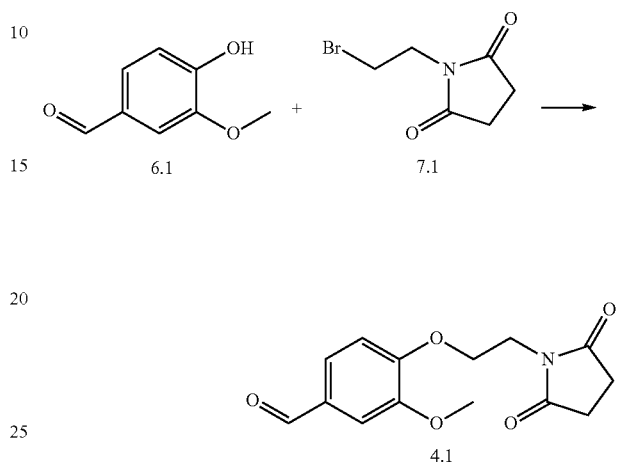

A method: 6.85 g (45 mmol) of vanilline (6.1) and 10.2 g (49.5 mmol) 1-(2-bromo-ethyl)-pyrrolidine-2,5-dione (7.1) is heated with 8.28 g (60 mmol) K₂CO₃ in 200 ml of acetonitrile under reflux for 15 h. Precipitated KBr is filtered off, the filtrate is evaporated, the residue is dissolved in 200 ml of dichloromethane, washed with water and 2N NaOH solution, dried with Na₂SO₄ and evaporated. The remaining oil is triturated with n-hexane to result the desired 4.1 in white crystals. Yield: 6.88 g (55%). (M+H)⁺=278, R_t (A)=1.90 min, purity 97.6%.

¹H-NMR: 2.64 (s, 4H), 3.77 (t, 2H), 2.75 (s, 3H), 4.21 (t, 3H), 7.17 (d, 1H), 7.40 (d, 1H), 7.53 (dd, 1H), 9.84 (s, 1H).

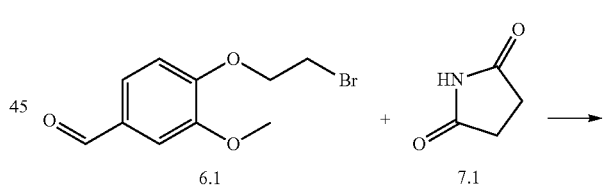

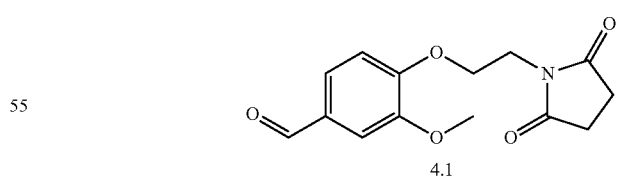

B method: 11.66 g (45 mmol) of 4-(2-bromo-ethoxy)-3-methoxy-benzaldehyde (6.2) and 4.46 g (45 mmol) pyrrolidine-2,5-dione (7.2) is heated with 8.28 g (60 mmol) K₂CO₃ in 200 ml of acetonitrile for 8 h. After same isolation procedure as in A method 4.1 is given with same purity.

Following the procedure as outlined for intermediate 4.1, the intermediates of general formula 4a listed in Table 2 are prepared.

TABLE 2

| Intermediate | Structure | (M + H)+ | R_t min. (system) | Purity (%) |
|---|---|---|---|---|
| 4.2 | 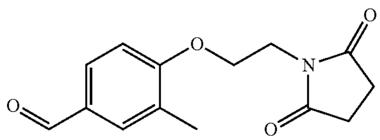 | 262 | 2.25 (A) | 98.2 |
| 4.3 | 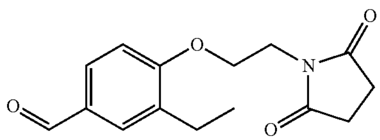 [SMILES: CCc1cc(C=O)ccc1OCCN1C(=O)CCC1=O] | 276 | 2.45 (A) | 98.3 |
| 4.4 | 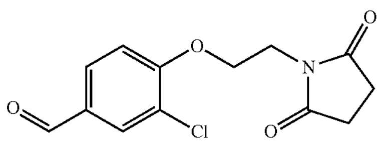 [SMILES: O=Cc1ccc(OCCN2C(=O)CCC2=O)c(Cl)c1] | 282 | 2.26 (A) | 98.3 |
| 4.5 | 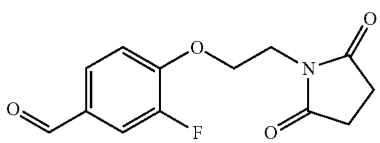 | 266 | 3.36 (B) | 99.3 |
| 4.6 | 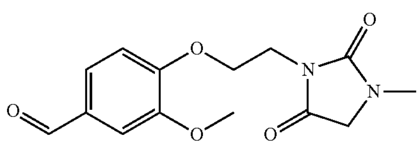 [SMILES: COc1cc(C=O)ccc1OCCN1C(=O)CN(C)C1=O] | 293 | 1.86 (A) | 98.7 |
| 4.7 | 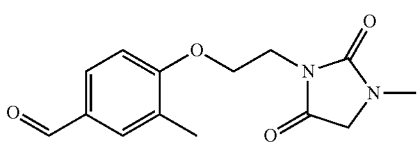 [SMILES: Cc1cc(C=O)ccc1OCCN1C(=O)CN(C)C1=O] | 277 | 2.28 (A) | 98.3 |
| 4.8 | 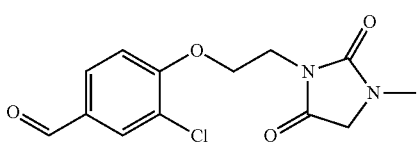 [SMILES: CN1CC(=O)N(CCOc2ccc(C=O)cc2Cl)C1=O] | 297 | 2.19 (A) | 95.3 |
| 4.9 | 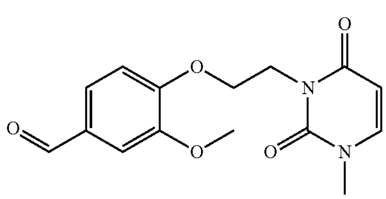 [SMILES: COc1cc(C=O)ccc1OCCn1c(=O)ccn(C)c1=O] | 305 | 2.08 (A) | 97.9 |
| 4.10 | 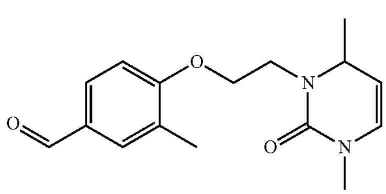 [SMILES: Cc1cc(C=O)ccc1OCCN1C(=O)N(C)C=CC1C] | 289 | 2.35 (A) | 99.6 |

TABLE 2-continued

| Intermediate | Structure | (M + H)+ | R_t min. (system) | Purity (%) |
|---|---|---|---|---|
| 4.11 | 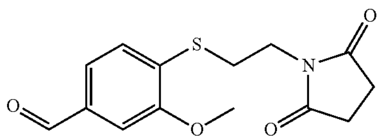 [SMILES: COc1cc(C=O)ccc1SCCN1C(=O)CCC1=O] | 294 | 2.34 (A) | 97.2 |

Intermediate 4.12

4-[3-(2,5-Dioxo-pyrrolidin-1-yl)-propyl]-3-methoxy-benzaldehyde

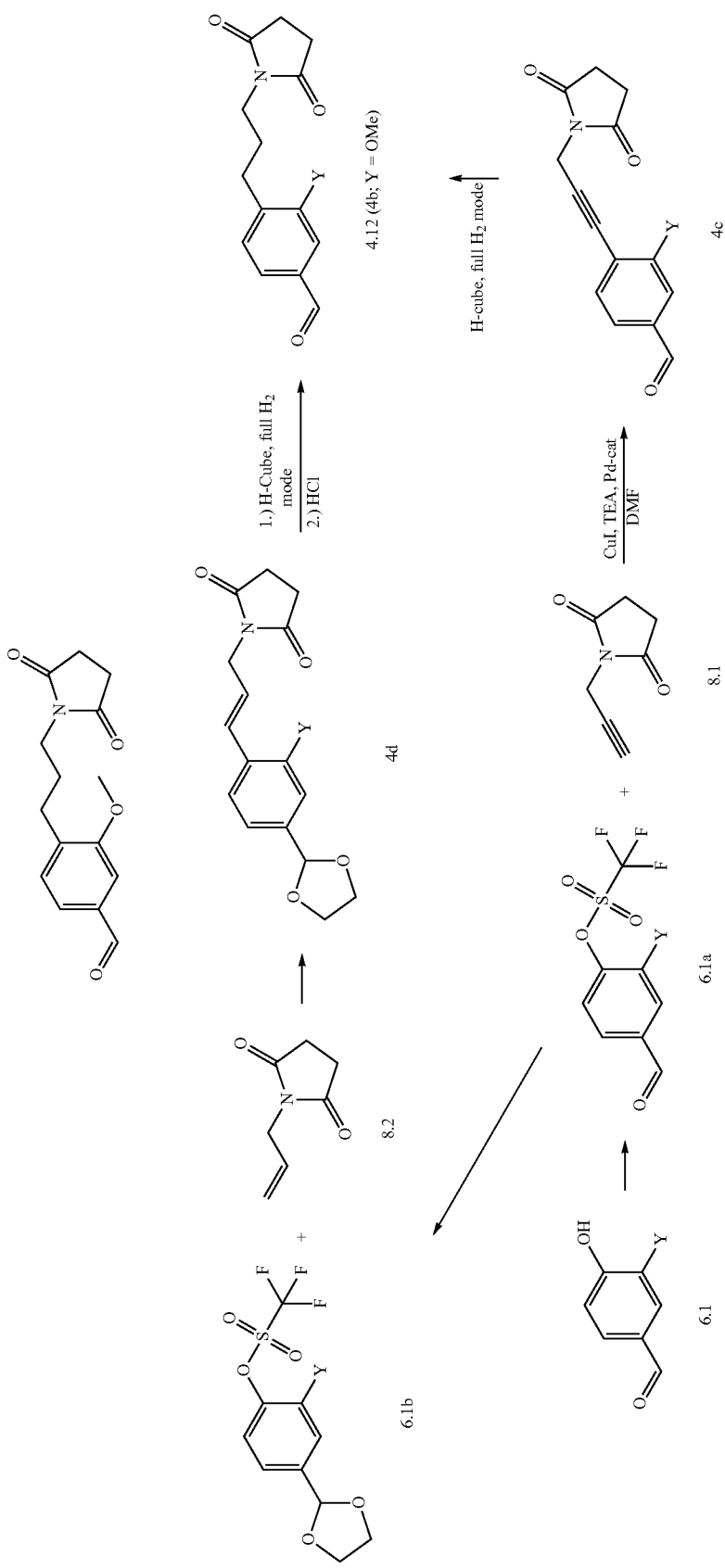

A Method:

Step 1: 6.85 g (45 mmol) vanilline (6.1, Y=OMe) is cooled in a 100 ml of a mixture of DCM-pyridine 4:1, then 9.1 ml (54 mmol) of trifluoromethanesulfonic anhydride in 10 ml DCM is dropped in. The mixture is stirred at r.t. for 2 hours, after evaporated and the residue is triturated with 3×10 ml of EtOAc, the collected organic layer is dried and evaporated. The crude material (6.1a) is used for next step without further purification.

Step 2: The formed crude trifluoro-methanesulfonic acid 4-formyl-2-methoxy-phenyl ester (6.1a), 2.52 ml (45 mmol) of ethylene glycol and 0.77 g (4.5 mmol) TsOH are refluxed in 180 ml of benzene. After evaporation the residue is purified by column chromatography. The desired intermediate is 11 g (80%) of trifluoro-methanesulfonic acid 4-[1,3]dioxolan-2-yl-2-methoxy-phenyl ester (6.1b), as a yellow oil. $(M+H)^+=329$, $R_t$ (A)=3.44 min, purity 93.4%.

Step 3: A mixture of 1.76 g (5 mmol) triflate (6.1b), 2.1 g (15 mmol) of 1-allyl-pyrrolidine-2,5-dione (8.2; *Bull. Chem. Soc. Japan,* 1984, 57(10), 3021), 0.067 g (0.3 mmol) of Pd(OAc)$_2$, 0.373 g (5 mmol) KCl, 3.22 g (10 mmol) TBAB and 2.12 g (10 mmol) K$_3$PO$_4$ is heated in 10 ml DMF under nitrogen at 120° C. for 8 h. The mixture is diluted with water, extracted with 3×50 ml of EtOAc, the collected organic phase is evaporated and purified by column chromatography (EtOAc-n-hexane 1:1). The desired intermediate (4d) is 1.8 g of 1-[(E)-3-(4-[1,3]dioxolan-2-yl-2-methoxy-phenyl)-allyl]-pyrrolidine-2,5-dione, as an oil. $(M+H)^+=318$, $R_t$ (A)=2.58 min, $R_t$ (B)=4.15 min, purity 71%.

Step 4: Using 3.02 g (9.2 mmol) of triflate (6.1a) a crude protected allyl derivative (4d) is formed (as described in step 2 and 3), which is hydrogenated by H-Cube equipment in full-H$_2$ mode in EtOAc. After evaporation the residue is dissolved in 50 ml of dioxane and stirred with 10 ml of cc. HCl at r.t. for 0.5 h. The mixture is evaporated, the residue is diluted with water, extracted with ethylacetate, dried and removed the solvent. The crude material is purified by flash chromatography. The desired product (Intermediate 4.12) is 1.65 g (65.3%). $(M+H)^+=276$, $R_t=2.57$ min (A), purity: 97.7%.

$^1$H-NMR: 1.75 (qv, 2H), 2.59-2.62 (m, 6H), 3.38 (t, 2H), 3.86 (s, 3H), 7.40 (d, 2H), 7.47 (dd, 1H), 9.94 (s, 1H).

B Method:

Step 1: A mixture of 4.26 g (15 mmol) triflate (6.1a), 2.47 g (18 mmol) of 1-prop-2-ynyl-pyrrolidine-2,5-dione (8.1), 0.067 g (0.3 mmol) of [(C$_6$H$_5$)$_3$P]$_2$PdCl$_2$, 0.143 g (0.75 mmol) CuI, 0.32 g (0.75 mmol) of 1,4-bis(diphenyl-phosphino)butane and 7 ml (50.5 mmol) of TEA is heated in 40 ml DMF under nitrogen at 100° C. for 3 h. The inorganic salts are removed and DMF is evaporated. The residue is treated with water, extracted 3×50 ml of EtOAc, the collected organic phase is evaporated and purified by flash chromatography (toluene-MeOH 9:1). The intermediate 4c is 1.9 g (44%) of 4-[3-(2,5-dioxo-pyrrolidin-1-yl)-prop-1-ynyl]-3-methoxy-benzaldehyde, as a dark yellow solid. $(M+H)^+=272$, $R_t=2.15$ min (A), purity: 98.9%. $^1$H-NMR: 2.71 (s, 4H), 3.89 (s, 3H), 4.44 (s, 2H), 7.47-7.50 (m, 2H), 7.55 (d, 1H), 9.98 (s, 1H).

Step 2: Hydrogenation of 4-[3-(2,5-dioxo-pyrrolidin-1-yl)-prop-1-ynyl]-3-methoxy-benzaldehyde (4c) in same circumstances as described in A method resulted Intermediate 4.12 in one step. The yield and purity is same as in A method.

Following procedures outlined for intermediate 4.12 the intermediate 4.13 is prepared.

Intermediate 4.13

4-[3-(2,5-Dioxo-pyrrolidin-1-yl)-propyl]-3-methyl-benzaldehyde

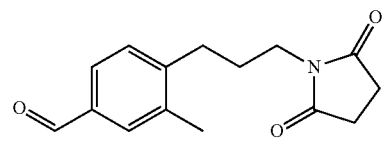 [SMILES: Cc1cc(C=O)ccc1CCCN1C(=O)CCC1=O]

$(M+H)^+=260$, $R_t=2.60$ min (A), purity: 96.0%.

EXAMPLE 1

3-(2,3-Dihydro-benzofuran-5-yl)-3-({4-[2-(2,5-dioxo-pyrrolidin-1-yl)-ethoxy]-3-methoxy-benzyl}-isobutyl-amino)-propionic acid

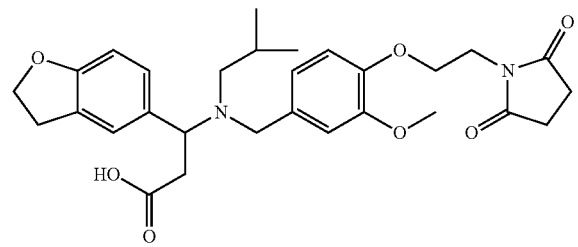 [SMILES: COc1cc(CN(CC(C)C)C(CC(=O)O)c2ccc3c(c2)CCO3)ccc1OCCN1C(=O)CCC1=O]

Step 1: 246 mg (0.089 mmol) of 3-amino-3-(2,3-dihydro-benzofuran-5-yl)-propionic acid ethyl ester (5.1) and 250 mg (1.06 mmol) of 4-[2-(2,5-dioxo-pyrrolidin-1-yl)-ethoxy]-3-methoxy-benzaldehyde (4.1) is dissolved in 12 ml of THF, then 60 µl (64 mg, 1.06 mmol) of glacial acetic acid and 751 mg (3.54 mmol) of triacetoxy borohydride is added in at room temperature. After 8 hour stirring the mixture is treated with water and extracted with ethyl acetate. The combined organic phase is dried and purified by flash chromatography. Yield is 309 mg (70%) of 2.1 with 91.3% purity.

Step 2: 400 mg (0.081 mmol) of 2.1 is dissolved in 14 ml of THF and 0.44 ml (349 mg, 4.83 mmol) of 2-methyl-propionaldehyde (3.1) 70 µl (73 mg, 1.21 mmol) of glacial acetic acid and 854 mg (4.03 mmol) of sodium triacetoxy borohydride are added in. The mixture is stirred at room temperature for 4 hours, treated with water, extracted with ethyl acetate and the combined organic phases are dried, evaporated and purified by flash chromatography. Yield is 347 mg (78%) of 1.1 ester. $(M+H)^+=553$, $R_t=2.66$ min (A), purity: 95.6%.

Salt formation: 101 mg (0.183 mmol) of 1.1 and 66 mg (0.183 mmol) of 1,5-naphthalenedisulfonic acid tetrahydrate is dissolved in 2 ml of EtOH, then evaporated, the residue is treated with Et$_2$O and the formed white solid is filtrated, and washed with Et$_2$O. Yield is 158 mg (48%) 1.1 with 1 moles 1,5-naphthalenedisulfonic acid. $(M+H)^+=553$, $R_t=2.66$ min (A), purity: 95.4%.

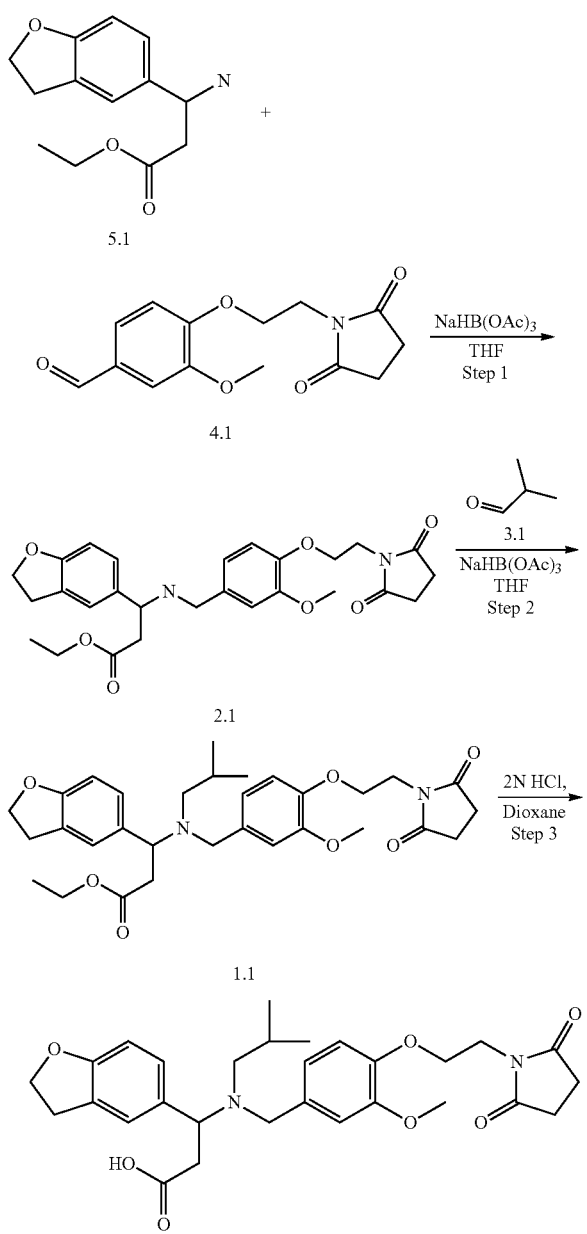

Example 1

Step 3: 227 mg of ester 1.1 is dissolved in 15 ml of dioxane, 5 ml of 2N HCl solution is added, and the mixture is stirred at 80° C. for 8 hours. After cooling the mixture is treated with 2N NaOH solution until pH=7 and extracted with dichloromethane. The combined organic phase is dried, evaporated and purified by flash chromatography.

Yield is 116 mg (54%) of desired product 1. Molecular Formula=$C_{29}H_{36}N_2O_7$; (M+H)$^+$=525, $R_t$=2.36 min (A), purity 98.2%.

$^1$H-NMR: 0.76 (dd, 6H), 1.77 (m, 1H), 2.0 (m, 2H), 2.58 (m, 1H), 2.61 (s, 4H), 2.94-3.00 (m, 2H), 3.17 (t, 2H), 3.67-3.71 (m, 6H), 4.03 (t, 2H), 4.17 (t, 1H), 4.51 (t, 2H), 6.73 (t, 2H), 6.83 (d, 1H), 6.98 (d, 2H), 7.15 (s, 1H), 12.3 (1 s, 1H).

EXAMPLE 2

3-(4-Chloro-phenyl)-3-({4-[2-(2,5-dioxo-pyrrolidin-1-yl)-ethoxy]-3-methoxy-benzyl}-isobutyl-amino)-propionic acid

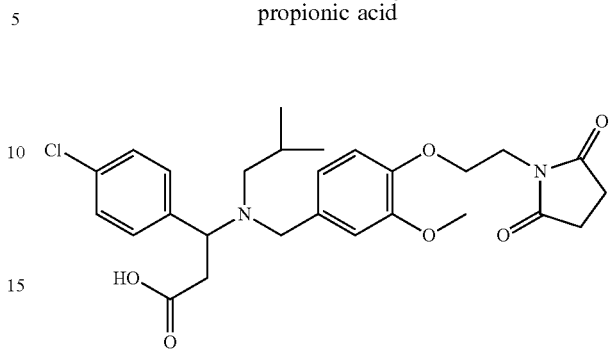

Following procedures outlined in Example 1 step 1 is accomplished with 3-Amino-3-(4-chloro-phenyl)-propionic acid ethyl ester (5.2) and Intermediate 4.1 then using 2-methyl-propionaldehyde (3.1) in step 2 after acidic hydrolysis and purification the title compound is isolated as a white foam. Molecular Formula=$C_{27}H_{33}ClN_2O_6$; (M+H)$^+$=517; $R_t$=2.53 min (A), purity 98.8%.

EXAMPLE 3

3-(Cyclopentylmethyl-{4-[2-(2,5-dioxo-pyrrolidin-1-yl)-ethoxy]-3-methoxy-benzyl}-amino)-3-(2,4-dichloro-phenyl)-propionic acid

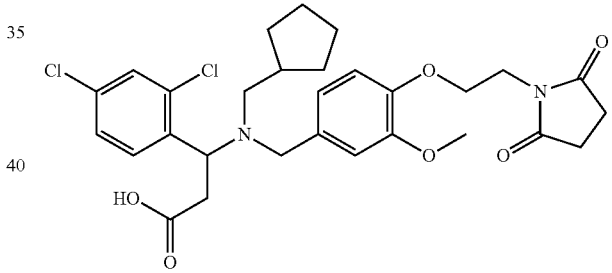

Step 1: 794 mg (3.03 mmol) of the 3-Amino-3-(2,4-dichloro-phenyl)-propionic acid ethyl ester (5.3) and 700 mg (2.52 mmol) of Intermediate 4.1 is dissolved in 30 ml of THF, then 170 μl (182 mg, 3.03 mmol) of glacial acetic acid and 2.14 g (10.10 mmol) of triacetoxy borohydride is added in at room temperature. After 24 hour stirring the mixture is treated with water and extracted with ethyl acetate. The combined organic phase is dried and purified with column chromatography. Yield is 466 mg (35%) of 2.2 with 92.3% purity.

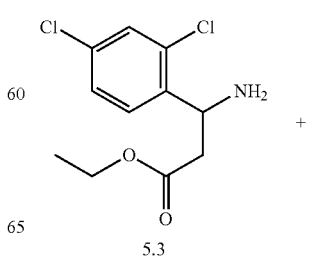

-continued

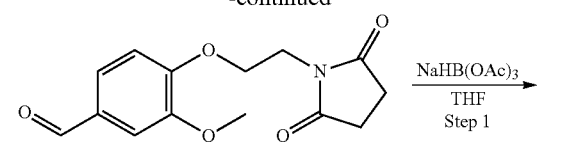

4.1

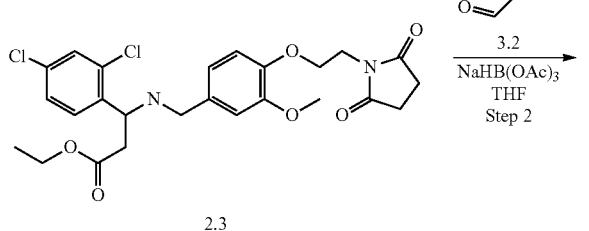

2.3

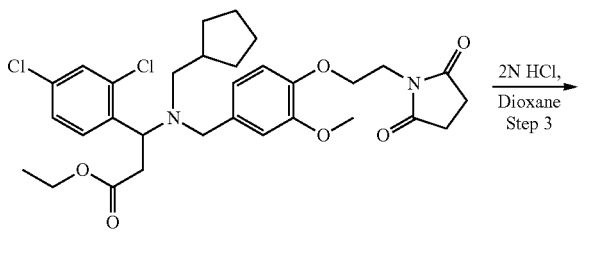

1.3

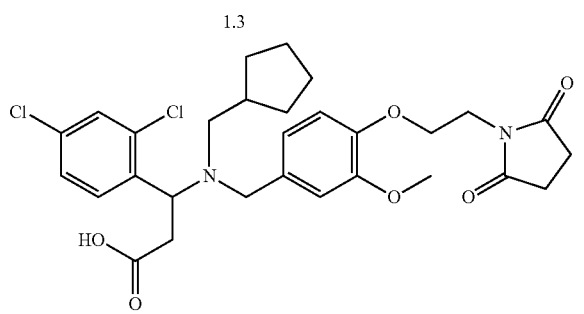

Example 3

Step 2: 235 mg (0.45 mmol) of 2.2 is dissolved in 10 ml of THF and 0.14 ml (1.35 mmol) of cyclopentane carboxaldehyde (3.2), 40 µl (40 mg, 0.67 mmol) of glacial acetic acid and 381 mg (1.80 mmol) of sodium triacetoxy borohydride is added in. The mixture is stirred at room temperature for 48 hours, treated with water, extracted with ethyl acetate and the combined organic phases are dried and evaporated. Yield is 376 mg (99%) of 1.2 ester (purity: 91.1%).

Step 3: This ester 1.2 is dissolved in 5 ml of dioxane, 3 ml of 2N HCl solution is added, and the mixture is stirred at 80° C. for 12 hours. After cooling the mixture is treated with 2N NaOH solution until pH=7 and extracted with dichloromethane. The combined organic phase is dried, evaporated and purified with chromatography.

Yield is 116 mg (35%) of desired product. Molecular Formula=$C_{29}H_{34}Cl_2N_2O_6$; (M+H)$_+$=577, $R_t$=2.80 min (A), purity 98.4%.

EXAMPLE 4

3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid

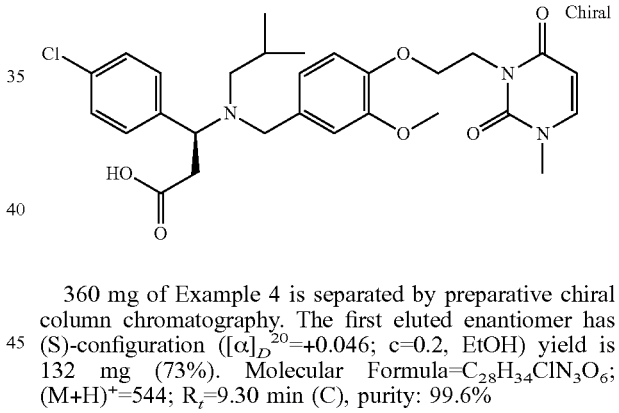

Following procedures outlined in Example 2 using Intermediate 4.9 after acidic hydrolysis and purification the title compound is isolated as a white foam. Molecular Formula=$C_{28}H_{34}ClN_3O_6$; (M+H)$^+$=544; $R_t$=2.64 min (A), purity 94.7%.

EXAMPLE 5

(S)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid

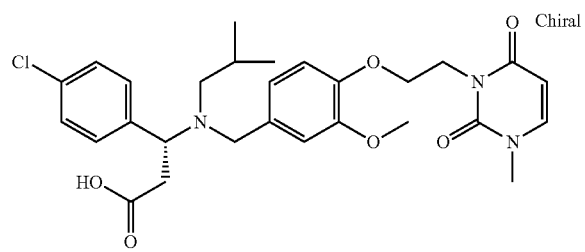 [SMILES: COc1cc(CN(CC(C)C)[C@H](CC(=O)O)c2ccc(Cl)cc2)ccc1OCCn1c(=O)ccn(C)c1=O]

360 mg of Example 4 is separated by preparative chiral column chromatography. The first eluted enantiomer has (S)-configuration ($[\alpha]_D^{20}$=+0.046; c=0.2, EtOH) yield is 132 mg (73%). Molecular Formula=$C_{28}H_{34}ClN_3O_6$; (M+H)$^+$=544; $R_t$=9.30 min (C), purity: 99.6%

EXAMPLE 6

(R)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid 360 mg of Example 4 is separated by preparative chiral column chromatography. The second eluted enantiomer has (R)-configuration ([α]$_D^{20}$=−0.033; c=0.2, EtOH) yield is 133 mg (74%). Molecular Formula=$C_{28}H_{34}ClN_3O_6$; (M+H)$^+$=544; $R_t$=10.6 min (C), purity: 99.6%

EXAMPLE 7

3-(4-Chloro-phenyl)-3-(cyclobutyl-{3-methyl-4-[2-(3-methyl-2,6-dioxo-3,6-dihydro-2H-pyrimidin-1-yl)-ethoxy]-benzyl}-amino)-propionic acid

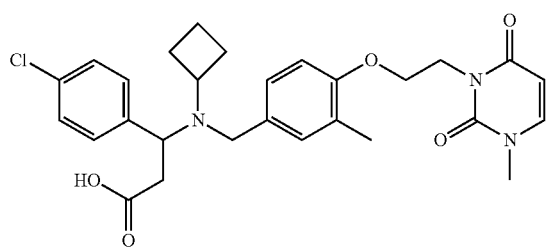 [SMILES: Cc1cc(CN(C2CCC2)C(CC(=O)O)c2ccc(Cl)cc2)ccc1OCCn1c(=O)ccn(C)c1=O]

Following procedures outlined in Example 2 step 1 is accomplished with 3-Amino-3-(4-chloro-phenyl)-propionic acid ethyl ester (5.2) and Intermediate 4.10. secondary amine derivative 2.7 is formed.

Step 2: 310 mg (0.62 mmol) of 2.7 is dissolved in 10 ml of EtOH then 52 mg (0.74 mmol) of cyclobutanone (3.3), 54 µl (56 mg, 0.93 mmol) of glacial acetic acid and 80 mg (0.74 mmol) of picoline borane complex is added in. The mixture is stirred at 85° C. for 72 hours, diluted with water, extracted with ethyl acetate and the combined organic phases are dried, evaporated and purified by flash chromatography. Yield is 130 mg (38%) of 1.7 ester. (M+H)$^+$=554, $R_t$=2.93 min (A), purity: 85.3%.

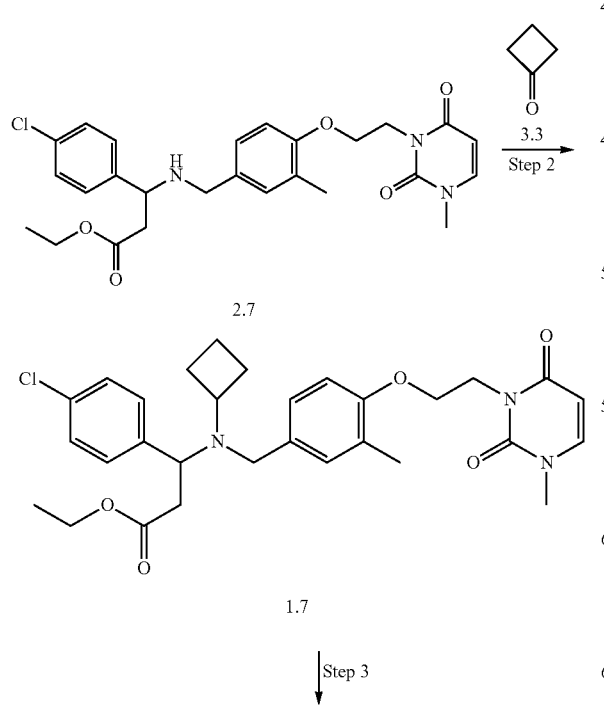

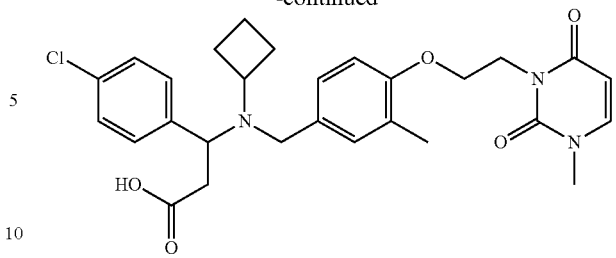

Example 7

Step 3: 120 mg (0.22 mmol) of ester 1.7 is dissolved in 2 ml of dioxane, 2 ml of 2N HCl solution is added, and the mixture is stirred at 80° C. for 3 hours. After cooling the mixture is treated with 2N NaOH solution until pH=7 and extracted with dichloromethane. The combined organic phase is dried, evaporated and purified by flash chromatography. Yield is 50 mg (44%) of desired product. Molecular Formula=$C_{28}H_{32}ClN_3O_5$; (M+H)$^+$=526, $R_t$=2.61 min (A), purity 98.1%.

EXAMPLE 8

1-[(4-Chloro-phenyl)-({4-[2-(2,5-dioxo-pyrrolidin-1-yl)-ethoxy]-3-methyl-benzyl}-propyl-amino)-methyl]-cyclopropanecarboxylic acid

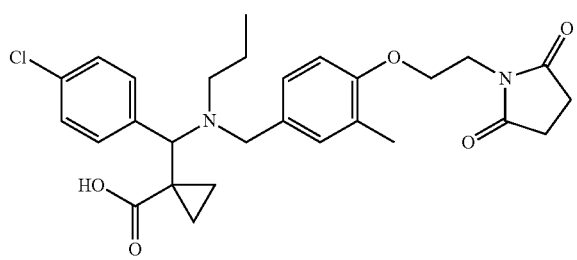 [SMILES: CCCN(Cc1ccc(OCCN2C(=O)CCC2=O)c(C)c1)C(c1ccc(Cl)cc1)C1(C(=O)O)CC1]

Synthesis of Intermediate 5.4

Step 1: 9.87 g (46.4 mmol) of 3-(4-Chloro-phenyl)-3-oxo-propionic acid methyl ester (5.4c), 17.44 g (92.8 mmol) of 1,2-dibromoethane and 16 g (115.8 mmol) of $K_2CO_3$ is heated in 500 ml of DMF at 90° C. for 2 hours. The mixture is stirred at room temperature at overnight, diluted with water and extracted with DCM. After the evaporation the crude material is purified by flash chromatography. Yield is 2.90 g (26%) of Intermediate 5.4b; (M+H)$^+$=239; $R_t$=3.21 min (A), purity: 95.8%.

Step 2: 2.26 g (9.47 mmol) of Intermediate 5.4b and 25.5 g (331.5 mmol) of ammonium acetate is refluxed in 100 ml of 2-propanol under inert atmosphere. Then 2.1 g (33.4 mmol) of sodium cyano borohydride is added and refluxed further 3 hours. The solvents is removed, the residue is acidified with 350 ml of 1N HCl solution, then washed with EtOAc, the acidic phase is adjusted with 5N NaOH solution to pH=8, then extracted with EtOAc, dried and evaporated. The crude Intermediate 5.4a is suitable for further step. Yield is 0.77 g (34%) yellow oil. (M+H)$^+$=240; $R_t$=2.00 min (A), purity: 97.7%.

Step 3: 0.72 g (3 mmol) of Intermediate 5.4a and 16 ml (0.64 g, 16 mmol) of 1N NaOH solution is stirred at 50° C.

for 3 hours. After acidification with 1N HCl solution the desired Intermediate 5.4 is separated as a white solid. Yield is 0.59 g (87%). (M+H)$^+$=226; $R_t$=1.81 min (A), purity: 99.5%.

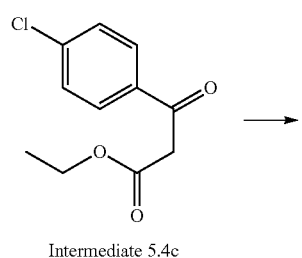

Intermediate 5.4c

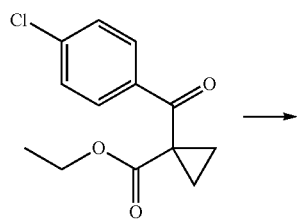

Intermediate 5.4b

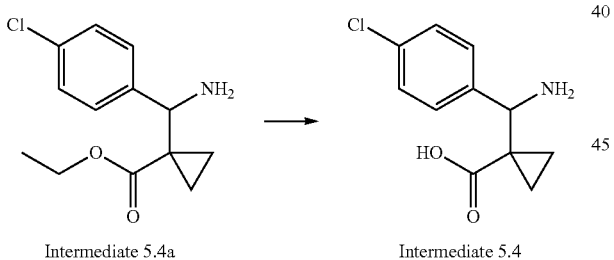

Intermediate 5.4a      Intermediate 5.4

"One Pot" Synthesis of Example 8: 290 mg (1.29 mmol) Intermediate 5.4 is dissolved in 25 ml of EtOH, 340 mg (1.30 mmol) of Intermediate 4.2, 0.11 ml (116 mg, 1.93 mmol) of glacial acetic acid and 139 mg (1.30 mmol) of 2-picolin boran complex added in. The mixture is stirred at 70° C. for 3.5 hours, then 0.65 ml (523 mg, 9 mmol) of propionaldehyde (3.4) and 352 mg (3.30 mmol) of 2-picolin boran complex is added and the mixture is stirred at 70° C. for 24 hours. After cooling the mixture is treated with 2N NaOH solution until pH=7 and extracted with dichloromethane. The combined organic phase is dried, evaporated and purified by flash chromatography. Yield is 420 mg (64%) of desired product (Example 8).

Molecular Formula=$C_{28}H_{33}ClN_2O_5$; (M+H)$^+$=513; $R_t$=2.65 min (A), purity 97.9%.

EXAMPLE 9

(S)-3-(4-Chloro-phenyl)-3-({4-[2-(2,5-dioxo-pyrrolidin-1-yl)-ethoxy]-3-methyl-benzyl}-propyl-amino)-propionic acid

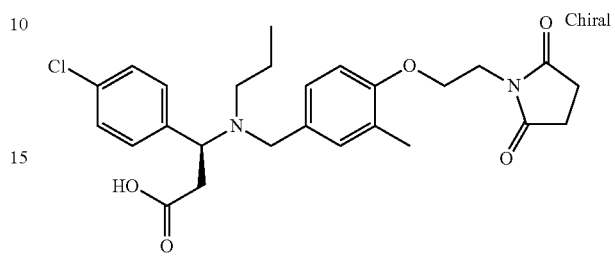

Following procedures outlined in Example 1 using (S)-3-Amino-3-(4-chloro-phenyl)-propionic acid ethyl ester (5.5) and Intermediate 4.2 in the first reductive amination step and propionaldehyde (3.4) in the second step, after acidic hydrolysis and purification the title compound is isolated as a white foam. Molecular Formula=$C_{26}H_{31}ClN_2O_5$; (M+H)$^+$=487; $R_t$=2.48 min (A), purity 98.6%. ($[\alpha]_D^{20}$+0.041; c=0.2, EtOH)

EXAMPLE 10

(R)-3-(4-Chloro-phenyl)-3-({4-[2-(2,5-dioxo-pyrrolidin-1-yl)-ethoxy]-3-methyl-benzyl}-propyl-amino)-propionic acid Following procedures outlined in Example 10 using (R)-3-Amino-3-(4-chloro-phenyl)-propionic acid ester (5.6) title compound is isolated as a white foam. Molecular Formula=$C_{26}H_{31}ClN_2O_5$; (M+H)$^+$=487; $R_t$=2.48 min (A), purity 96.3%. ($[\alpha]_D^{20}$=−0.040; c=0.2, EtOH)

EXAMPLE 11

(S)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid; hydrochloride

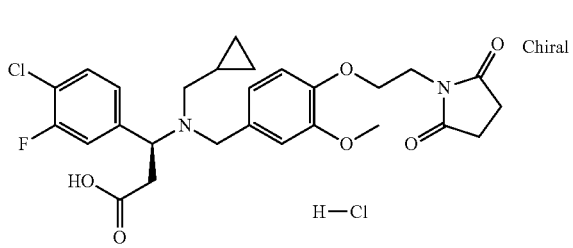 [SMILES: COc1cc(CN(CC2CC2)[C@@H](CC(=O)O)c2ccc(Cl)c(F)c2)ccc1OCCN1C(=O)CCC1=O ; Cl]

Following procedures outlined in Example 1 using (S)-3-Amino-3-(4-chloro-3-fluoro-phenyl)-propionic acid ethyl ester (5.7) and Intermediate 4.1 in the first reductive amination step and cyclopropanecarbaldehyde (3.5) in the second step, after acidic hydrolysis and purification the title compound is isolated as a hydrochloride. Molecular Formula=$C_{27}H_{30}ClFN_2O_6 \times HCl$. $(M+H)^+$=533; $R_t$=4.26 min (B), purity 100.0%. ($[\alpha]_D^{20}$+0.080; c=0.2, EtOH)

EXAMPLE 12

(R)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid; hydrochloride

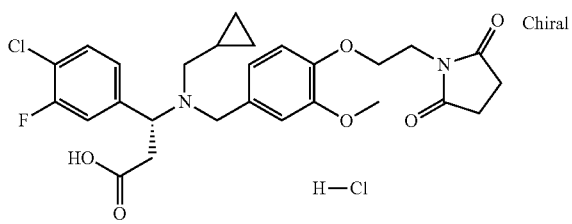 [SMILES: COc1cc(CN(CC2CC2)[C@H](CC(=O)O)c2ccc(Cl)c(F)c2)ccc1OCCN1C(=O)CCC1=O ; Cl]

Following procedures outlined in Example 11 using (R)-3-Amino-3-(4-chloro-3-fluoro-phenyl)-propionic acid ethyl ester (5.8) title compound is isolated as a white foam. Molecular Formula=$C_{27}H_{30}ClFN_2O_6 \times HCl$. $(M+H)^+$=533; $R_t$=2.39 min (A), purity 99.3%. ($[\alpha]_D^{20}$=−0.083; c=0.2, EtOH)

EXAMPLE 13

(S)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid; hydrochloride

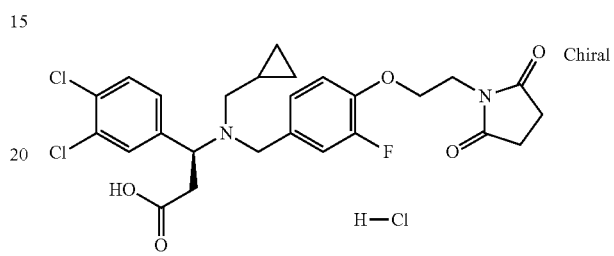

Following procedures outlined in Example 1 using (S)-3-Amino-3-(3,4-dichloro-phenyl)-propionic acid ethyl ester (5.9) and Intermediate 4.5 in the first reductive amination step and cyclopropanecarbaldehyde (3.5) in the second step, after acidic hydrolysis and purification the title compound is isolated as a hydrochloride. Molecular Formula=$C_{26}H_{27}Cl_2FN_2O_5 \times HCl$. $(M+H)^+$=537; $R_t$=4.85 min (B), purity 100.0%. ($[\alpha]_D^{20}$+0.069; c=0.2, EtOH)

EXAMPLE 14

(R)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid; hydrochloride

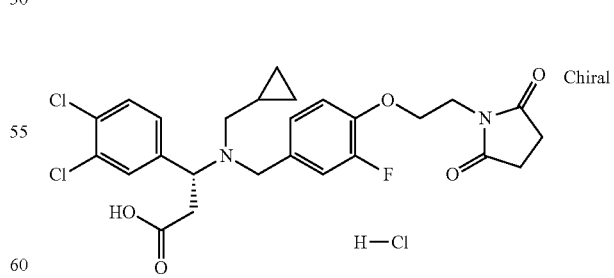

Following procedures outlined in Example 13 using (S)-3-Amino-3-(3,4-dichloro-phenyl)-propionic acid ethyl ester (5.10) title compound is isolated as a white foam. Molecular Formula=$C_{26}H_{27}Cl_2FN_2O_5 \times HCl$. $(M+H)^+$=537; $R_t$=2.60 min (A), purity 78.5%. ($[\alpha]_D^{20}$=−0.041; c=0.2, EtOH)

EXAMPLE 15

(S)-3-({3-Chloro-4-[2-(2,5-dioxo-pyrrolidin-1-yl)-ethoxy]-benzyl}-cyclopropylmethyl-amino)-3-(4-chloro-3-fluoro-phenyl)-propionic acid; hydrochloride

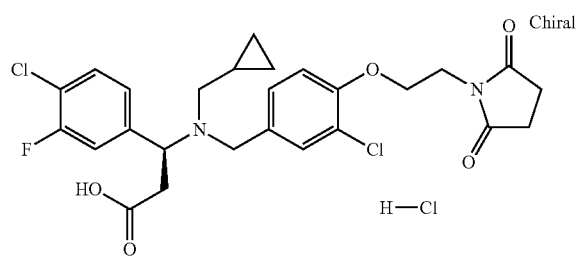 [SMILES: O=C(O)C[C@@H](c1ccc(Cl)c(F)c1)N(Cc1ccc(OCCN2C(=O)CCC2=O)c(Cl)c1)CC1CC1 ; Cl]

Following procedures outlined in Example 11 using (S)-3-Amino-3-(4-chloro-3-fluoro-phenyl)-propionic acid ethyl ester (5.7) and Intermediate 4.4 in the first reductive amination step and cyclopropanecarbaldehyde (3.5) in the second step, title compound is isolated as a hydrochloride. Molecular Formula=$C_{26}H_{27}Cl_2FN_2O_5\times HCl$. $(M+H)^+$=537; $R_t$=4.76 min (B), purity 99.5%. $([\alpha]_D^{20}$+0.086; c=0.2, EtOH)

EXAMPLE 16

(R)-3-({3-Chloro-4-[2-(2,5-dioxo-pyrrolidin-1-yl)-ethoxy]-benzyl}-cyclopropylmethyl-amino)-3-(4-chloro-3-fluoro-phenyl)-propionic acid; hydrochloride

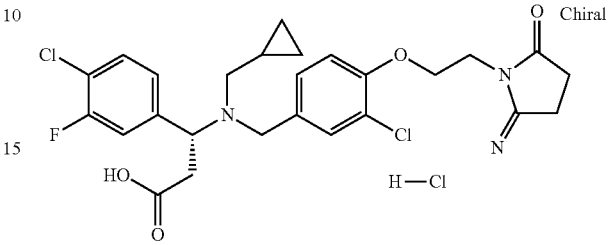

Following procedures outlined in Example 15 using (S)-3-Amino-3-(4-chloro-3-fluoro-phenyl)-propionic acid ethyl ester (5.8) title compound is isolated as a white foam. Molecular Formula=$C_{26}H_{27}Cl_2FN_2O_5\times HCl$. $(M+H)^+$=537; $R_t$=2.55 min (A), purity 99.0%. $([\alpha]_D^{20}$=−0.073; c=0.2, EtOH)

Following the procedures as outlined in Example 1-16 using different amines (5), benzaldehydes (4) and oxo derivatives (3) the compounds listed in Table 3 are prepared.

TABLE 3

| Examples | Structure | (M + H)⁺ | Rt min. (system) | Purity (%) |
|---|---|---|---|---|
| 17. | 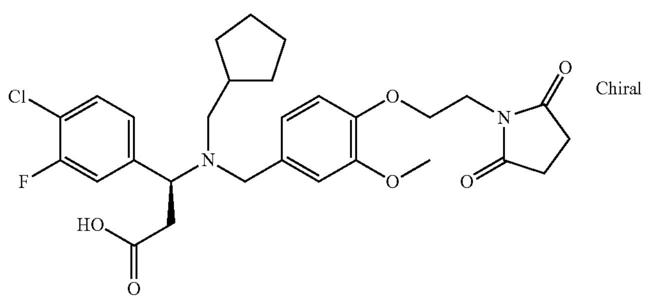 [SMILES: COc1cc(CN(CC2CCCC2)[C@@H](CC(=O)O)c2ccc(Cl)c(F)c2)ccc1OCCN1C(=O)CCC1=O] | 561 | 2.70 (A) | 97.8 |
| 18. | 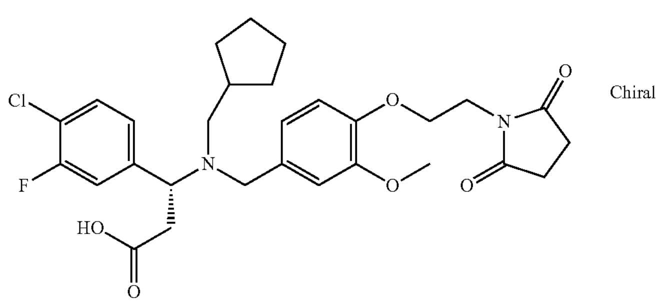 [SMILES: COc1cc(CN(CC2CCCC2)[C@H](CC(=O)O)c2ccc(Cl)c(F)c2)ccc1OCCN1C(=O)CCC1=O] | 561 | 2.69 (A) | 99.8 |

TABLE 3-continued
| Examples | Structure | (M + H)⁺ | Rt min. (system) | Purity (%) |
|---|---|---|---|---|
| 19. | 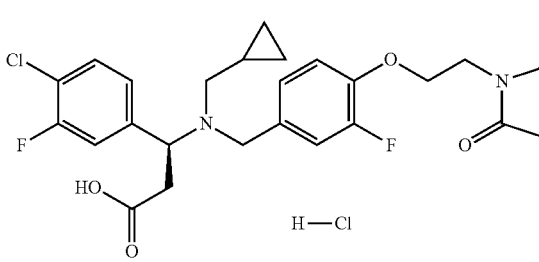 | 521 | 4.57 (B) | 99.6 |
| 20. | 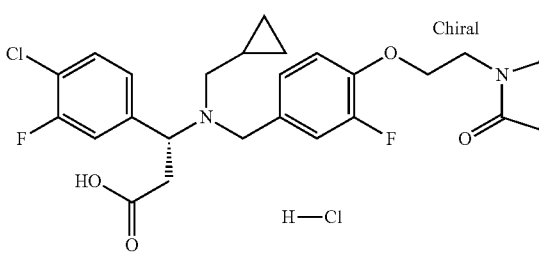 | 521 | 4.57 (B) | 99.9 |
| 21. | 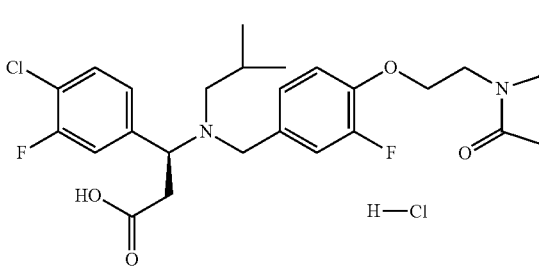 | 523 | 2.71 (A) | 99.2 |
| 22. | 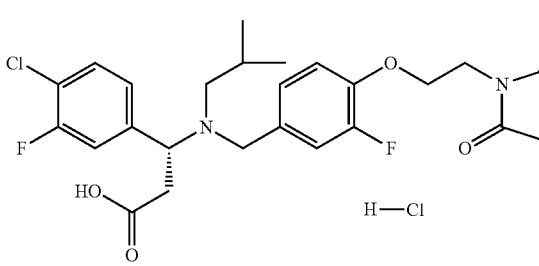 | 523 | 2.72 (A) | 96.5 |
| 23. | 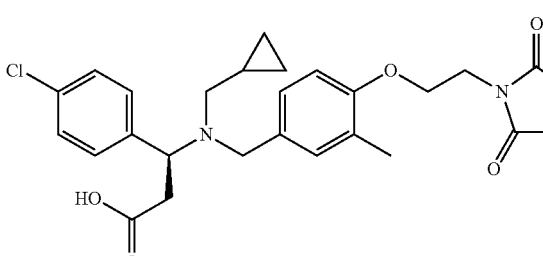 | 499 | 2.52 (A) | 96.4 |

TABLE 3-continued
| Examples | Structure | (M + H)+ | Rt min. (system) | Purity (%) |
|---|---|---|---|---|
| 24. | 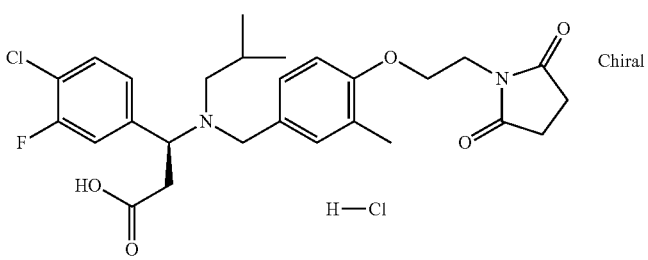 [SMILES: Cc1cc(CN(CC(C)C)[C@@H](CC(=O)O)c2ccc(Cl)c(F)c2)ccc1OCCN1C(=O)CCC1=O ; Cl] Chiral H—Cl | 519 | 4.92 (B) | 99.6 |
| 25. | 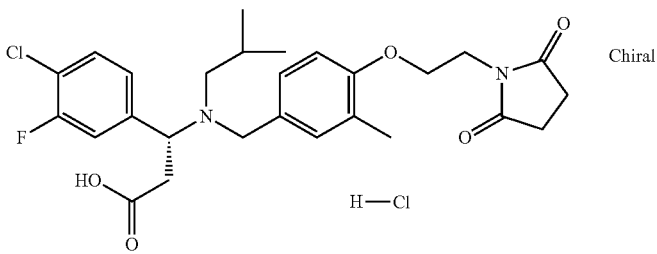 [SMILES: Cc1cc(CN(CC(C)C)[C@H](CC(=O)O)c2ccc(Cl)c(F)c2)ccc1OCCN1C(=O)CCC1=O ; Cl] Chiral H—Cl | 519 | 4.92 (B) | 99.4 |
| 26. | 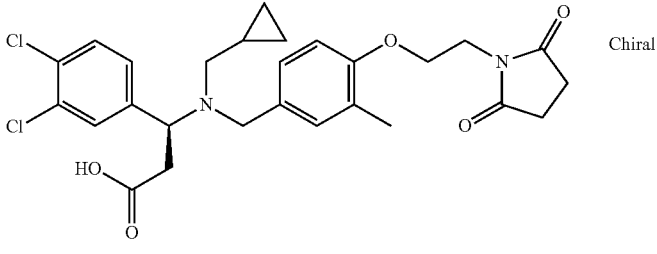 [SMILES: Cc1cc(CN(CC2CC2)[C@@H](CC(=O)O)c2ccc(Cl)c(Cl)c2)ccc1OCCN1C(=O)CCC1=O] Chiral | 533 | 2.64 (A) | 98.8 |
| 27. | 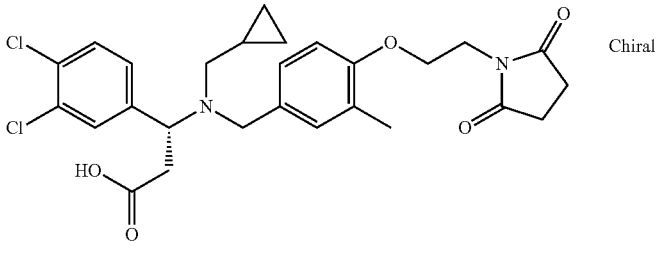 [SMILES: Cc1cc(CN(CC2CC2)[C@H](CC(=O)O)c2ccc(Cl)c(Cl)c2)ccc1OCCN1C(=O)CCC1=O] Chiral | 533 | 2.64 (A) | 98.7 |
| 28. | 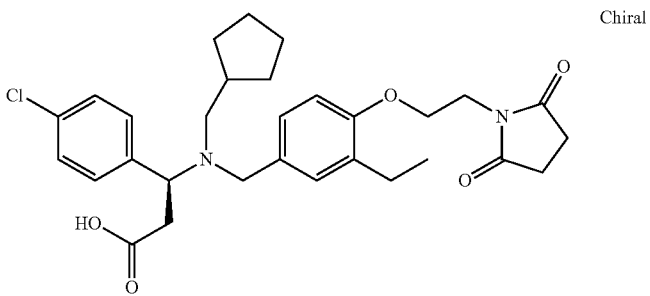 [SMILES: CCc1cc(CN(CC2CCCC2)[C@@H](CC(=O)O)c2ccc(Cl)cc2)ccc1OCCN1C(=O)CCC1=O] Chiral | 541 | 2.92 (A) | 98.5 |

TABLE 3-continued

| Examples | Structure | | (M + H)+ | Rt min. (system) | Purity (%) |
|---|---|---|---|---|---|
| 29. | [Structure: 4-chlorophenyl group with chiral carbon bearing CH2COOH and N(CH2-cyclopentyl)(CH2-phenyl-ethyl-O-CH2CH2-N-succinimide)] | Chiral | 541 | 2.91 (A) | 98.8 |
| 30. | [Structure: 4-chlorophenyl group with chiral carbon bearing CH2COOH and N(CH2-cyclohexyl)(CH2-phenyl-methyl-O-CH2CH2-N-methylhydantoin)] | Chiral | 556 | 5.06 (B) | 99.1 |
| 31. | [Structure: 4-chlorophenyl group with chiral carbon bearing CH2COOH and N(CH2-cyclohexyl)(CH2-phenyl-methyl-O-CH2CH2-N-methylhydantoin), opposite stereochemistry] | Chiral | 556 | 5.05 (B) | 97.5 |
| 32. | [Structure: 4-chloro-3-fluorophenyl group with chiral carbon bearing CH2COOH and N(CH2-cyclopentyl)(CH2-phenyl-methyl-O-CH2CH2-N-methylhydantoin)] | Chiral | 560 | 2.79 (A) | 99.6 |
| 33. | [Structure: 4-chloro-3-fluorophenyl group with chiral carbon bearing CH2COOH and N(CH2-cyclopentyl)(CH2-phenyl-methyl-O-CH2CH2-N-methylhydantoin), opposite stereochemistry] | Chiral | 560 | 2.78 (A) | 99.7 |

TABLE 3-continued
| Examples | Structure | (M + H)+ | Rt min. (system) | Purity (%) |
|---|---|---|---|---|
| 34. | 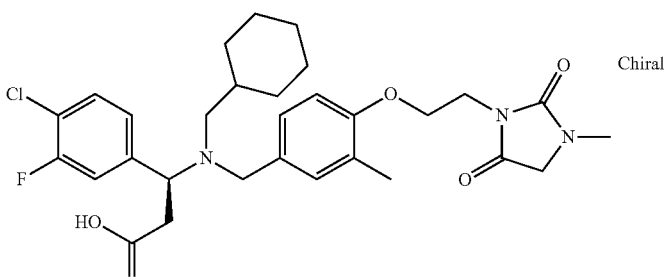 Chiral | 574 | 2.91 (A) | 99.5 |
| 35. | 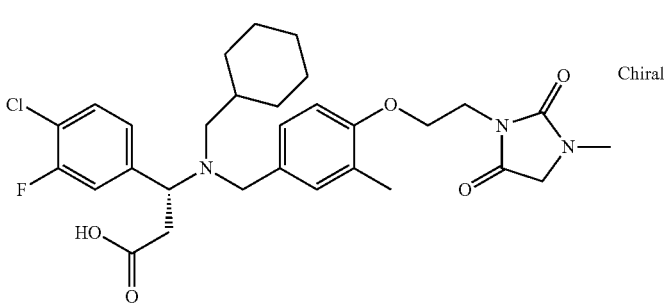 [SMILES: Cc1cc(CN(CC2CCCCC2)[C@H](CC(=O)O)c2ccc(Cl)c(F)c2)ccc1OCCN1C(=O)CN(C)C1=O] Chiral | 574 | 2.91 (A) | 99.2 |
| 36. | 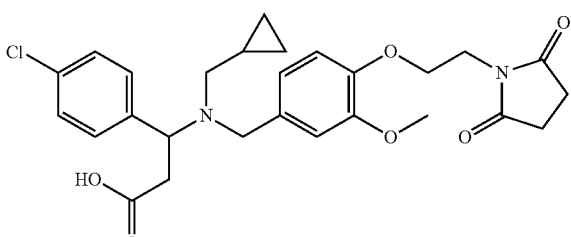 | 515 | 2.36 (A) | 98.2 |
| 37. | 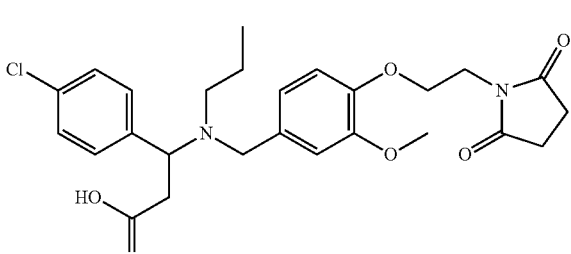 | 503 | 2.31 (A) | 97.4 |
| 38. | 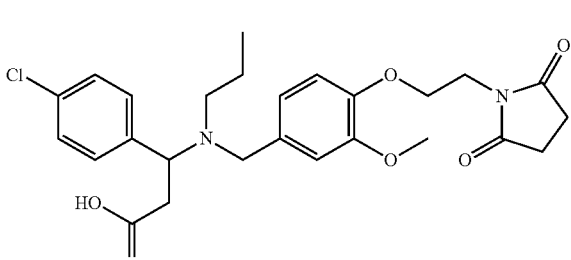 | 517 | 2.61 (A) | 98.2 |

TABLE 3-continued

| Examples | Structure | (M + H)⁺ | Rt min. (system) | Purity (%) |
|---|---|---|---|---|
| 39. | 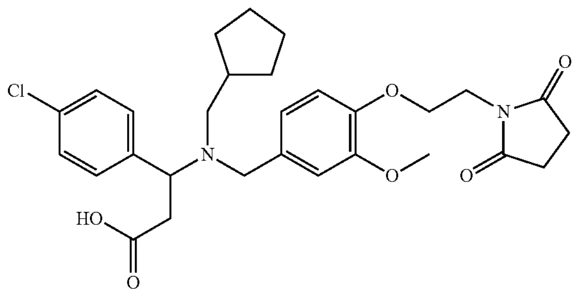 [SMILES: COc1cc(CN(CC2CCCC2)C(CC(=O)O)c2ccc(Cl)cc2)ccc1OCCN1C(=O)CCC1=O] | 543 | 2.81 (A) | 95.4 |
| 40. | 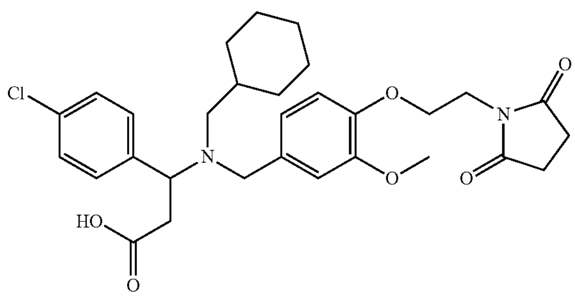 [SMILES: COc1cc(CN(CC2CCCCC2)C(CC(=O)O)c2ccc(Cl)cc2)ccc1OCCN1C(=O)CCC1=O] | 557 | 2.80 (A) | 97.9 |
| 41. | 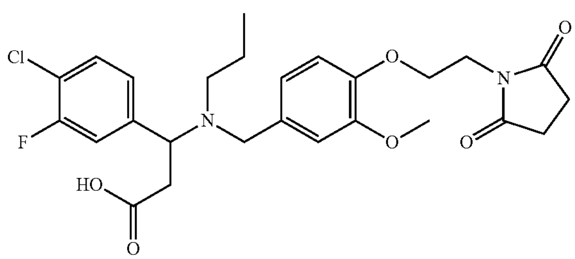 [SMILES: CCCN(Cc1ccc(OCCN2C(=O)CCC2=O)c(OC)c1)C(CC(=O)O)c1ccc(Cl)c(F)c1] | 521 | 2.36 (A) | 99.7 |
| 42. | 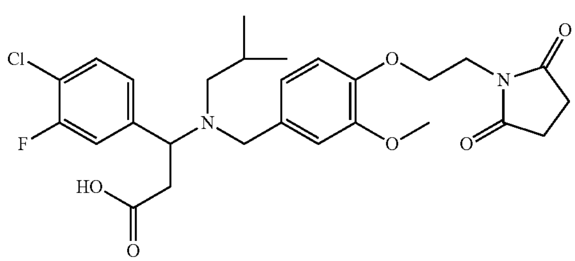 [SMILES: COc1cc(CN(CC(C)C)C(CC(=O)O)c2ccc(Cl)c(F)c2)ccc1OCCN1C(=O)CCC1=O] | 535 | 2.57 (A) | 98.5 |
| 43. | 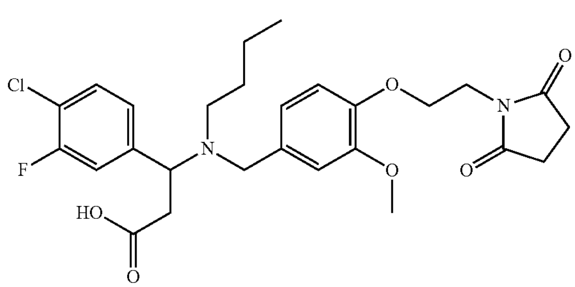 [SMILES: CCCCN(Cc1ccc(OCCN2C(=O)CCC2=O)c(OC)c1)C(CC(=O)O)c1ccc(Cl)c(F)c1] | 535 | 2.51 (A) | 97.5 |

TABLE 3-continued

| Examples | Structure | (M + H)+ | Rt min. (system) | Purity (%) |
|---|---|---|---|---|
| 44. | 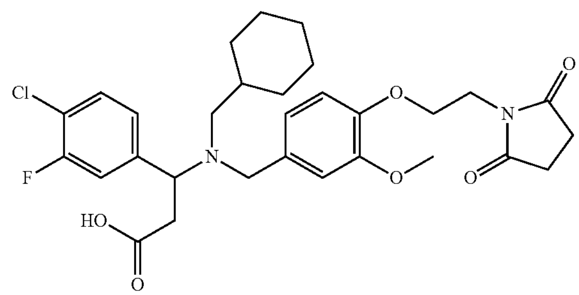 | 575 | 2.84 (A) | 98.9 |
| 45. | 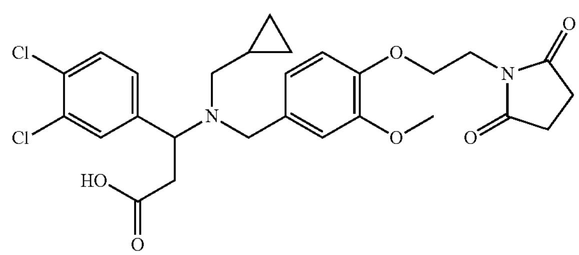 [SMILES: COc1cc(CN(CC2CC2)C(CC(=O)O)c2ccc(Cl)c(Cl)c2)ccc1OCCN1C(=O)CCC1=O] | 549 | 2.50 (A) | 99.0 |
| 46. | 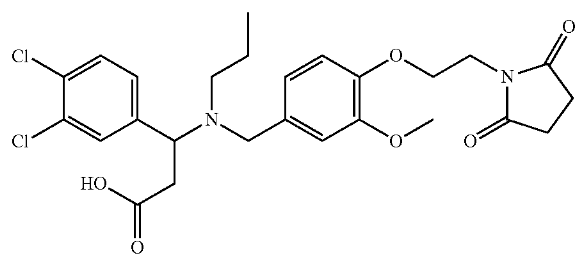 [SMILES: CCCN(Cc1ccc(OCCN2C(=O)CCC2=O)c(OC)c1)C(CC(=O)O)c1ccc(Cl)c(Cl)c1] | 537 | 2.48 (A) | 98.1 |
| 47. | 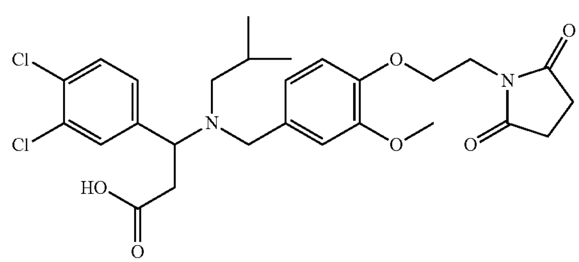 | 551 | 2.69 (A) | 98.2 |
| 48. | 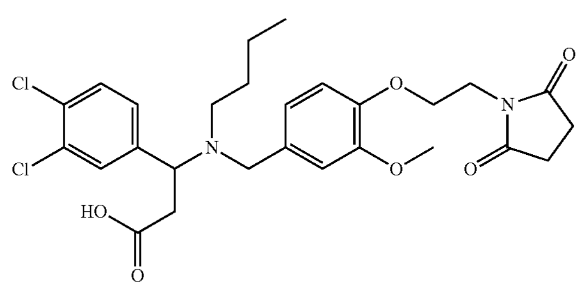 | 551 | 2.88 (A) | 95.7 |

TABLE 3-continued

| Examples | Structure | (M + H)+ | Rt min. (system) | Purity (%) |
|---|---|---|---|---|
| 49. | 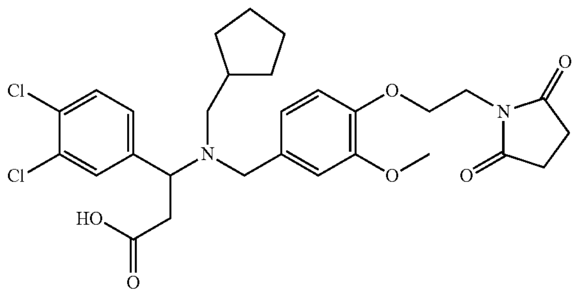 [SMILES: COc1cc(CN(CC2CCCC2)C(CC(=O)O)c2ccc(Cl)c(Cl)c2)ccc1OCCN1C(=O)CCC1=O] | 577 | 3.04 (A) | 92.3 |
| 50. | 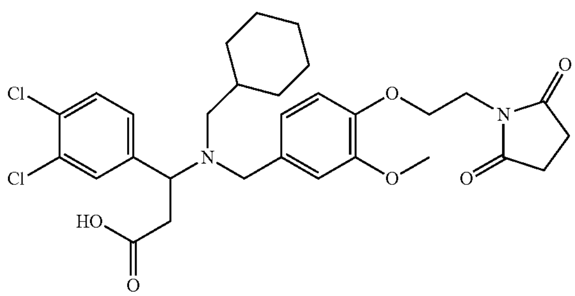 [SMILES: COc1cc(CN(CC2CCCCC2)C(CC(=O)O)c2ccc(Cl)c(Cl)c2)ccc1OCCN1C(=O)CCC1=O] | 591 | 2.95 (A) | 99.2 |
| 51. | 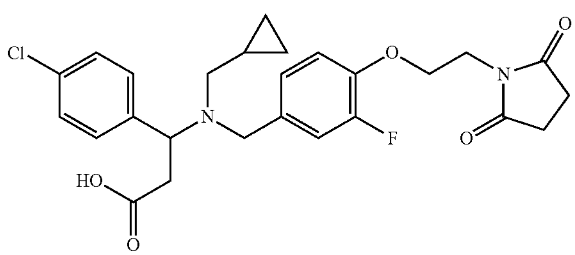 [SMILES: O=C(O)CC(c1ccc(Cl)cc1)N(Cc1ccc(OCCN2C(=O)CCC2=O)c(F)c1)CC1CC1] | 503 | 2.43 (A) | 99.2 |
| 52. | Chiral | 491 | 2.39 (A) | 99.2 |
| 53. | 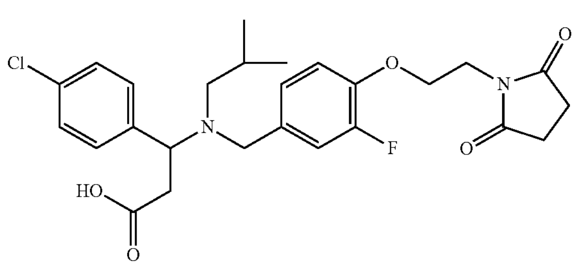 [SMILES: CC(C)CN(Cc1ccc(OCCN2C(=O)CCC2=O)c(F)c1)C(CC(=O)O)c1ccc(Cl)cc1] | 505 | 2.59 (A) | 99.4 |

TABLE 3-continued

| Examples | Structure | (M + H)+ | Rt min. (system) | Purity (%) |
|---|---|---|---|---|
| 54. | 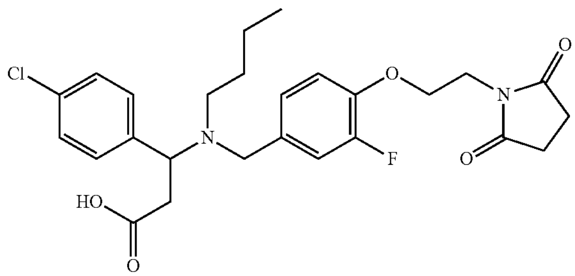 [SMILES: CCCCN(Cc1ccc(OCCN2C(=O)CCC2=O)c(F)c1)C(CC(=O)O)c1ccc(Cl)cc1] | 505 | 2.53 (A) | 93.9 |
| 55. | Chiral | 517 | 2.58 (A) | 99.7 |
| 56. | 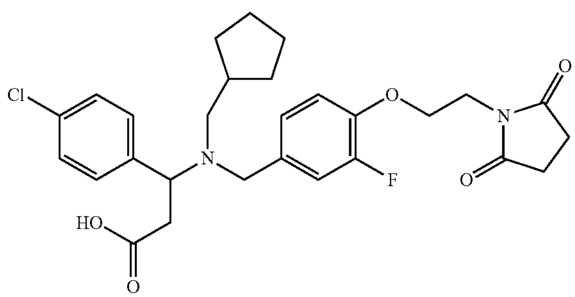 [SMILES: O=C(O)CC(c1ccc(Cl)cc1)N(Cc1ccc(OCCN2C(=O)CCC2=O)c(F)c1)CC1CCCC1] | 531 | 2.75 (A) | 99.3 |
| 57. | 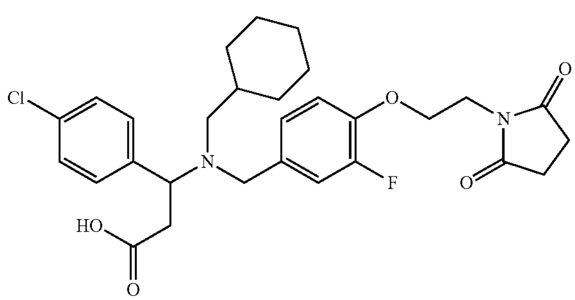 [SMILES: O=C(O)CC(c1ccc(Cl)cc1)N(Cc1ccc(OCCN2C(=O)CCC2=O)c(F)c1)CC1CCCCC1] | 545 | 2.88 (A) | 96.0 |
| 58. | 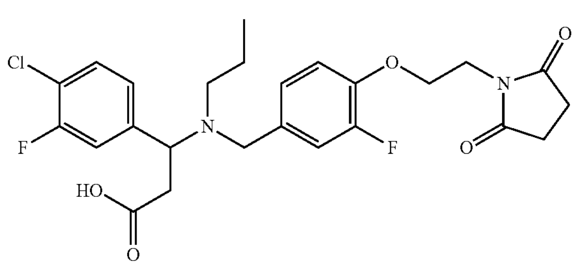 [SMILES: CCCN(Cc1ccc(OCCN2C(=O)CCC2=O)c(F)c1)C(CC(=O)O)c1ccc(Cl)c(F)c1] | 509 | 2.46 (A) | 98.8 |

TABLE 3-continued

| Examples | Structure | (M + H)+ | Rt min. (system) | Purity (%) |
|---|---|---|---|---|
| 59. | 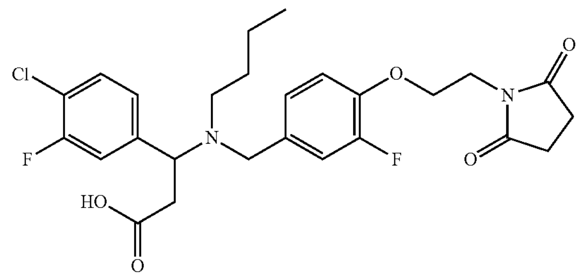 [SMILES: CCCCN(Cc1ccc(OCCN2C(=O)CCC2=O)c(F)c1)C(CC(=O)O)c1ccc(Cl)c(F)c1] | 523 | 2.60 (A) | 98.5 |
| 60. | 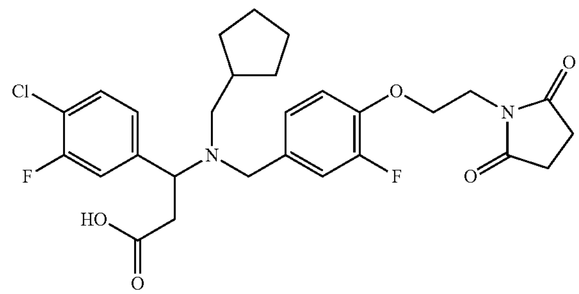 | 549 | 2.84 (A) | 98.4 |
| 61. | 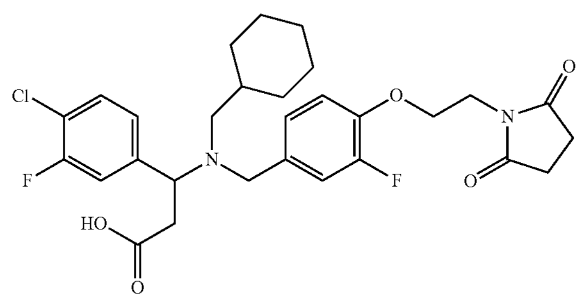 [SMILES: O=C(O)CC(c1ccc(Cl)c(F)c1)N(Cc1ccc(OCCN2C(=O)CCC2=O)c(F)c1)CC1CCCCC1] | 563 | 3.01 (A) | 99.4 |
| 62. | 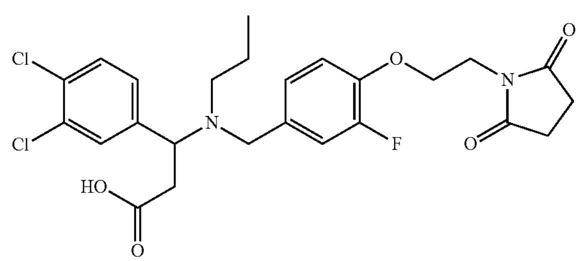 [SMILES: CCCN(Cc1ccc(OCCN2C(=O)CCC2=O)c(F)c1)C(CC(=O)O)c1ccc(Cl)c(Cl)c1] | 525 | 2.57 (A) | 84.9 |
| 63. | 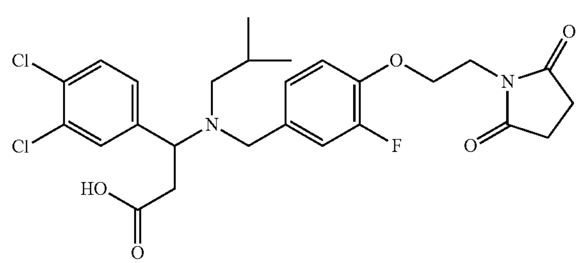 [SMILES: CC(C)CN(Cc1ccc(OCCN2C(=O)CCC2=O)c(F)c1)C(CC(=O)O)c1ccc(Cl)c(Cl)c1] | 539 | 2.86 (A) | 97.2 |

TABLE 3-continued

| Examples | Structure | (M + H)+ | Rt min. (system) | Purity (%) |
|---|---|---|---|---|
| 64. | 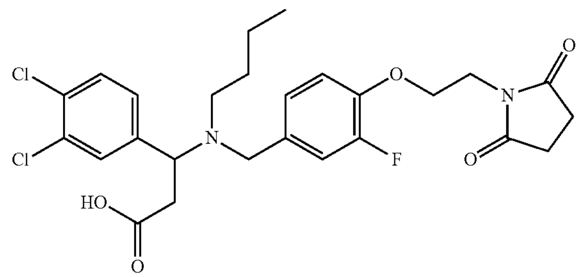 [SMILES: CCCCN(Cc1ccc(OCCN2C(=O)CCC2=O)c(F)c1)C(CC(=O)O)c1ccc(Cl)c(Cl)c1] | 539 | 2.72 (A) | 99.1 |
| 65. | 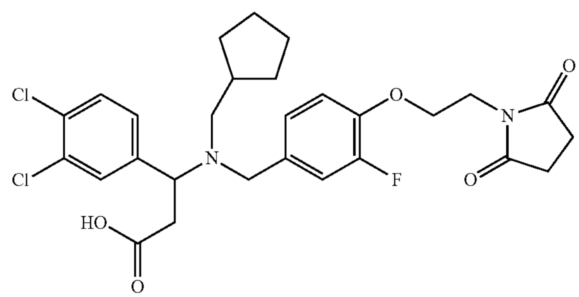 [SMILES: O=C(O)CC(c1ccc(Cl)c(Cl)c1)N(Cc1ccc(OCCN2C(=O)CCC2=O)c(F)c1)CC1CCCC1] | 565 | 2.95 (A) | 99 |
| 66. | 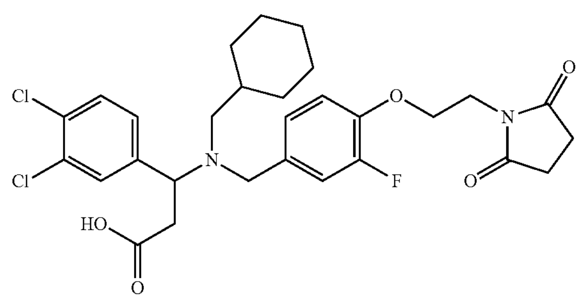 | 578 | 3.12 (A) | 98.0 |
| 67. | 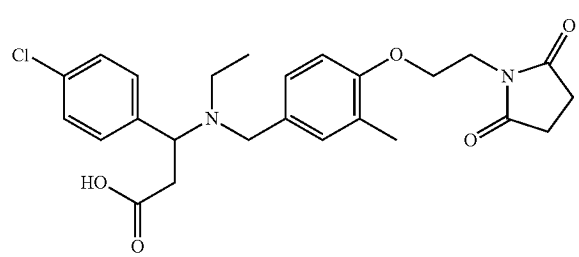 [SMILES: CCN(Cc1ccc(OCCN2C(=O)CCC2=O)c(C)c1)C(CC(=O)O)c1ccc(Cl)cc1] | 473 | 2.49 (A) | 99.4 |
| 68. | 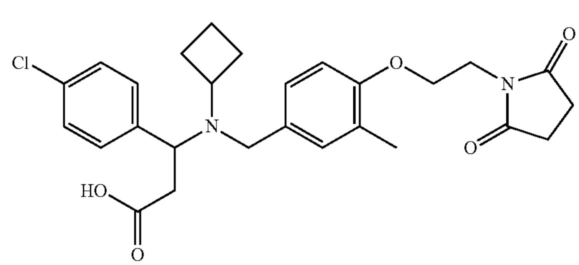 [SMILES: Cc1cc(CN(C2CCC2)C(CC(=O)O)c2ccc(Cl)cc2)ccc1OCCN1C(=O)CCC1=O] | 499 | 2.63 (A) | 99.8 |

TABLE 3-continued

| Examples | Structure | (M + H)+ | Rt min. (system) | Purity (%) |
|---|---|---|---|---|
| 69. | 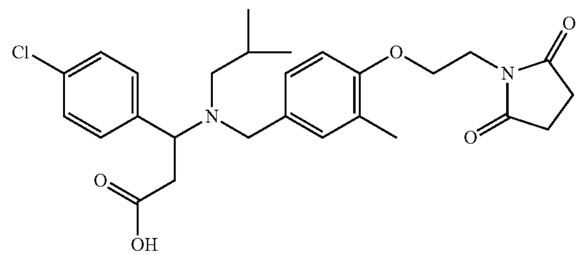 [SMILES: Cc1cc(CN(CC(C)C)C(CC(=O)O)c2ccc(Cl)cc2)ccc1OCCN1C(=O)CCC1=O] | 501 | 2.69 (A) | 97.1 |
| 70. | 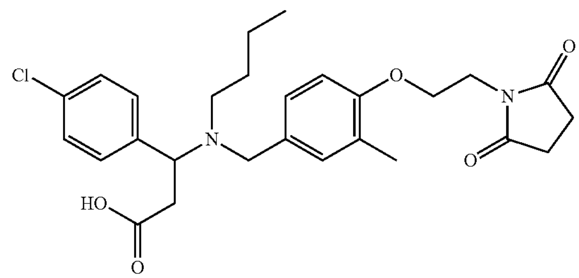 [SMILES: CCCCN(Cc1ccc(OCCN2C(=O)CCC2=O)c(C)c1)C(CC(=O)O)c1ccc(Cl)cc1] | 501 | 2.76 A) | 94.8 |
| 71. | Chiral | 513 | 2.65 (A) | 99.1 |
| 72. | 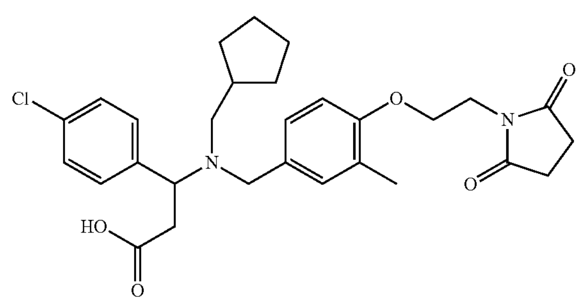 | 527 | 2.97 (A) | 98.4 |
| 73. | 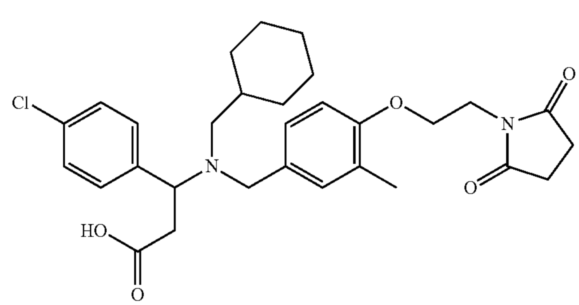 [SMILES: Cc1cc(CN(CC2CCCCC2)C(CC(=O)O)c2ccc(Cl)cc2)ccc1OCCN1C(=O)CCC1=O] | 541 | 3.10 (A) | 97.8 |

TABLE 3-continued

| Examples | Structure | (M + H)+ | Rt min. (system) | Purity (%) |
|---|---|---|---|---|
| 74. | 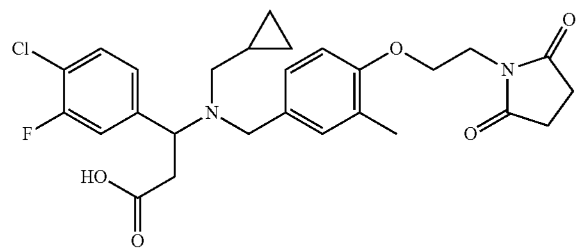 [SMILES: Cc1cc(CN(CC2CC2)C(CC(=O)O)c2ccc(Cl)c(F)c2)ccc1OCCN1C(=O)CCC1=O] | 517 | 2.56 (A) | 99.9 |
| 75. | 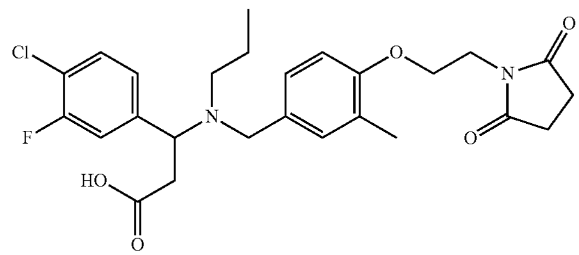 [SMILES: CCCN(Cc1ccc(OCCN2C(=O)CCC2=O)c(C)c1)C(CC(=O)O)c1ccc(Cl)c(F)c1] | 505 | 2.53 (A) | 99.6 |
| 76. | 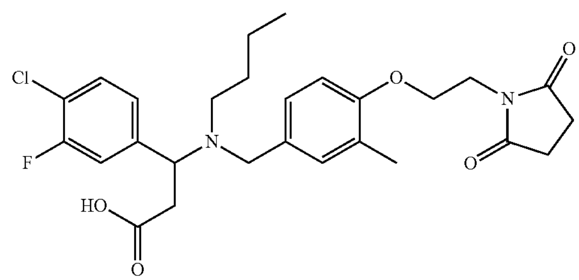 [SMILES: CCCCN(Cc1ccc(OCCN2C(=O)CCC2=O)c(C)c1)C(CC(=O)O)c1ccc(Cl)c(F)c1] | 519 | 2.65 (A) | 99.4 |
| 77. | 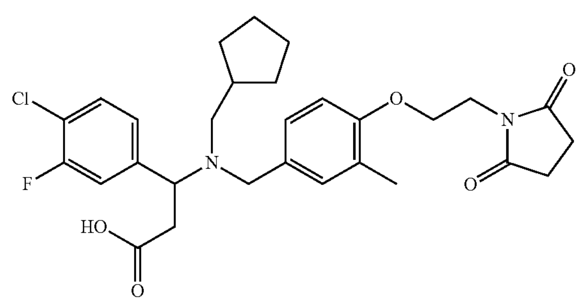 [SMILES: Cc1cc(CN(CC2CCCC2)C(CC(=O)O)c2ccc(Cl)c(F)c2)ccc1OCCN1C(=O)CCC1=O] | 545 | 2.84 (A) | 98.6 |
| 78. | 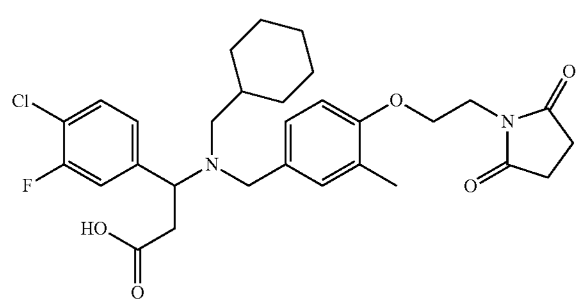 [SMILES: Cc1cc(CN(CC2CCCCC2)C(CC(=O)O)c2ccc(Cl)c(F)c2)ccc1OCCN1C(=O)CCC1=O] | 559 | 2.98 (A) | 99.2 |

TABLE 3-continued

| Examples | Structure | (M + H)+ | Rt min. (system) | Purity (%) |
|---|---|---|---|---|
| 79. | 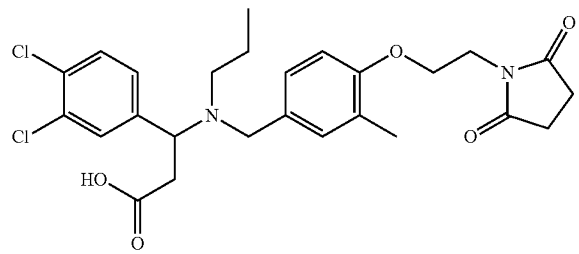 [SMILES: CCCN(Cc1ccc(OCCN2C(=O)CCC2=O)c(C)c1)C(CC(=O)O)c1ccc(Cl)c(Cl)c1] | 521 | 3.30 (A) | 99.0 |
| 80. | 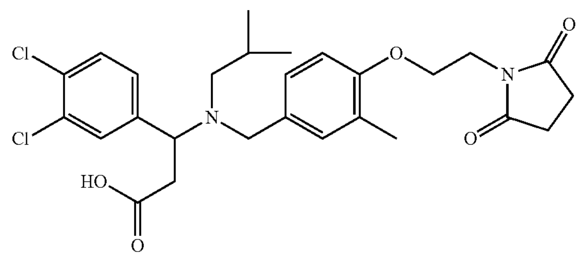 [SMILES: Cc1cc(CN(CC(C)C)C(CC(=O)O)c2ccc(Cl)c(Cl)c2)ccc1OCCN1C(=O)CCC1=O] | 535 | 3.67 A) | 98.8 |
| 81. | 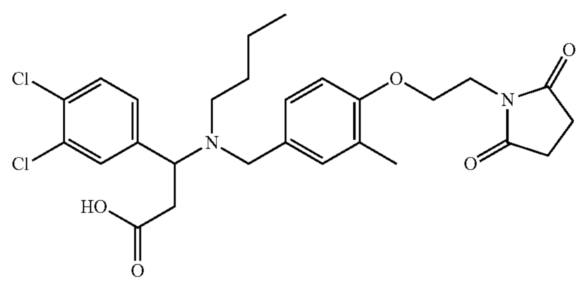 | 535 | 2.99 (A) | 99.6 |
| 82. | 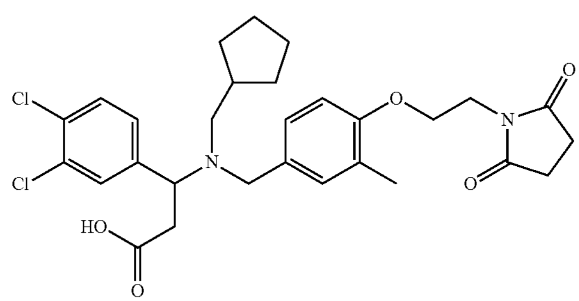 [SMILES: Cc1cc(CN(CC2CCCC2)C(CC(=O)O)c2ccc(Cl)c(Cl)c2)ccc1OCCN1C(=O)CCC1=O] | 561 | 2.95 (A) | 98.5 |
| 83. | 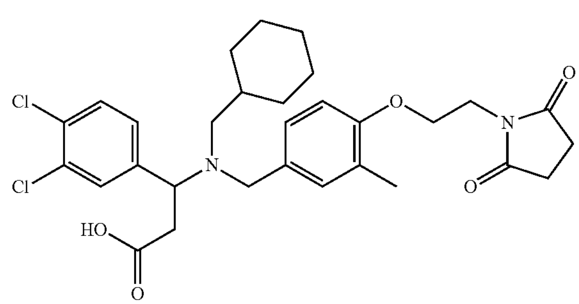 [SMILES: Cc1cc(CN(CC2CCCCC2)C(CC(=O)O)c2ccc(Cl)c(Cl)c2)ccc1OCCN1C(=O)CCC1=O] | 575 | 5.80 (B) | 96.1 |

TABLE 3-continued
| Examples | Structure | (M + H)+ | Rt min. (system) | Purity (%) |
|---|---|---|---|---|
| 84. | 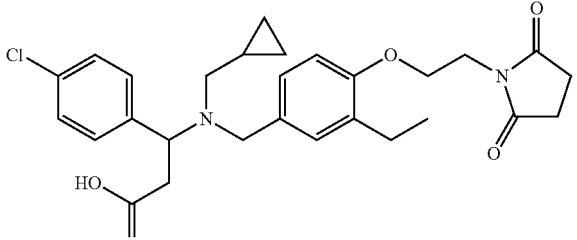 | 513 | 2.63 (A) | 99.4 |
| 85. | 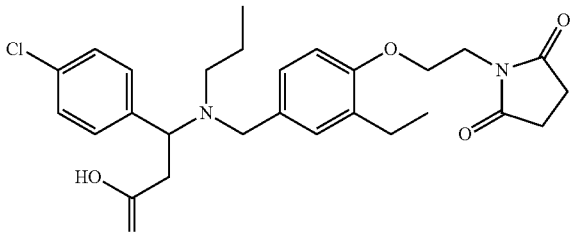 | 501 | 2.62 (A) | 90.8 |
| 86. | 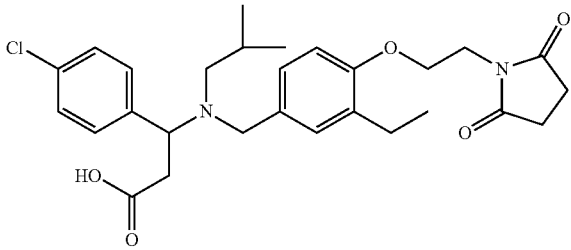 [SMILES: CCc1cc(CN(CC(C)C)C(CC(=O)O)c2ccc(Cl)cc2)ccc1OCCN1C(=O)CCC1=O] | 515 | 2.77 (A) | 96.0 |
| 87. | 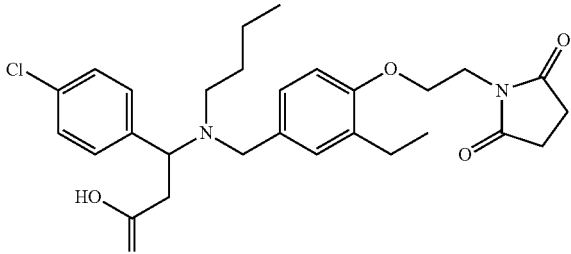 | 515 | 2.75 (A) | 97.5 |
| 88. | 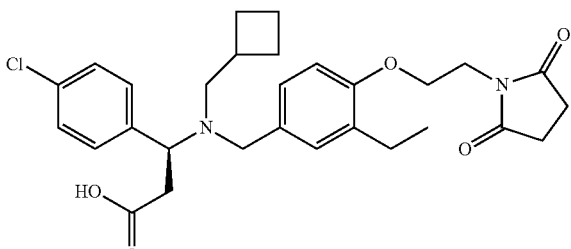 Chiral | 527 | 2.78 (A) | 99.0 |

TABLE 3-continued
| Examples | Structure | (M + H)+ | Rt min. (system) | Purity (%) |
|---|---|---|---|---|
| 89. | 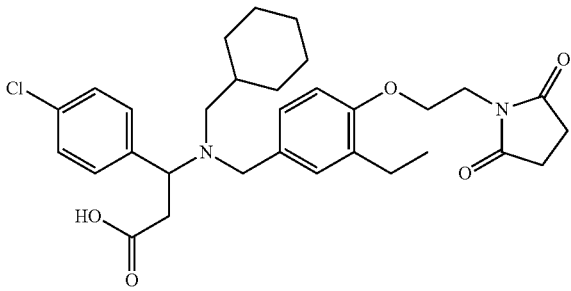 | 553 | 3.01 (A) | 93.7 |
| 90. | 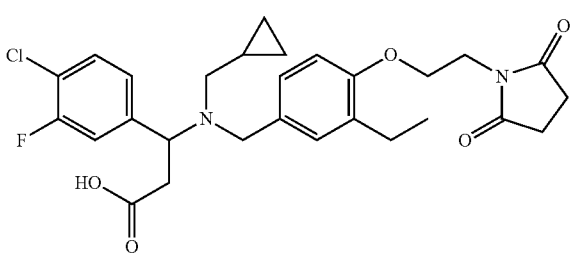 | 531 | 2.66 (A) | 98.6 |
| 91. | 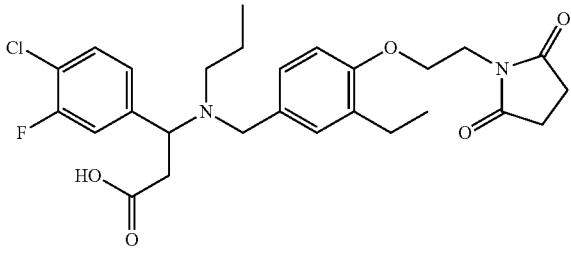 [SMILES: CCCN(Cc1ccc(OCCN2C(=O)CCC2=O)c(CC)c1)C(CC(=O)O)c1ccc(Cl)c(F)c1] | 519 | 2.64 (A) | 99.5 |
| 92. | 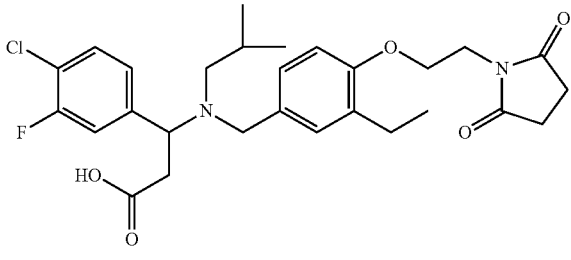 [SMILES: CCc1cc(CN(CC(C)C)C(CC(=O)O)c2ccc(Cl)c(F)c2)ccc1OCCN1C(=O)CCC1=O] | 533 | 2.83 (A) | 96.0 |
| 93. | 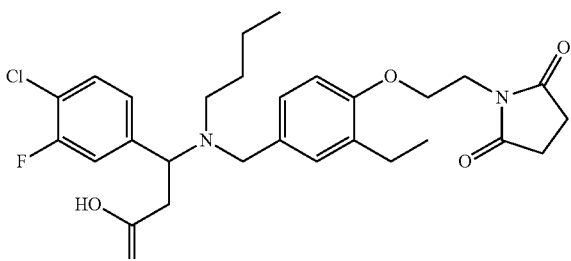 | 533 | 2.76 (A) | 99.8 |

TABLE 3-continued

| Examples | Structure | (M + H)+ | Rt min. (system) | Purity (%) |
|---|---|---|---|---|
| 94. | 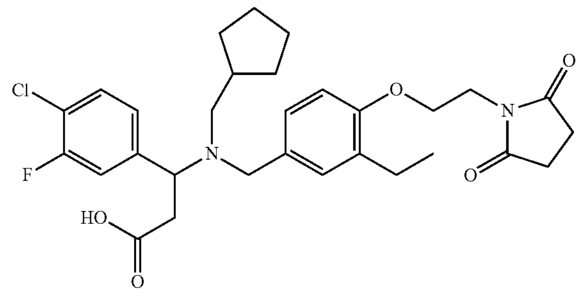 [SMILES: CCc1cc(CN(CC2CCCC2)C(CC(=O)O)c2ccc(Cl)c(F)c2)ccc1OCCN1C(=O)CCC1=O] | 559 | 2.95 (A) | 99.0 |
| 95. | 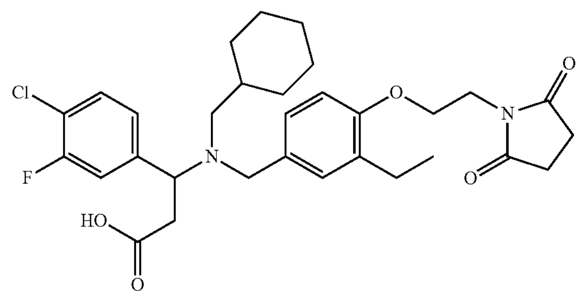 | 573 | 3.07 (A) | 96.2 |
| 96. | 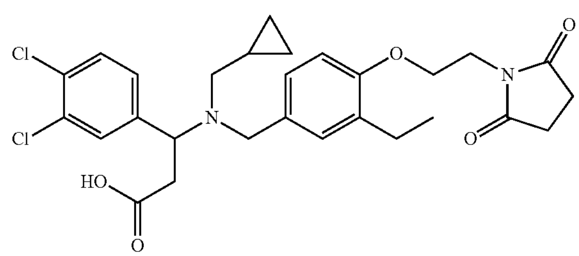 [SMILES: CCc1cc(CN(CC2CC2)C(CC(=O)O)c2ccc(Cl)c(Cl)c2)ccc1OCCN1C(=O)CCC1=O] | 547 | 2.76 (A) | 99.6 |
| 97. | 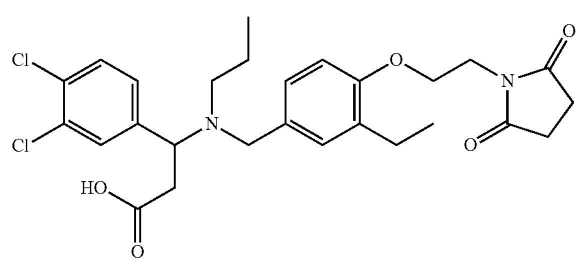 [SMILES: CCCN(Cc1ccc(OCCN2C(=O)CCC2=O)c(CC)c1)C(CC(=O)O)c1ccc(Cl)c(Cl)c1] | 534 | 2.73 (A) | 99.2 |
| 98. | 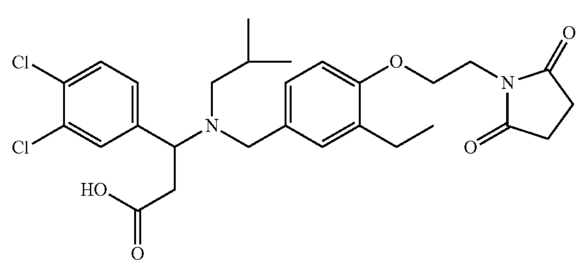 [SMILES: CCc1cc(CN(CC(C)C)C(CC(=O)O)c2ccc(Cl)c(Cl)c2)ccc1OCCN1C(=O)CCC1=O] | 549 | 2.93 (A) | 98.4 |

TABLE 3-continued

| Examples | Structure | (M + H)+ | Rt min. (system) | Purity (%) |
|---|---|---|---|---|
| 99. | 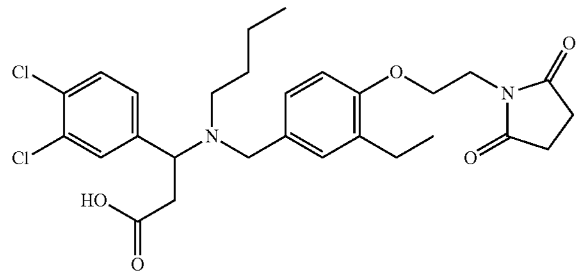 [SMILES: CCCCN(Cc1ccc(OCCN2C(=O)CCC2=O)c(CC)c1)C(CC(=O)O)c1ccc(Cl)c(Cl)c1] | 549 | 2.85 (A) | 99.6 |
| 100. | 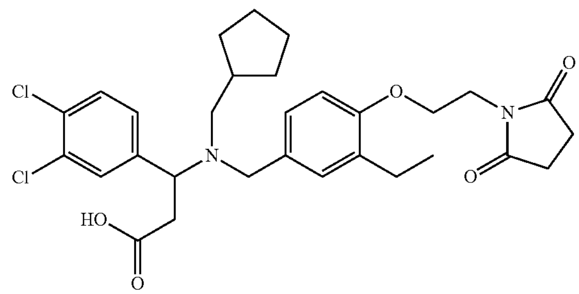 [SMILES: CCc1cc(CN(CC2CCCC2)C(CC(=O)O)c2ccc(Cl)c(Cl)c2)ccc1OCCN1C(=O)CCC1=O] | 575 | 3.06 (A) | 97.4 |
| 101. | 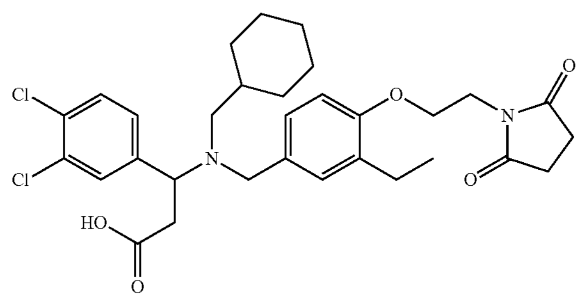 [SMILES: CCc1cc(CN(CC2CCCCC2)C(CC(=O)O)c2ccc(Cl)c(Cl)c2)ccc1OCCN1C(=O)CCC1=O] | 589 | 3.18 (A) | 95.9 |
| 102. | 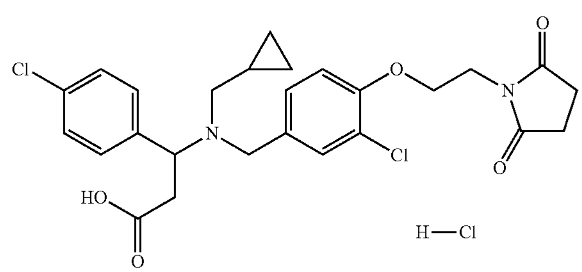 [SMILES: O=C(O)CC(c1ccc(Cl)cc1)N(Cc1ccc(OCCN2C(=O)CCC2=O)c(Cl)c1)CC1CC1 ; Cl] | 519 | 2.49 (A) | 98.4 |
| 103. | 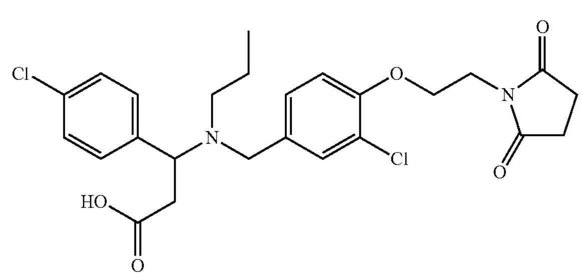 [SMILES: CCCN(Cc1ccc(OCCN2C(=O)CCC2=O)c(Cl)c1)C(CC(=O)O)c1ccc(Cl)cc1] | 507 | 2.46 (A) | 97.1 |

TABLE 3-continued

| Examples | Structure | (M + H)+ | Rt min. (system) | Purity (%) |
|---|---|---|---|---|
| 104. | Chiral | 533 | 2.65 (A) | 99.5 |
| 105. | 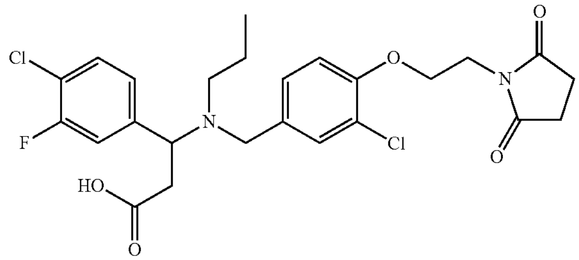 [SMILES: CCCN(Cc1ccc(OCCN2C(=O)CCC2=O)c(Cl)c1)C(CC(=O)O)c1ccc(Cl)c(F)c1] | 525 | 2.54 (A) | 97.0 |
| 106. | H—Cl | 553 | 2.65 (A) | 95.4 |
| 107. | 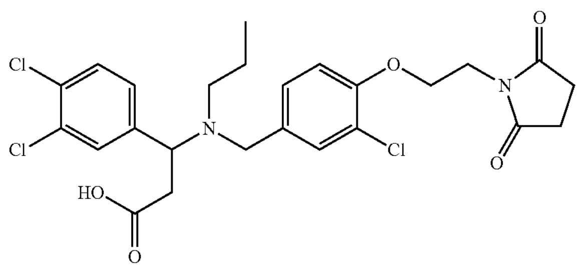 [SMILES: CCCN(Cc1ccc(OCCN2C(=O)CCC2=O)c(Cl)c1)C(CC(=O)O)c1ccc(Cl)c(Cl)c1] | 541 | 2.63 (A) | 98.0 |
| 108. | Chiral | 535 | 2.35 (A) | 83.9 |
| 109. | Chiral | 537 | 2.58 (A) | 92.7 |

TABLE 3-continued
| Examples | Structure | (M + H)⁺ | Rt min. (system) | Purity (%) |
|---|---|---|---|---|
| 110. | 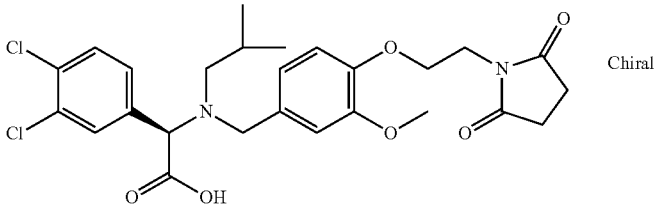 [SMILES: COc1cc(CN(CC(C)C)[C@@H](C(=O)O)c2ccc(Cl)c(Cl)c2)ccc1OCCN1C(=O)CCC1=O] Chiral | 537 | 2.58 (A) | 96.0 |
| 111. | 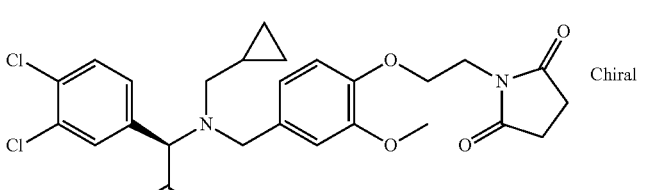 Chiral | 535 | 2.36 (A) | 89.9 |
| 112. | 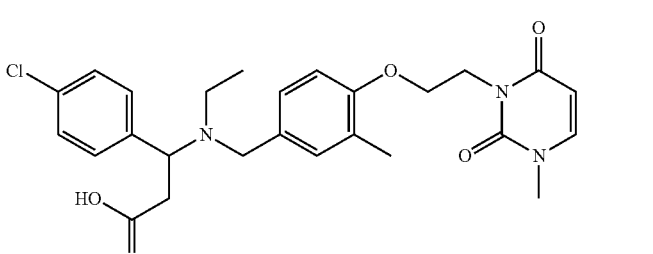 | 500 | 2.49 (A) | 95.8 |
| 113. | 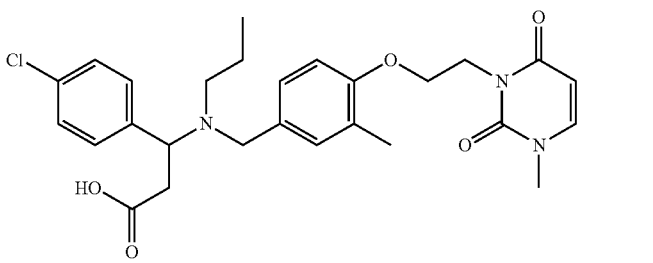 [SMILES: CCCN(Cc1ccc(OCCn2c(=O)ccn(C)c2=O)c(C)c1)C(CC(=O)O)c1ccc(Cl)cc1] | 514 | 2.63 (A) | 89.7 |
| 114. | 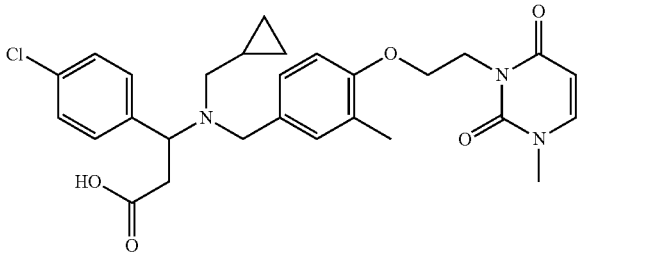 [SMILES: Cc1cc(CN(CC2CC2)C(CC(=O)O)c2ccc(Cl)cc2)ccc1OCCn1c(=O)ccn(C)c1=O] | 526 | 2.66 (A) | 88.2 |
| 115. | 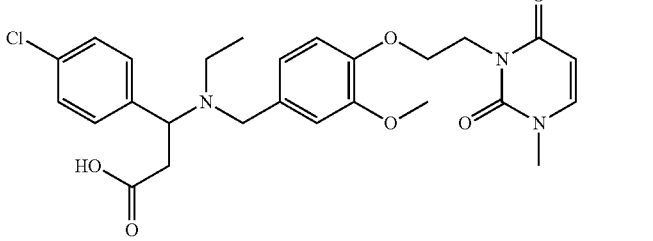 | 516 | 2.33 (A) | 90.5 |

TABLE 3-continued
| Examples | Structure | (M + H)+ | Rt min. (system) | Purity (%) |
|---|---|---|---|---|
| 116. | 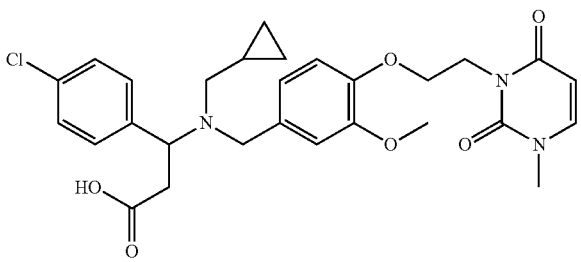 [SMILES: COc1cc(CN(CC2CC2)C(CC(=O)O)c2ccc(Cl)cc2)ccc1OCCn1c(=O)ccn(C)c1=O] | 542 | 2.50 (A) | 99.7 |
| 117. | 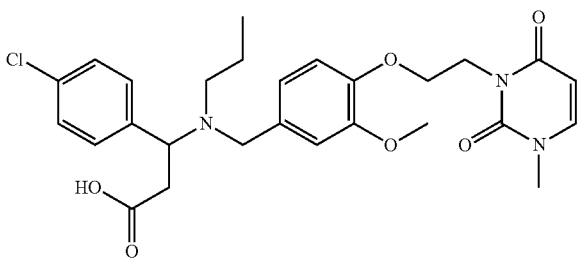 [SMILES: CCCN(Cc1ccc(OCCn2c(=O)ccn(C)c2=O)c(OC)c1)C(CC(=O)O)c1ccc(Cl)cc1] | 530 | 2.47 (A) | 99.2 |
| 118. | 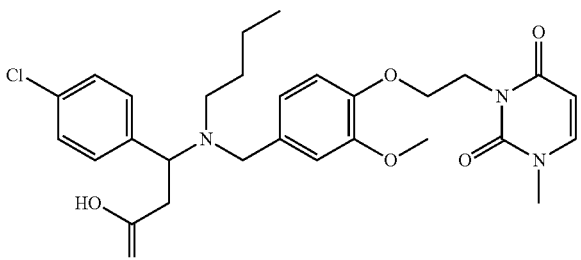 | 544 | 2.60 (A) | 99.5 |
| 119. | 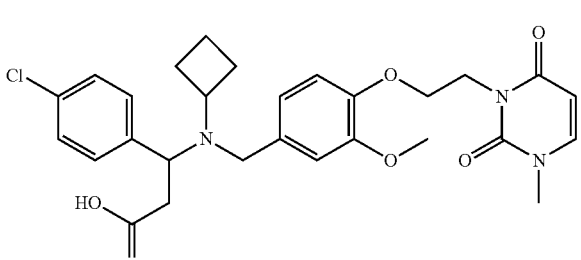 | 542 | 2.46 (A) | 97.2 |
| 120. | 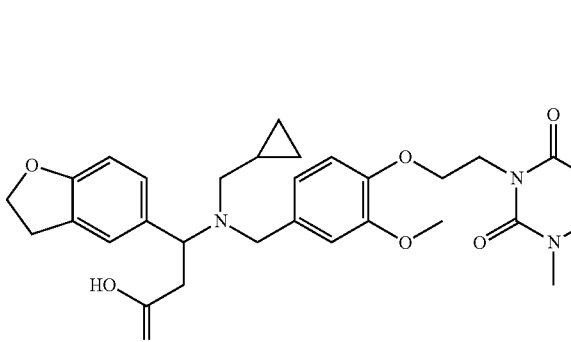 | 550 | 2.33 (A) | 91.0 |

TABLE 3-continued

| Examples | Structure | (M + H)+ | Rt min. (system) | Purity (%) |
|---|---|---|---|---|
| 121. | 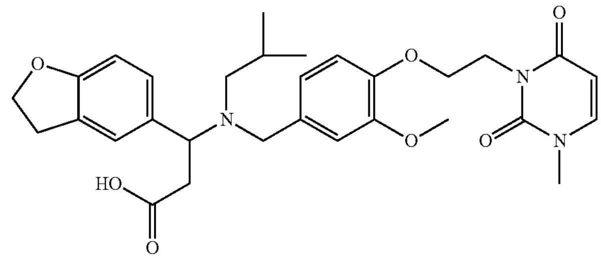 [SMILES: COc1cc(CN(CC(C)C)C(CC(=O)O)c2ccc3c(c2)CCO3)ccc1OCCn1c(=O)ccn(C)c1=O] | 552 | 2.45 (A) | 89.9 |
| 122. | 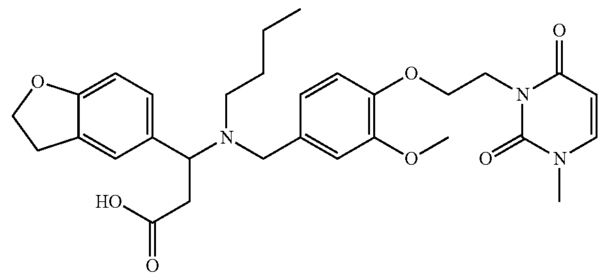 [SMILES: CCCCN(Cc1ccc(OCCn2c(=O)ccn(C)c2=O)c(OC)c1)C(CC(=O)O)c1ccc2c(c1)CCO2] | 552 | 2.43 (A) | 92.9 |
| 123. | 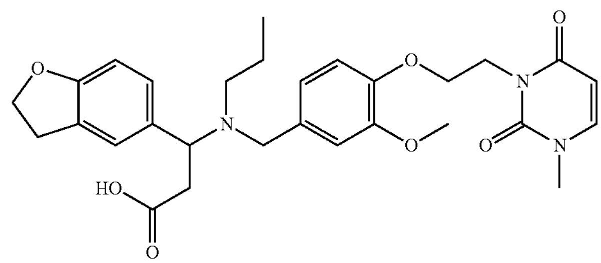 [SMILES: CCCN(Cc1ccc(OCCn2c(=O)ccn(C)c2=O)c(OC)c1)C(CC(=O)O)c1ccc2c(c1)CCO2] | 538 | 2.30 (A) | 93.4 |
| 124. | 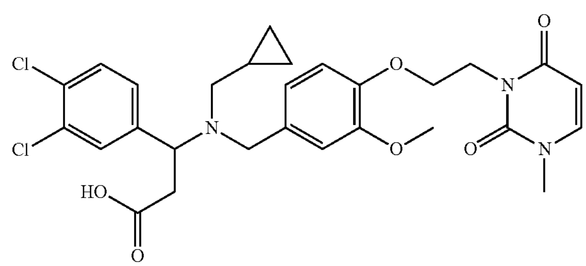 [SMILES: COc1cc(CN(CC2CC2)C(CC(=O)O)c2ccc(Cl)c(Cl)c2)ccc1OCCn1c(=O)ccn(C)c1=O] | 576 | 2.74 (A) | 97.7 |
| 125. | 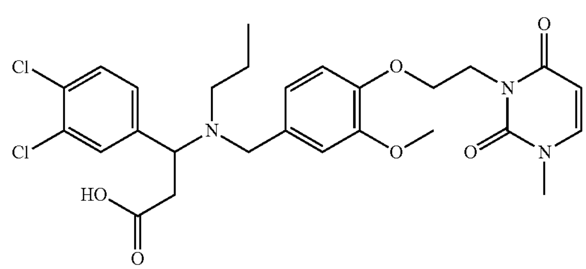 [SMILES: CCCN(Cc1ccc(OCCn2c(=O)ccn(C)c2=O)c(OC)c1)C(CC(=O)O)c1ccc(Cl)c(Cl)c1] | 564 | 2.69 (A) | 92.4 |

TABLE 3-continued

| Examples | Structure | (M + H)+ | Rt min. (system) | Purity (%) |
|---|---|---|---|---|
| 126. | 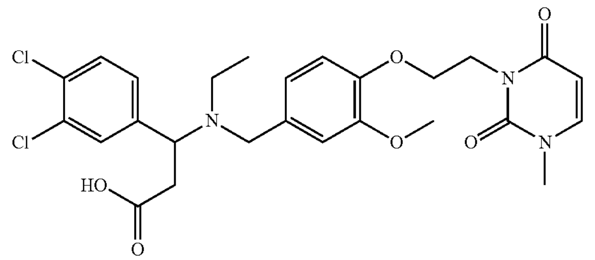 [SMILES: CCN(Cc1ccc(OCCn2c(=O)ccn(C)c2=O)c(OC)c1)C(CC(=O)O)c1ccc(Cl)c(Cl)c1] | 550 | 2.55 (A) | 97.1 |
| 127. | 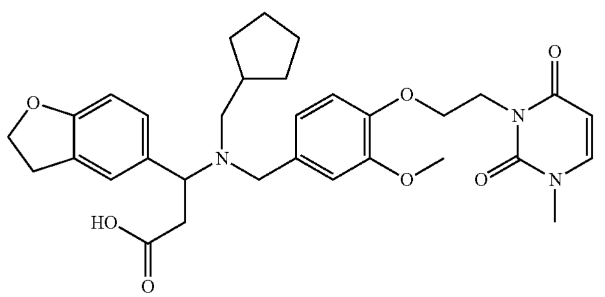 [SMILES: COc1cc(CN(CC2CCCC2)C(CC(=O)O)c2ccc3c(c2)CCO3)ccc1OCCn1c(=O)ccn(C)c1=O] | 578 | 2.49 (A) | 95.0 |
| 128. | 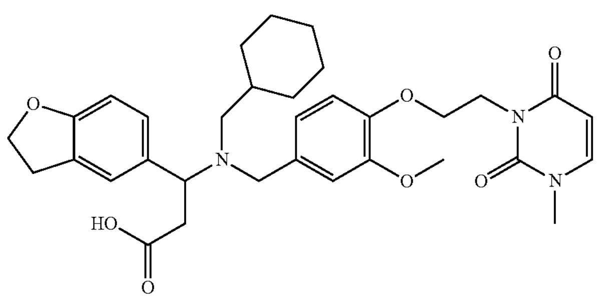 [SMILES: COc1cc(CN(CC2CCCCC2)C(CC(=O)O)c2ccc3c(c2)CCO3)ccc1OCCn1c(=O)ccn(C)c1=O] | 592 | 2.61 (A) | 96.9 |
| 129. | 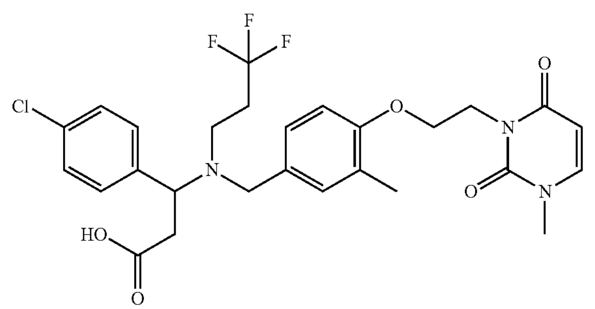 [SMILES: Cc1cc(CN(CCC(F)(F)F)C(CC(=O)O)c2ccc(Cl)cc2)ccc1OCCn1c(=O)ccn(C)c1=O] | 568 | 2.95 (A) | 97.1 |
| 130. | 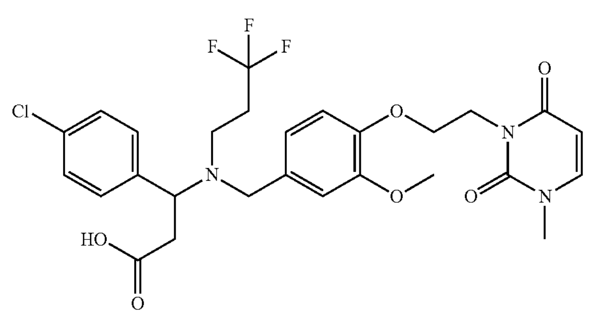 [SMILES: COc1cc(CN(CCC(F)(F)F)C(CC(=O)O)c2ccc(Cl)cc2)ccc1OCCn1c(=O)ccn(C)c1=O] | 584 | 2.87 (A) | 96.8 |

TABLE 3-continued
| Examples | Structure | (M + H)+ | Rt min. (system) | Purity (%) |
|---|---|---|---|---|
| 131. | 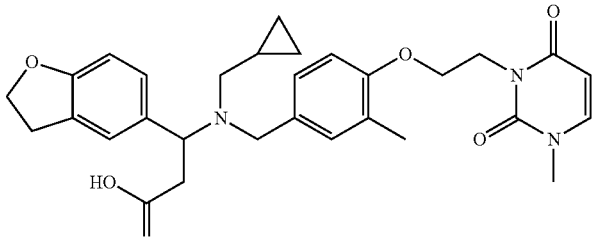 | 534 | 2.36 (A) | 90.9 |
| 132. | 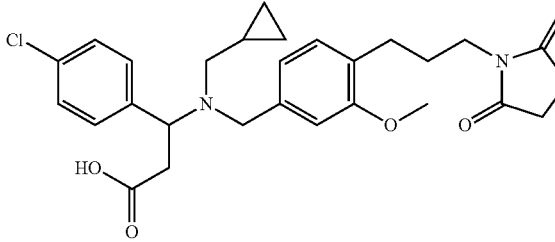 | 513 | 9.08 (B) | 86.5 |
| 133. | 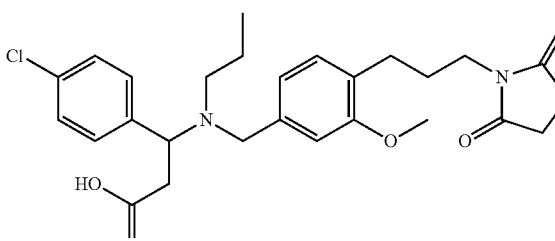 | 501 | 2.71 (A) | 90.3 |
| 134. | 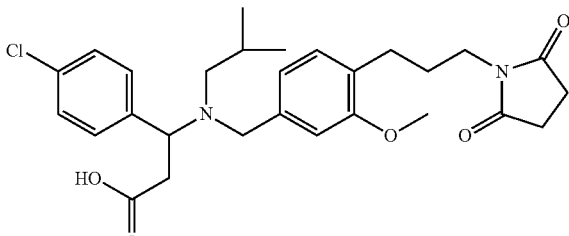 | 515 | 2.89 (A) | 95.8 |
| 135. | 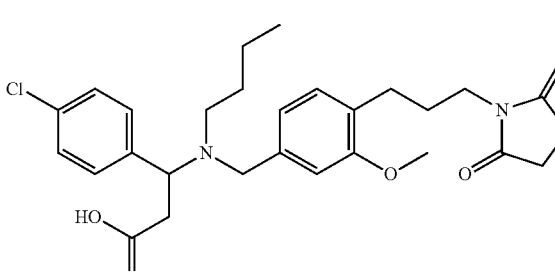 | 515 | 2.86 (A) | 89.5 |

TABLE 3-continued

| Examples | Structure | (M + H)+ | Rt min. (system) | Purity (%) |
|---|---|---|---|---|
| 136. | 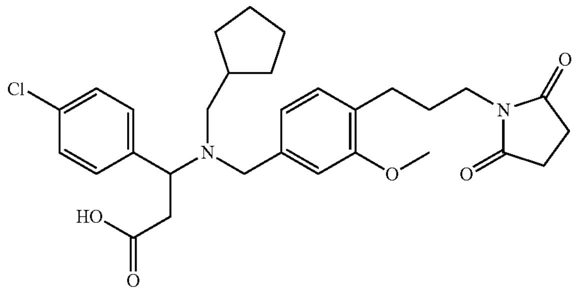 [SMILES: COc1cc(CN(CC2CCCC2)C(CC(=O)O)c2ccc(Cl)cc2)ccc1CCCN1C(=O)CCC1=O] | 540 | 3.02 (A) | 94.5 |
| 137. | 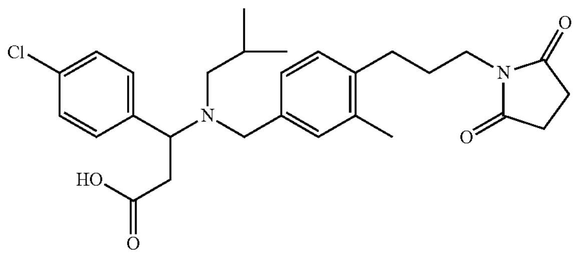 [SMILES: Cc1cc(CN(CC(C)C)C(CC(=O)O)c2ccc(Cl)cc2)ccc1CCCN1C(=O)CCC1=O] | 499 | 2.90 (A) | 96.8 |
| 138. | 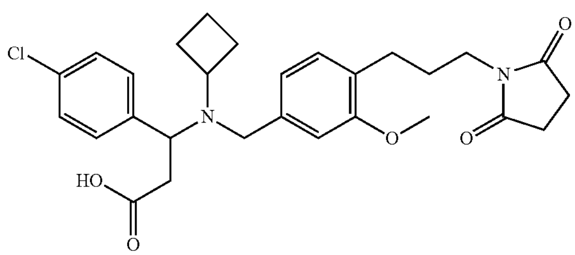 [SMILES: COc1cc(CN(C2CCC2)C(CC(=O)O)c2ccc(Cl)cc2)ccc1CCCN1C(=O)CCC1=O] | 513 | 3.22 (A) | 84.0 |
| 139. | 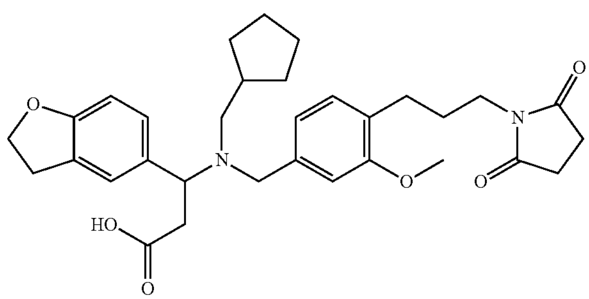 [SMILES: COc1cc(CN(CC2CCCC2)C(CC(=O)O)c2ccc3c(c2)CCO3)ccc1CCCN1C(=O)CCC1=O] | 549 | 2.98 (A) | 90.8 |
| 140. | 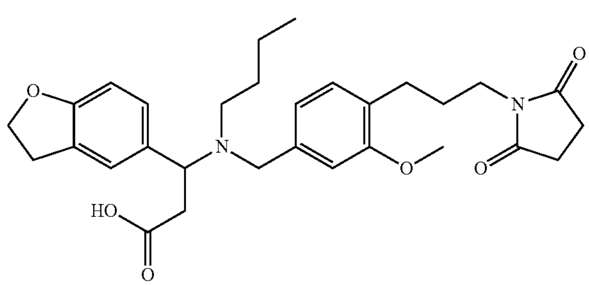 [SMILES: CCCCN(Cc1ccc(CCCN2C(=O)CCC2=O)c(OC)c1)C(CC(=O)O)c1ccc2c(c1)CCO2] | 523 | 2.78 (A) | 96.0 |

TABLE 3-continued

| Examples | Structure | (M + H)⁺ | Rt min. (system) | Purity (%) |
|---|---|---|---|---|
| 141. | 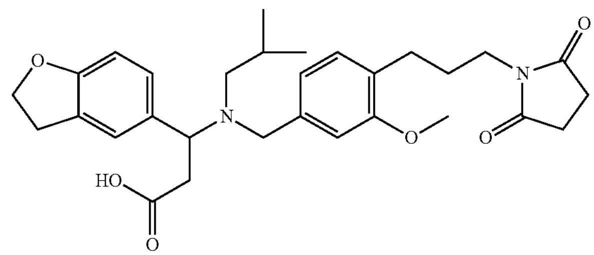 | 523 | 2.80 (A) | 95.0 |
| 142. | 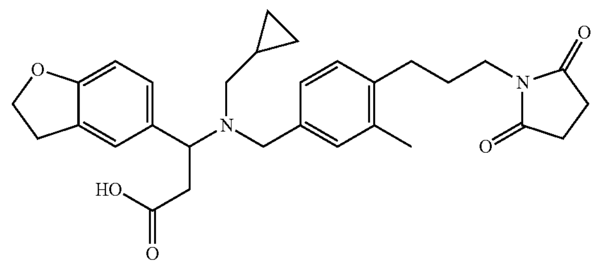 [SMILES: Cc1cc(CN(CC2CC2)C(CC(=O)O)c2ccc3c(c2)CCO3)ccc1CCCN1C(=O)CCC1=O] | 505 | 2.47 (A) | 93.4 |
| 143. | 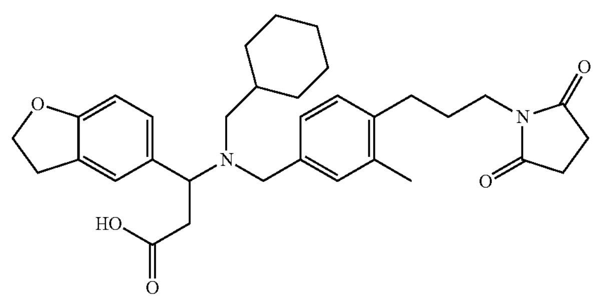 [SMILES: Cc1cc(CN(CC2CCCCC2)C(CC(=O)O)c2ccc3c(c2)CCO3)ccc1CCCN1C(=O)CCC1=O] | 547 | 2.87 (A) | 95.5 |
| 144. | 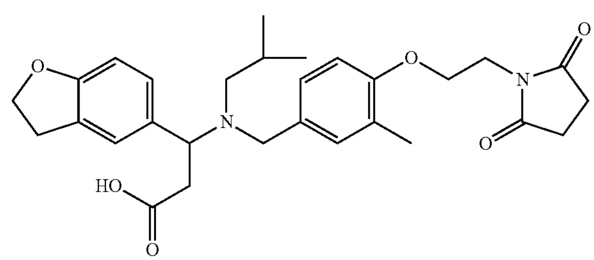 [SMILES: Cc1cc(CN(CC(C)C)C(CC(=O)O)c2ccc3c(c2)CCO3)ccc1OCCN1C(=O)CCC1=O] | 509 | 2.64 (A) | 93.0 |
| 145. | 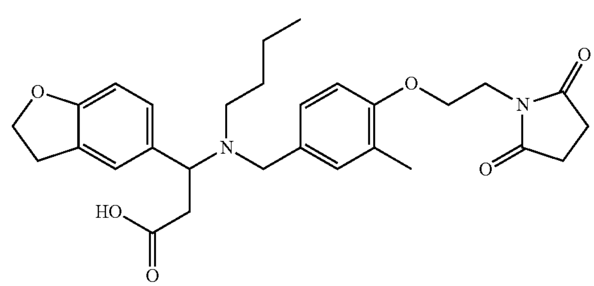 [SMILES: CCCCN(Cc1ccc(OCCN2C(=O)CCC2=O)c(C)c1)C(CC(=O)O)c1ccc2c(c1)CCO2] | 509 | 2.62 (A) | 95.2 |

TABLE 3-continued

| Examples | Structure | (M + H)+ | Rt min. (system) | Purity (%) |
|---|---|---|---|---|
| 146. | 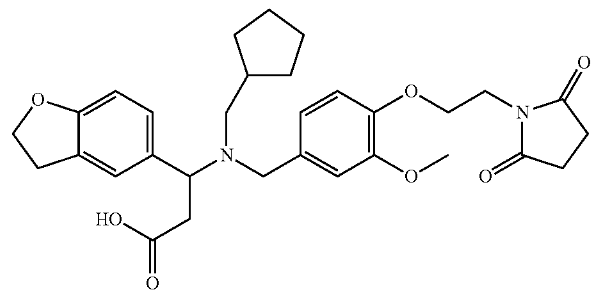 [SMILES: COc1cc(CN(CC2CCCC2)C(CC(=O)O)c2ccc3c(c2)CCO3)ccc1OCCN1C(=O)CCC1=O] | 551 | 2.62 (A) | 95.6 |
| 147. | 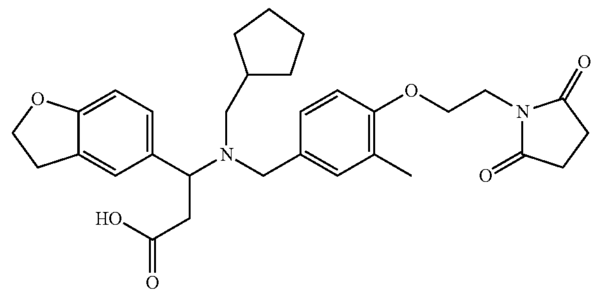 [SMILES: Cc1cc(CN(CC2CCCC2)C(CC(=O)O)c2ccc3c(c2)CCO3)ccc1OCCN1C(=O)CCC1=O] | 535 | 2.80 (A) | 98.4 |
| 148. | 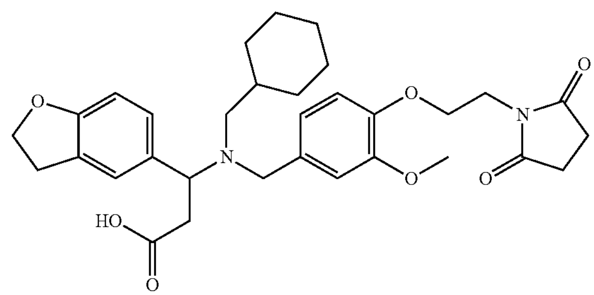 [SMILES: COc1cc(CN(CC2CCCCC2)C(CC(=O)O)c2ccc3c(c2)CCO3)ccc1OCCN1C(=O)CCC1=O] | 565 | 2.62 (A) | 90.2 |
| 149. | 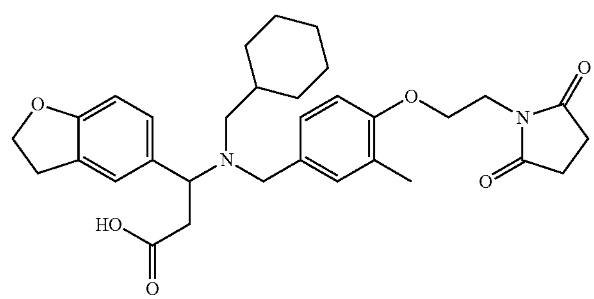 [SMILES: Cc1cc(CN(CC2CCCCC2)C(CC(=O)O)c2ccc3c(c2)CCO3)ccc1OCCN1C(=O)CCC1=O] | 549 | 2.81 (A) | 93.8 |
| 150. | 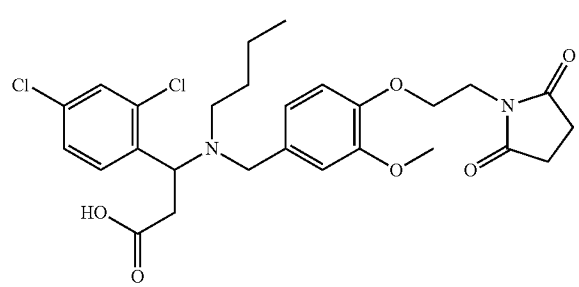 [SMILES: CCCCN(Cc1ccc(OCCN2C(=O)CCC2=O)c(OC)c1)C(CC(=O)O)c1ccc(Cl)cc1Cl] | 551 | 2.54 (A) | 93.3 |

TABLE 3-continued

| Examples | Structure | (M + H)+ | Rt min. (system) | Purity (%) |
|---|---|---|---|---|
| 151. | 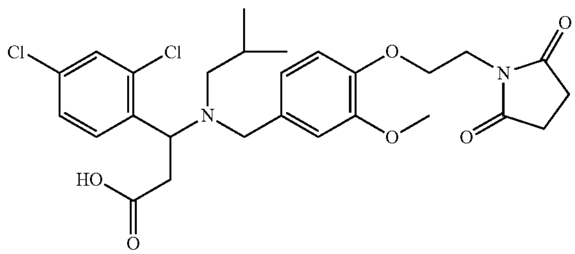 [SMILES: COc1cc(CN(CC(C)C)C(CC(=O)O)c2ccc(Cl)cc2Cl)ccc1OCCN1C(=O)CCC1=O] | 551 | 2.68 (A) | 95.2 |
| 152. | 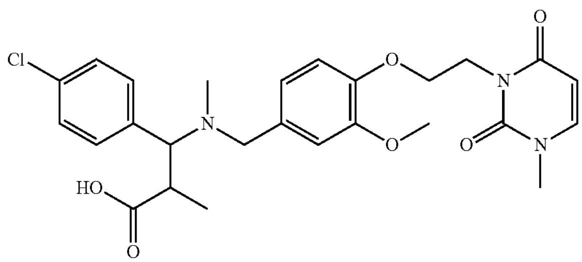 [SMILES: COc1cc(CN(C)C(c2ccc(Cl)cc2)C(C)C(=O)O)ccc1OCCn1c(=O)ccn(C)c1=O] | 516 | 2.21 and 2.40 (45% and 51%) (A) | 96.4 |
| 153. | 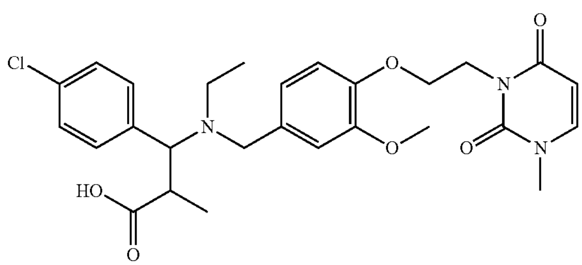 [SMILES: CCN(Cc1ccc(OCCn2c(=O)ccn(C)c2=O)c(OC)c1)C(c1ccc(Cl)cc1)C(C)C(=O)O] | 530 | 2.31 and 2.47 (68% and 30%) (A) | 98.4 |
| 154. | 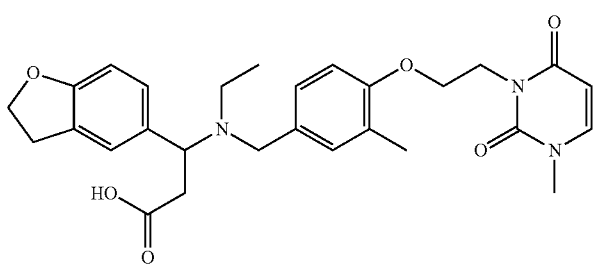 [SMILES: CCN(Cc1ccc(OCCn2c(=O)ccn(C)c2=O)c(C)c1)C(CC(=O)O)c1ccc2c(c1)CCO2] | 508 | 2.18 (A) | 99.0 |
| 155. | 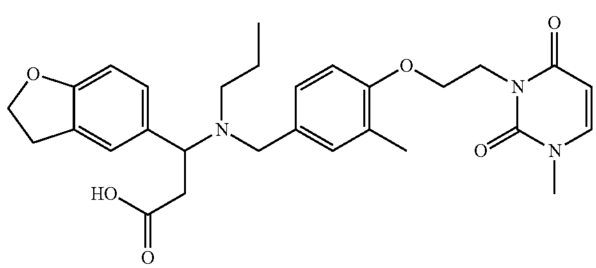 [SMILES: CCCN(Cc1ccc(OCCn2c(=O)ccn(C)c2=O)c(C)c1)C(CC(=O)O)c1ccc2c(c1)CCO2] | 522 | 2.32 (A) | 98.0 |

TABLE 3-continued

| Examples | Structure | (M + H)+ | Rt min. (system) | Purity (%) |
|---|---|---|---|---|
| 156. | 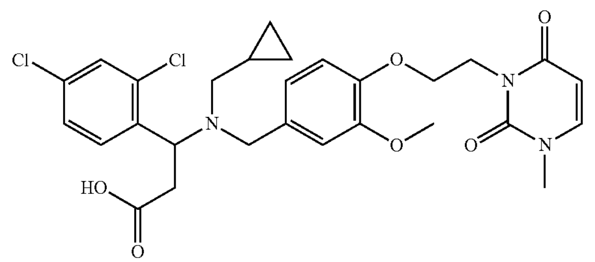 [SMILES: COc1cc(CN(CC2CC2)C(CC(=O)O)c2ccc(Cl)cc2Cl)ccc1OCCn1c(=O)ccn(C)c1=O] | 576 | 2.37 (A) | 96.5 |
| 157. | 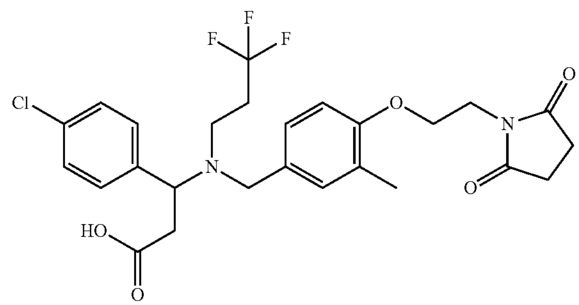 [SMILES: Cc1cc(CN(CCC(F)(F)F)C(CC(=O)O)c2ccc(Cl)cc2)ccc1OCCN1C(=O)CCC1=O] | 541 | 3.02 (A) | 91.4 |
| 158. | 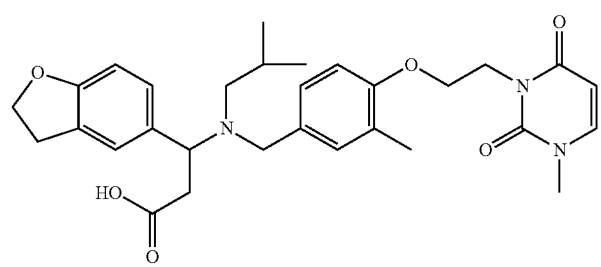 [SMILES: Cc1cc(CN(CC(C)C)C(CC(=O)O)c2ccc3c(c2)CCO3)ccc1OCCn1c(=O)ccn(C)c1=O] | 536 | 2.48 (A) | 96.6 |
| 159. | 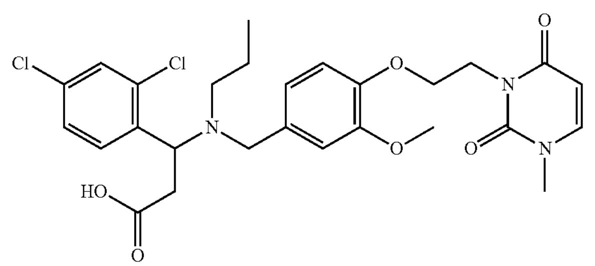 [SMILES: CCCN(Cc1ccc(OCCn2c(=O)ccn(C)c2=O)c(OC)c1)C(CC(=O)O)c1ccc(Cl)cc1Cl] | 564 | 2.37 (A) | 87.7 |
| 160. | 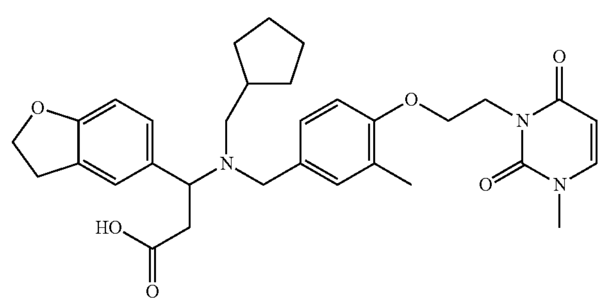 [SMILES: Cc1cc(CN(CC2CCCC2)C(CC(=O)O)c2ccc3c(c2)CCO3)ccc1OCCn1c(=O)ccn(C)c1=O] | 562 | 2.64 (A) | 96.3 |

TABLE 3-continued

| Examples | Structure | (M + H)⁺ | Rt min. (system) | Purity (%) |
|---|---|---|---|---|
| 161. | 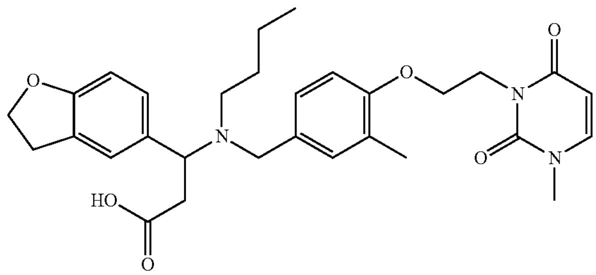 [SMILES: CCCCN(Cc1ccc(OCCn2c(=O)ccn(C)c2=O)c(C)c1)C(CC(=O)O)c1ccc2c(c1)CCO2] | 536 | 2.46 (A) | 95.9 |
| 162. | 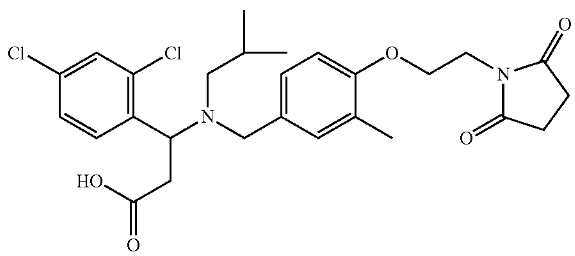 [SMILES: Cc1cc(CN(CC(C)C)C(CC(=O)O)c2ccc(Cl)cc2Cl)ccc1OCCN1C(=O)CCC1=O] | 535 | 2.82 (A) | 96.0 |
| 163. | 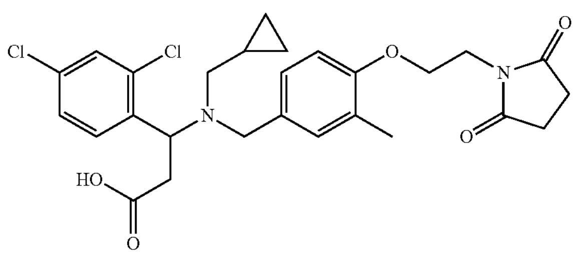 [SMILES: Cc1cc(CN(CC2CC2)C(CC(=O)O)c2ccc(Cl)cc2Cl)ccc1OCCN1C(=O)CCC1=O] | 533 | 2.55 (A) | 96.5 |
| 164. | 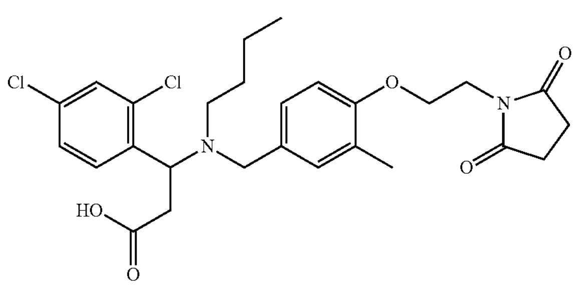 [SMILES: CCCCN(Cc1ccc(OCCN2C(=O)CCC2=O)c(C)c1)C(CC(=O)O)c1ccc(Cl)cc1Cl] | 535 | 5.11 (B) | 96.5 |
| 165. | 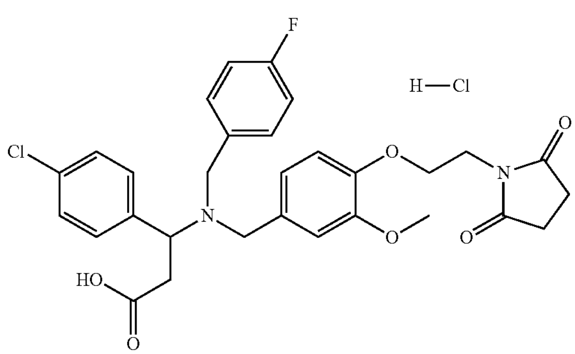 [SMILES: COc1cc(CN(Cc2ccc(F)cc2)C(CC(=O)O)c2ccc(Cl)cc2)ccc1OCCN1C(=O)CCC1=O ; Cl] | 569 | 2.87 (A) | 93.6 |

TABLE 3-continued
| Examples | Structure | (M + H)+ | Rt min. (system) | Purity (%) |
|---|---|---|---|---|
| 166. | 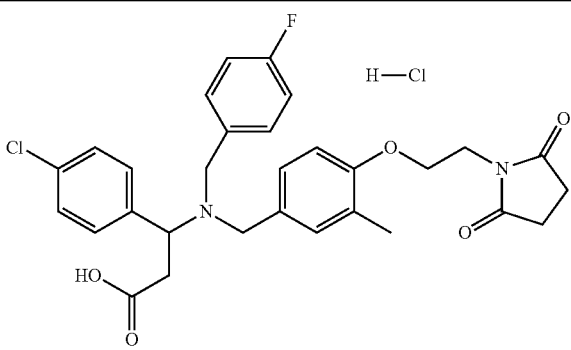 | 553 | 5.54 (B) | 96.7 |
| 167. | 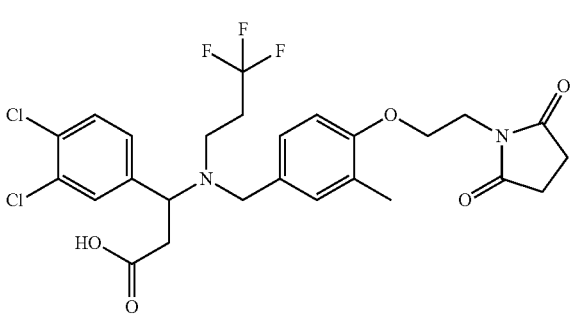 [SMILES: Cc1cc(CN(CCC(F)(F)F)C(CC(=O)O)c2ccc(Cl)c(Cl)c2)ccc1OCCN1C(=O)CCC1=O] | 575 | 3.46 (A) | 90.3 |
| 168. | 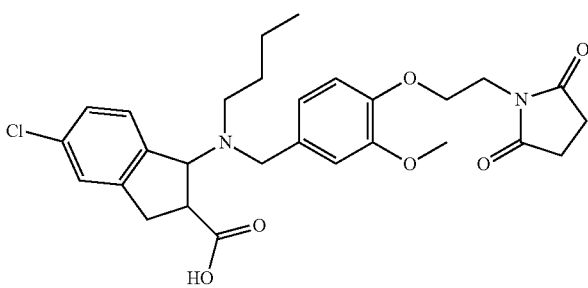 [SMILES: CCCCN(Cc1ccc(OCCN2C(=O)CCC2=O)c(OC)c1)C1c2ccc(Cl)cc2CC1C(=O)O] | 529 | 2.48 (A) | 97.2 |
| 169. | 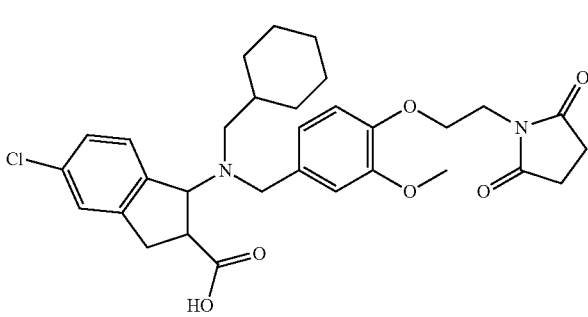 [SMILES: COc1cc(CN(CC2CCCCC2)C2c3ccc(Cl)cc3CC2C(=O)O)ccc1OCCN1C(=O)CCC1=O] | 569 | 2.89 (A) | 98.4 |
| 170. | 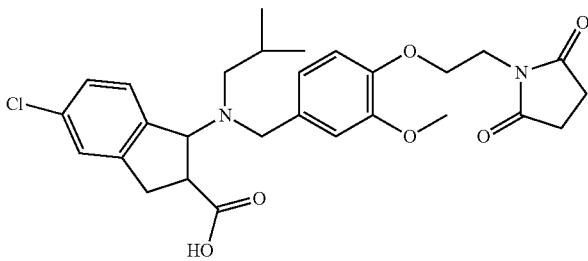 [SMILES: COc1cc(CN(CC(C)C)C2c3ccc(Cl)cc3CC2C(=O)O)ccc1OCCN1C(=O)CCC1=O] | 529 | 2.56 (A) | 97.0 |

TABLE 3-continued
| Examples | Structure | (M + H)⁺ | Rt min. (system) | Purity (%) |
|---|---|---|---|---|
| 171. | 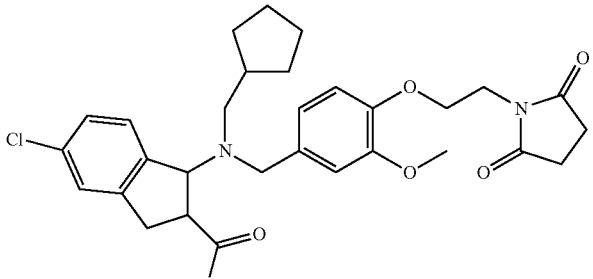 | 555 | 2.68 (A) | 91.0 |
| 172. | 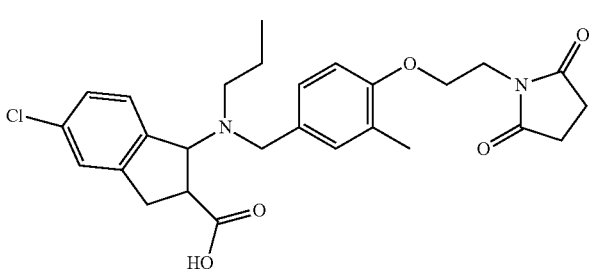 [SMILES: CCCN(Cc1ccc(OCCN2C(=O)CCC2=O)c(C)c1)C1c2ccc(Cl)cc2CC1C(=O)O] | 499 | 2.50 (A) | 97.1 |
| 173. | 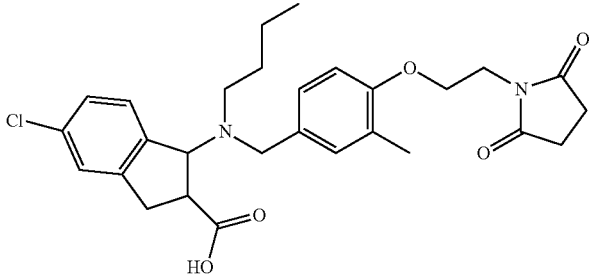 [SMILES: CCCCN(Cc1ccc(OCCN2C(=O)CCC2=O)c(C)c1)C1c2ccc(Cl)cc2CC1C(=O)O] | 513 | 2.61 (A) | 96.1 |
| 174. | 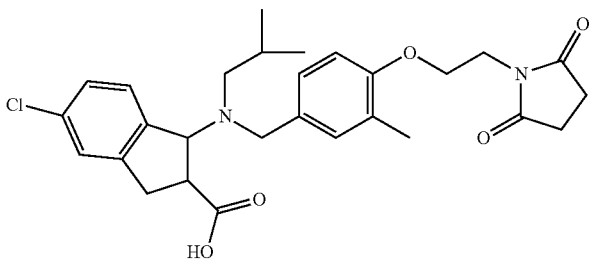 [SMILES: Cc1cc(CN(CC(C)C)C2c3ccc(Cl)cc3CC2C(=O)O)ccc1OCCN1C(=O)CCC1=O] | 513 | 2.68 (A) | 95.7 |
| 175. | 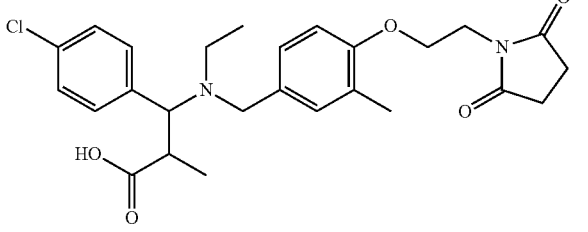 | 487 | 2.47 and 2.62 (20% and 78%) (A) | 98.5 |

TABLE 3-continued

| Examples | Structure | (M + H)+ | Rt min. (system) | Purity (%) |
|---|---|---|---|---|
| 176. | 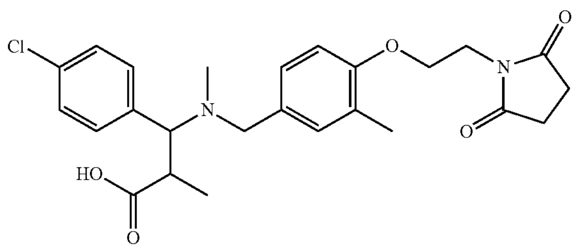 [SMILES: Cc1cc(CN(C)C(c2ccc(Cl)cc2)C(C)C(=O)O)ccc1OCCN1C(=O)CCC1=O] | 473 | 2.36 and 2.55 (93% and 6%) (A) | 99.5 |
| 177. | 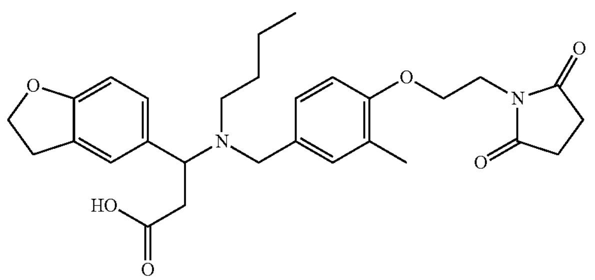 [SMILES: CCCCN(Cc1ccc(OCCN2C(=O)CCC2=O)c(C)c1)C(CC(=O)O)c1ccc2c(c1)CCO2] | 507 | 2.57 (A) | 93.8 |
| 178. | 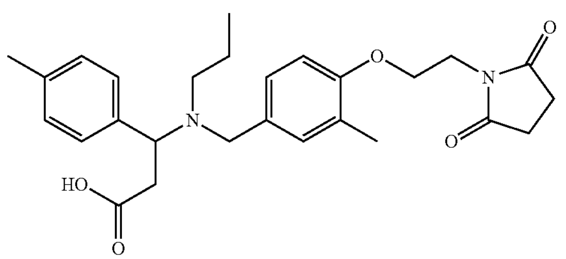 [SMILES: CCCN(Cc1ccc(OCCN2C(=O)CCC2=O)c(C)c1)C(CC(=O)O)c1ccc(C)cc1] | 467 | 2.45 (A) | 98.3 |
| 179. | 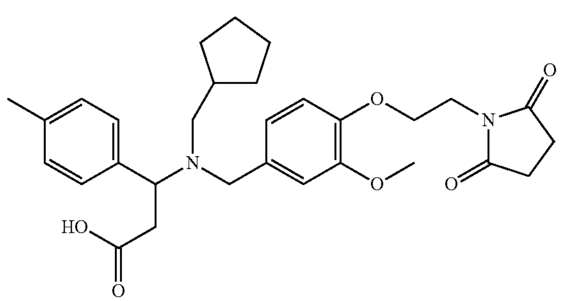 [SMILES: COc1cc(CN(CC2CCCC2)C(CC(=O)O)c2ccc(C)cc2)ccc1OCCN1C(=O)CCC1=O] | 523 | 2.61 (A) | 98.4 |
| 180. | 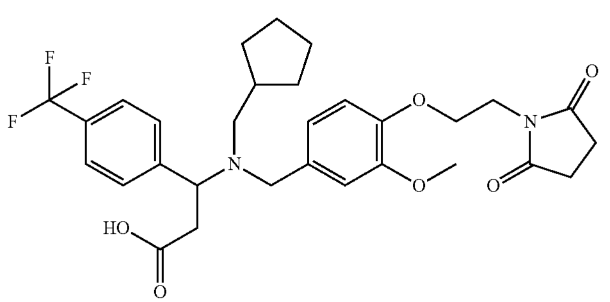 [SMILES: COc1cc(CN(CC2CCCC2)C(CC(=O)O)c2ccc(C(F)(F)F)cc2)ccc1OCCN1C(=O)CCC1=O] | 577 | 2.78 (A) | 98.5 |

TABLE 3-continued

| Examples | Structure | (M + H)⁺ | Rt min. (system) | Purity (%) |
|---|---|---|---|---|
| 181. | 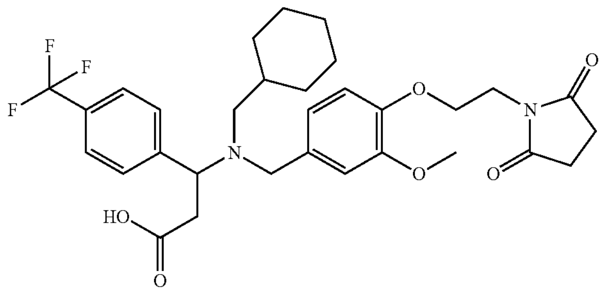 [SMILES: COc1cc(CN(CC2CCCCC2)C(CC(=O)O)c2ccc(C(F)(F)F)cc2)ccc1OCCN1C(=O)CCC1=O] | 591 | 2.91 (A) | 97.4 |
| 182. | 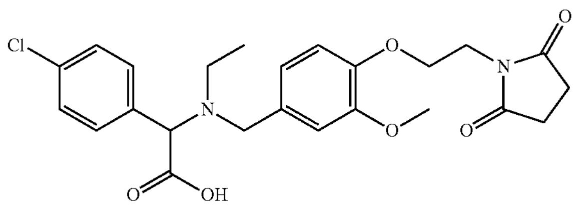 [SMILES: CCN(Cc1ccc(OCCN2C(=O)CCC2=O)c(OC)c1)C(C(=O)O)c1ccc(Cl)cc1] | 475 | 2.06 (A) | 91.3 |
| 183. | 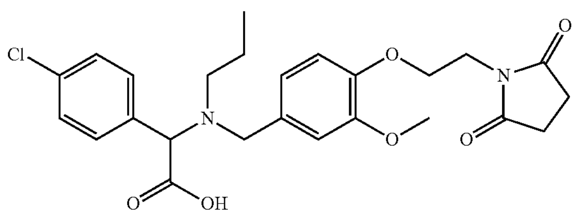 [SMILES: CCCN(Cc1ccc(OCCN2C(=O)CCC2=O)c(OC)c1)C(C(=O)O)c1ccc(Cl)cc1] | 489 | 2.20 (A) | 97.6 |
| 184. | 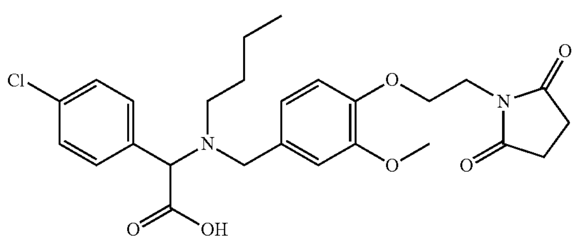 [SMILES: CCCCN(Cc1ccc(OCCN2C(=O)CCC2=O)c(OC)c1)C(C(=O)O)c1ccc(Cl)cc1] | 503 | 2.36 (A) | 98.2 |
| 185. | 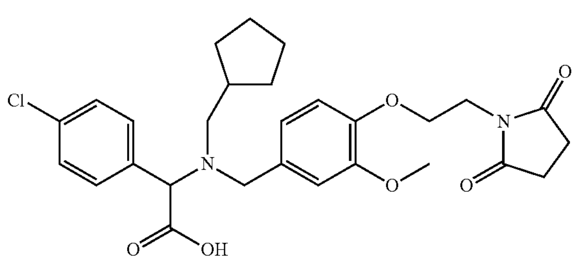 [SMILES: COc1cc(CN(CC2CCCC2)C(C(=O)O)c2ccc(Cl)cc2)ccc1OCCN1C(=O)CCC1=O] | 487 | 2.69 (A) | 87 |
| 186. | 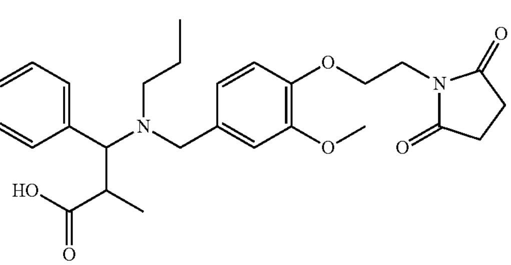 | 517 | 2.44 and 2.60 52% and 47% (A) | 99.3 |

TABLE 3-continued

| Examples | Structure | (M + H)+ | Rt min. (system) | Purity (%) |
|---|---|---|---|---|
| 187. | 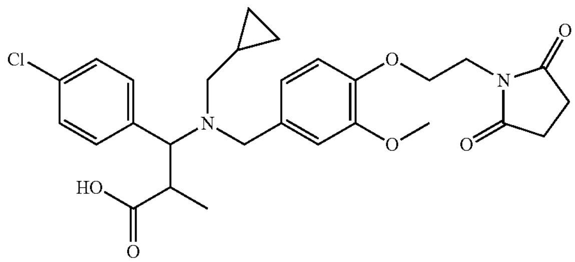 [SMILES: COc1cc(CN(CC2CC2)C(c2ccc(Cl)cc2)C(C)C(=O)O)ccc1OCCN1C(=O)CCC1=O] | 529 | 2.45 and 2.62 64% and 35% (A) | 99.3 |
| 188. | 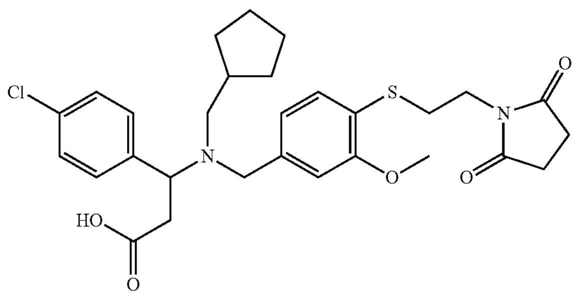 | 559 | 2.85 (A) | 99.9 |
| 189. | 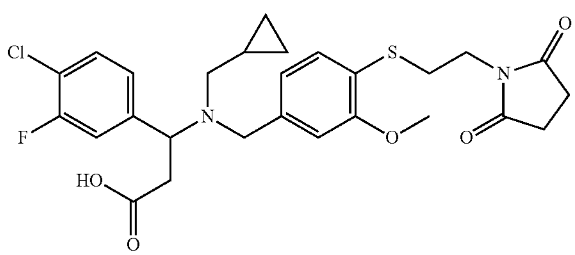 [SMILES: COc1cc(CN(CC2CC2)C(CC(=O)O)c2ccc(Cl)c(F)c2)ccc1SCCN1C(=O)CCC1=O] | 537 | 2.59 (A) | 99.9 |
| 190. | 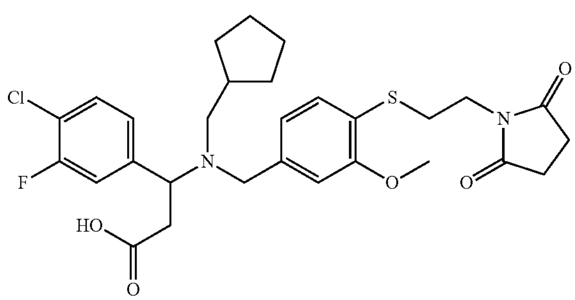 | 577 | 2.95 (A) | 99.2 |
| 191. | 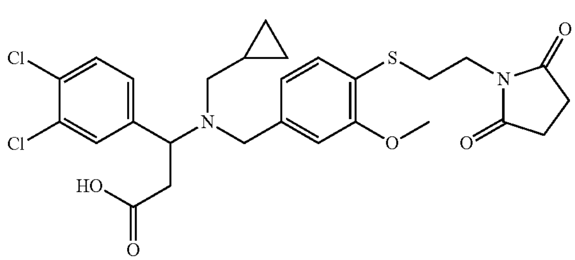 | 565 | 2.71 (A) | 99.0 |

TABLE 3-continued

| Examples | Structure | (M + H)+ | Rt min. (system) | Purity (%) |
|---|---|---|---|---|
| 192. | 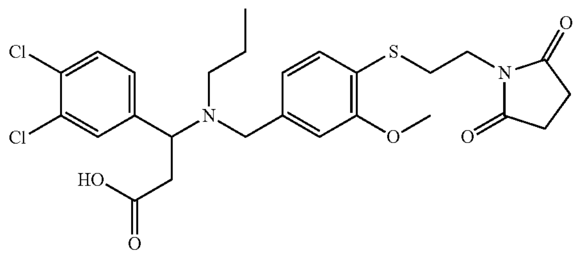 [SMILES: CCCN(Cc1ccc(SCCN2C(=O)CCC2=O)c(OC)c1)C(CC(=O)O)c1ccc(Cl)c(Cl)c1] | 553 | 2.69 (A) | 99.1 |
| 193. | 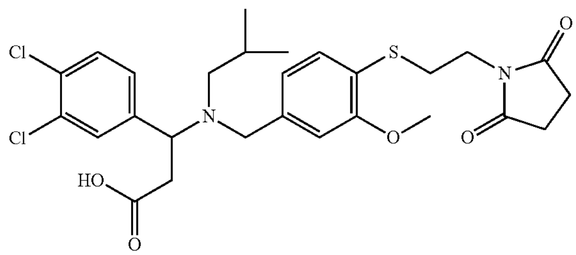 | 567 | 2.96 (A) | 98.4 |
| 194. | 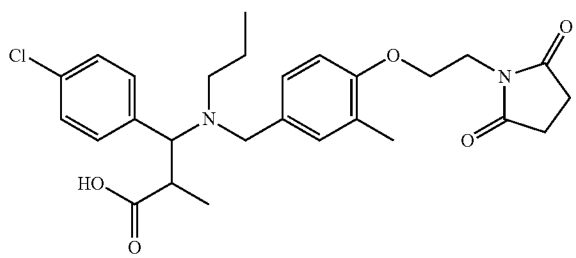 [SMILES: CCCN(Cc1ccc(OCCN2C(=O)CCC2=O)c(C)c1)C(c1ccc(Cl)cc1)C(C)C(=O)O] | 501 | 2.59 and 2.75 73% and 26% (A) | 98.8 |
| 195. | 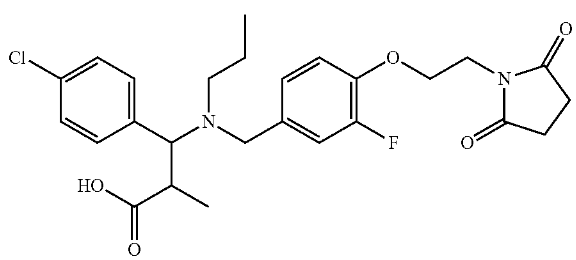 [SMILES: CCCN(Cc1ccc(OCCN2C(=O)CCC2=O)c(F)c1)C(c1ccc(Cl)cc1)C(C)C(=O)O] | 505 | 2.58 and 2.71 66% and 33% (A) | 99.1 |
| 196. | 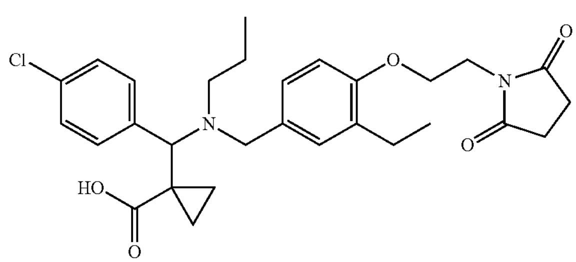 [SMILES: CCCN(Cc1ccc(OCCN2C(=O)CCC2=O)c(CC)c1)C(c1ccc(Cl)cc1)C1(C(=O)O)CC1] | 527 | 2.75 (A) | 99.2 |
| 197. | 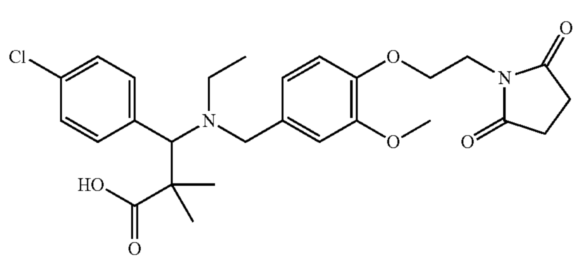 [SMILES: CCN(Cc1ccc(OCCN2C(=O)CCC2=O)c(OC)c1)C(c1ccc(Cl)cc1)C(C)(C)C(=O)O] | 551 | 2.63 (A) | 94.9 |

TABLE 3-continued
| Examples | Structure | (M + H)⁺ | Rt min. (system) | Purity (%) |
|---|---|---|---|---|
| 198. | 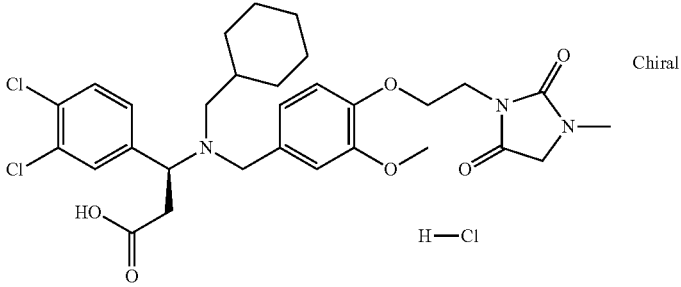 [SMILES: COc1cc(CN(CC2CCCCC2)[C@@H](CC(=O)O)c2ccc(Cl)c(Cl)c2)ccc1OCCN1C(=O)CN(C)C1=O ; Cl] | 590 | 3.02 (A) | 96.0 |
| 199. | 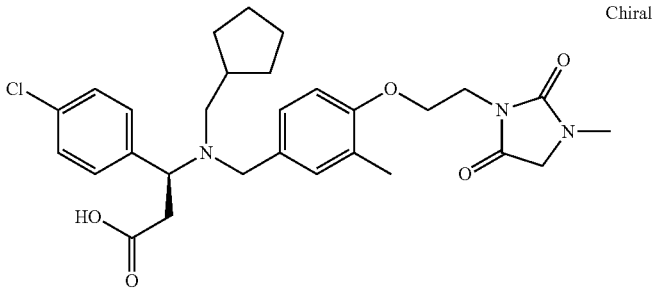 [SMILES: Cc1cc(CN(CC2CCCC2)[C@@H](CC(=O)O)c2ccc(Cl)cc2)ccc1OCCN1C(=O)CN(C)C1=O] | 542 | 2.73 (A) | 99.6 |
| 200. | 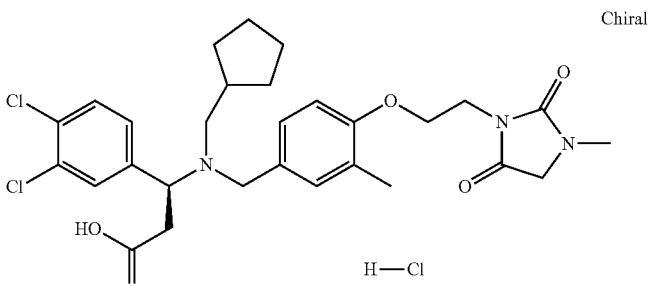 | 576 | 2.88 (A) | 94.0 |
| 201. | 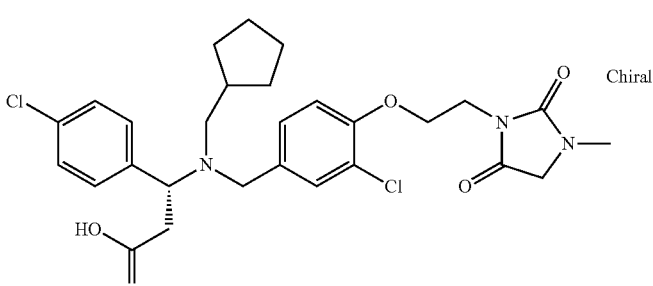 | 562 | 2.75 (A) | 99.8 |
| 202. | 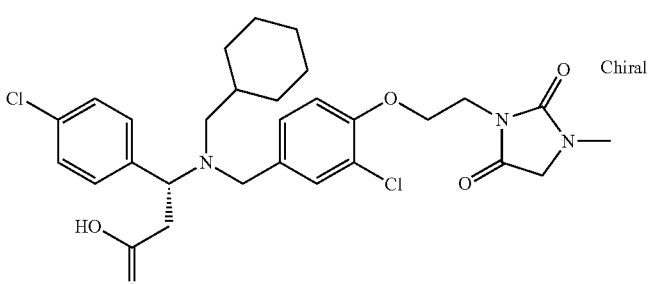 | 576 | 2.90 (A) | 98.7 |

TABLE 3-continued

| Examples | Structure | (M + H)+ | Rt min. (system) | Purity (%) |
|---|---|---|---|---|
| 203. | 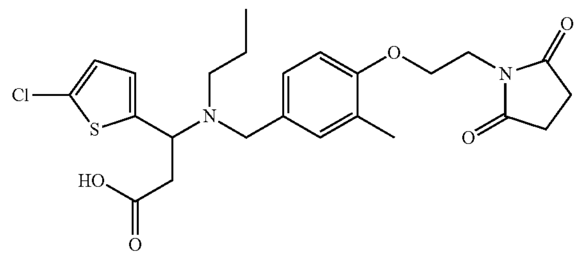 [SMILES: CCCN(Cc1ccc(OCCN2C(=O)CCC2=O)c(C)c1)C(CC(=O)O)c1ccc(Cl)s1] | 493 | 2.50 (A) | 95.0 |
| 204. | 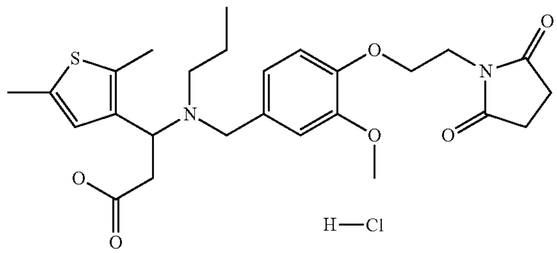 | 503 | 2.30 (A) | 90.7 |

Biological Methods

Compounds according to the invention as described are useful to block the interaction of CXCR3-A and CXCL10 in a radiolabelled binding assay.

Competition radioligand binding assays are performed to determine the in vitro potency of the newly synthesized, unlabeled test compounds to displace the specific binding of the radiolabelled endogenous chemokine, 125I-CXCL10, from the human CXCR3-A receptor. $IC_{50}$ values are determined for the test compounds and used to explore the structure-activity relationships (SAR). The established SAR is used to feed back the molecular design and to suggest some suitable modifications for groups and structural elements by which the affinity of test compounds for the human CXCR3 receptor would be improved.

Cell Line and Membrane Preparation

CHO cells stably expressing human recombinant CXCR3-A receptors are generated in Sanofi-Aventis (LIT Frankfurt) by transfection of Flp-In-CHO host cells with a plasmid construct of pCDA5-FRT-TO_IRES-Gai4qi4_DEST. This cell line is registered in Sanofi-Aventis cell line bank. Cells are grown in Ham's F12 (PAA) medium supplemented with 10% FCS (PAA, Cat No. E15-898) and 0.6% Hygromycin (PAA) in T175 flasks at 37° C. in a humidified incubator under 5% $CO_2$, 95% air. Cells are harvested from the culture flasks by a short treatment (8-10 minutes) with Versene (Gibco, Cat No. 15040). Cell suspension is diluted with PBS and cells are collected with centrifugation at 230 g for 10 minutes at 10° C. with a Juan centrifuge. Pellets containing approximately $1\times10^8$ cells are resuspended in 15 ml of 20 mM HEPES pH=7.4, 10 mM EDTA buffer supplemented with complete protease inhibitor (Roche, Cat No. 11 697 498 001). This suspension is homogenized with a teflon/glass homogenizer (Sartorius potter S) with 3×10 sec pulses in ice cold water bath, and then centrifuged at 300×g for 10 min at 4° C. with a Sigma centrifuge. The supernatant is carefully collected and centrifuged at 100,000×g for 60 min at 4° C. with a Beckman Avanti J30 centrifuge. The resulting pellet is washed once with 15 ml of fresh preparation buffer. The final membrane pellet is resuspended in storage buffer (20 mM HEPES pH=7.4, 0.1 mM EDTA, 250 mM sucrose supplemented with complete protease inhibitor) in a volume ratio of approximately $1\times10^8$ cells/1 ml, which gave a protein concentration of 2 to 4 mg/ml. Protein concentration is determined with Bio-Rad protein assay (Cat No 500-0006). Membrane aliquots were stored at −80° C. No degradation is observed until a storage period of approximately 5 months.

125I-CXCL10 Radioligand Binding Study

The composition of the binding assay buffer is determined in a course of detailed optimization procedure. This resulted in a binding assay buffer constituted by the following components: 25 mM Hepes (pH=7.4), 5 mM $MgCl_2$, 1 mM $CaCl_2$, 100 mM NaCl, supplemented with 0.1% of protease free BSA (as a final concentration). Competition binding assay is performed using 125I-CXCL10 (PerkinElmer, NEX348, specific activity 2200 Ci/mmol) radioligand in a final concentration of 50-70 pM. The nonspecific binding is defined by 150 pM of hr-CXCL10 (R&D Systems, Cat No 266-IP). The total assay volume is equal to 150 µl and contained 1% of DMSO (final concentration). Binding reaction is initiated by adding of membranes (10-20 µg proteins, approximately $5\times10^5$ cell equivalents) to the reaction mixture. After 60 minutes of incubation at 25° C. the reaction is terminated by rapid filtration over GF/B glass fibre filters that are pre-soaked with 0.5% polyethyleneimine (Fluka Analytical, P3143) for 1 hour, using a Skatron cell harvester device. Filters then are washed with 8 ml of ice-cold wash buffer (modified binding buffer in which BSA is omitted and the concentration of NaCl is adjusted to 500 mM concentration). The radioactivity retained on the filters is measured by a Wizard 1470 Automatic Gamma counter.

Test compounds are dissolved prior to the binding assay at a concentration of 10 mM in DMSO. Stock solutions are stored at −20° C. for not longer than 3 months. On the day of binding assay serial dilutions of test compounds ranging from 10 mM up to $3\times10^{-7}$ M (or $3\times10^{-9}$ M) are generated by 8 (or 12) consecutive steps using DMSO as solvent. Before adding these solutions of test compound to the binding reaction mixture, an intermediate dilution procedure is applied, in which 30 µl of each solution sample is transferred into a dilution tube containing 970 µl of binding assay buffer. Then 50 µl of these second dilution series is added to the test tubes and a concentration range of test compounds between $1\times10^{-5}$ M and $3\times10^{-9}$ M (or $3\times10^{-11}$ M) was generated.

The $IC_{50}$ values and Hill slopes for competition binding data are obtained using nonlinear four-parametric curve fitting method.

The exemplified compounds of the present invention have activities in the above binding assay of less than 20 micromolar, more particularly less than 1 micromolar, and further particularly less than 200 nanomolar 1050. Compounds listed in Table 4 are measured.

TABLE 4

| Example # | IC50 (nM) |
|---|---|
| 1.1 | 686 |
| 1 | 41 |
| 2 | 34 |
| 3 | 120 |
| 4 | 94 |
| 5 | 23 |
| 6 | 108 |
| 7 | 95 |
| 8 | 677 |
| 9 | 11 |
| 10 | 130 |
| 11 | 19 |
| 12 | 69 |
| 13 | 97 |
| 14 | 374 |
| 15 | 40 |
| 16 | 130 |
| 17 | 54 |
| 18 | 454 |
| 19 | 58 |
| 20 | 282 |
| 21 | 66 |
| 22 | 531 |
| 23 | 42 |
| 24 | 32 |
| 25 | 59 |
| 26 | 39 |
| 27 | 86 |
| 28 | 66 |
| 29 | 31 |
| 30 | 55 |
| 31 | 416 |
| 32 | 69 |
| 33 | 86 |
| 34 | 83 |
| 35 | 75 |
| 36 | 20 |
| 37 | 20 |
| 38 | 45 |
| 39 | 71 |
| 40 | 40 |
| 41 | 107 |
| 42 | 70 |
| 43 | 23 |
| 44 | 43 |
| 45 | 66 |
| 46 | 118 |
| 47 | 143 |
| 48 | 61 |
| 49 | 61 |
| 50 | 98 |
| 51 | 133 |
| 52 | 990 |
| 53 | 125 |
| 54 | 306 |
| 55 | 294 |
| 56 | 52 |
| 57 | 212 |
| 58 | 183 |
| 59 | 109 |
| 60 | 243 |
| 61 | 334 |
| 62 | 503 |
| 63 | 303 |
| 64 | 456 |
| 65 | 186 |
| 66 | 435 |
| 67 | 424 |
| 68 | 118 |
| 69 | 74 |
| 70 | 61 |
| 71 | 54 |
| 72 | 71 |
| 73 | 81 |
| 74 | 34 |
| 75 | 25 |
| 76 | 54 |
| 77 | 61 |
| 78 | 72 |
| 79 | 116 |
| 80 | 81 |
| 81 | 100 |
| 82 | 119 |
| 83 | 302 |
| 84 | 45 |
| 85 | 58 |
| 86 | 12 |
| 87 | 31 |
| 88 | 70 |
| 89 | 51 |
| 90 | 50 |
| 91 | 56 |
| 92 | 66 |
| 93 | 79 |
| 94 | 71 |
| 95 | 144 |
| 96 | 78 |
| 97 | 81 |
| 98 | 130 |
| 99 | 120 |
| 100 | 464 |
| 101 | 292 |
| 102 | 83 |
| 103 | 170 |
| 104 | 145 |
| 105 | 211 |
| 106 | 223 |
| 107 | 570 |
| 108 | 200 |
| 109 | 495 |
| 110 | 786 |
| 111 | 420 |
| 112 | 428 |
| 113 | 123 |
| 114 | 91 |
| 115 | 440 |
| 116 | 91 |
| 117 | 132 |
| 118 | 69 |
| 119 | 152 |
| 120 | 96 |
| 121 | 146 |
| 122 | 122 |
| 123 | 154 |
| 124 | 30 |
| 125 | 72 |
| 126 | 310 |
| 127 | 38 |
| 128 | 118 |
| 129 | 2150 |
| 130 | 1250 |
| 131 | 42 |
| 132 | 192 |
| 133 | 177 |
| 134 | 296 |
| 135 | 116 |

TABLE 4-continued

| Example # | IC50 (nM) |
|---|---|
| 136 | 179 |
| 137 | 240 |
| 138 | 190 |
| 139 | 54 |
| 140 | 51 |
| 141 | 43 |
| 142 | 211 |
| 143 | 211 |
| 144 | 80 |
| 145 | 38 |
| 146 | 56 |
| 147 | 46 |
| 148 | 28 |
| 149 | 72 |
| 150 | 140 |
| 151 | 110 |
| 152 | 754 |
| 153 | 635 |
| 154 | 58 |
| 155 | 529 |
| 156 | 120 |
| 157 | 650 |
| 158 | 75 |
| 159 | 354 |
| 160 | 81 |
| 161 | 76 |
| 162 | 263 |
| 163 | 162 |
| 164 | 133 |
| 165 | 75 |
| 166 | 78 |
| 167 | 2440 |
| 168 | 237 |
| 169 | 407 |
| 170 | 345 |
| 171 | 389 |
| 172 | 1350 |
| 173 | 603 |
| 174 | 800 |
| 175 | 266 |
| 176 | 5520 |
| 177 | 255 |
| 178 | 183 |
| 179 | 91 |
| 180 | 198 |
| 181 | 507 |
| 182 | 3900 |
| 183 | 256 |
| 184 | 336 |
| 185 | 467 |
| 186 | 73 |
| 187 | 71 |
| 188 | 31 |
| 189 | 40 |
| 190 | 62 |
| 191 | 20 |
| 192 | 55 |
| 193 | 72 |
| 194 | 272 |
| 195 | 342 |
| 196 | 630 |
| 197 | 295 |
| 198 | 187 |
| 199 | 175 |
| 200 | 234 |
| 201 | 886 |
| 202 | 810 |
| 203 | 105 |
| 204 | 197 |

Cyclic AMP Accumulation Assay

An in vitro functional assay measuring the changes in the intracellular cyclic adenosine 3',5'-monophosphate (cyclic AMP, or also called as cAMP) level following either stimulation or activation of CXCR3-A receptor is used to demonstrate the antagonistic functionality of the selected compounds.

Cyclic AMP is one of the most important intracellular second messenger molecules whose level is regulated principally by the G-protein coupled adenylyl cyclase effector enzyme located in the inner surface of the cellular plasma membrane. Receptor dependent, G-protein mediated changes in the cyclic AMP concentration elicit then complex regulatory processes within the cell such as activation of multiple protein kinases and phospholipases, generation of inositol triphosphate and transient rise in the intracellular calcium ion (Ca2+) concentration, ion channel gating, effects on different gene transcriptions.

Upon agonist stimulation, CXCR3-A receptor activates the pertussis toxin (PTX) sensitive G-proteins of the Gi class that mediates a reduction in the intracellular cAMP levels, an increase in the intracellular Ca2+ mobilization and actin polymerization, that finally lead to cytoskeletal rearrangement and directed cell migration (chemotaxis). [Sauty A et al, 2001. J. Immunol. 167: 7084-7093.]

Cyclic AMP accumulation assay is performed with a homogeneous time-resolved fluorescence (HTRF) cAMP femto 2 kit from CisBio International. The measurement is basically carried out by following the manufacturer's instructions.

Since CXCR3-A receptor is coupled to Gi-protein, thus an agonist activation of the receptor will lead to a decrease in the intracellular cAMP level [Crosignani S. et al, 2010. Bioorg. Med. Chem Letters, 20:3614-3617]. Therefore, the cells have to be preactivated by forskolin, a direct activator of the cell adenylyl cyclase enzyme, in order to reach a sufficient cellular basal cAMP level. The agonist induced decrease in cAMP level will be measured by an increase of the Fluorescence Resonance Energy Transfer signal, as the signal is inversely proportional to the concentration of cAMP in the cell.

For the assay, the adherent hr-CXCR3-Flp-In-CHO-IRES-Gai4qi4 cells (the same cell line as used for binding assay) are washed with Ca2+-Mg2+ free PBS and harvested by a short treatment with Acutase (Sigma, A6964). At a time point of 2 min after adding Acutase (3 ml/T175 flask) 7 ml of culture medium is added to the detached cells. Cell suspension is collected and centrifuged at 1,700 rpm for 10 min. (Sigma 2-S table centrifuge). The resulting cell pellet is resuspended in PBS with Ca2+/Mg2+(Invitrogen 14080-048) and subjecting to a second centrifugation step as above. The final cell pellet is resuspended in assay buffer (PBS with Ca2+/Mg2+, supplemented with fatty acid free BSA (Sigma A6003) at a final concentration of 1 mg/ml and with the phosphodiesterase inhibitor Rolipram (Calbiochem 557330) at a final concentration of 10 µM. Cells are transferred to a 96-well microplate (Costar 3694, Half Area flat bottom, non-treated, black polystyrene plate) at a density of 16,000 cells/well.

The cells are incubated in the presence of different concentrations of antagonist compounds (within the range of 10 µM and 0.1 nM) for 10 min at room temperature (R.T.) under continuous shaking the microplate in a plate shaker (Heidolph Titramax 100, at 600 rpm). The final concentration of DMSO in reaction mixture is 0.1%. Then CXCL10 at a final concentration of 20 nM is added and the cells are further incubated for 10 min at R.T., as above. After that forskolin (Sigma F-6886) at 1 µM final concentration is added and an additional incubation period (30 min, R.T., shaking) followed. The final reaction volume is 40 µl. The reaction is stopped by adding the lysis buffer containing the HTRF reagents.

Plates are then incubated for 60 min at R.T. under shaking, and time-resolved FRET signals are measured after excitation at 337 nm. Both the emission signal from the europium cryptate-labelled anti-cAMP antibody (620 nm) and the FRET signal resulting from the labelled cAMP-d2 (665 nm) are recorded using a RubyStar instrument (BMG Labtechnologies).

The results are calculated as a fluorescence ratio (Em.665 nm/Em.620 nm)×10000 and are analysed by calculating the Delta F value which corresponded to the following formula:

DeltaF=(Standard or Sample Ratio−Negative Control Ratio)/(Negative Control Ratio)×100.

The negative control corresponded to the background signal obtained with the cryptate conjugate alone.

FORMULATION EXAMPLES (1) Tablets

The ingredients below are mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below are mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below are mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

The compounds of the present invention have CXCR3 inhibitory activity and are useful as an active ingredient of a medicament for preventive and/or therapeutic treatment of a disease caused by abnormal activation of CXCR3 such as COPD, psoriasis, graft/transplant rejection, ophthalmological disease, celiac disease, inflammatory bowel disease (IBD), type 1 diabetes, myasthenia gravis (MG), multiple sclerosis (MS) and other neuroinflammatory diseases, lupus, rheumatoid arthritis (RA) or lichen planus.

What we claim is:

1. A compound of formula 1

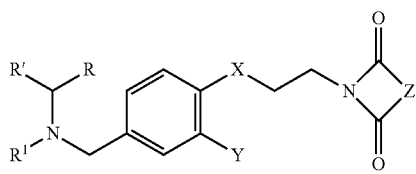

wherein

R represents hydrogen, $-C_{1-4}$ alkyl, $-C_{3-8}$ cycloalkyl, $-C_{1-4}$ halogenalkyl or halogenphenyl group;

R' represents hydrogen or

R and R' represent together with the carbon atom attached a $C_4$ aliphatic ring; and $R^1$ represents a group selected from the group consisting of

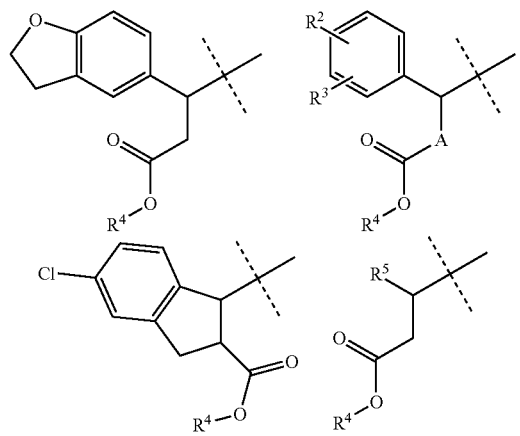

wherein

A represents a direct bond or $CH_2$, $CH(CH_3)$, $C(CH_3)_2$ or $C(CH_2)_2$ group;

$R_2$ represents Cl, Me or $-CF_3$;

$R_3$ represents hydrogen, Cl or F;

$R_4$ represents hydrogen or a $-C_{1-4}$ alkyl group;

$R_5$ represents a heteroaryl group selected from the group consisting of

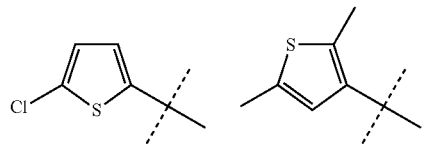

X represents O, S or $CH_2$;

Y represents hydrogen, halogen or a $-C_{1-4}$ alkyl, $-C_{1-4}$ alkoxy or $-C_{1-4}$ hydroxyalkyl group; and Z represents a $C_{1-4}$ aliphatic hydrocarbon bridge optionally containing one double bond, and/or one or more heteroatom selected from O, S, NH and $N(CH_3)$ or represents a $C_{2-4}$ aliphatic hydrocarbon bridge optionally containing N fused with a $C_{3-6}$ cycloalkyl ring optionally containing one or more double bonds or with a phenyl ring or represents a $C_{1-4}$ aliphatic hydrocarbon bridge substituted with a spiro $C_{3-6}$ cycloalkyl ring optionally containing one or more double bonds;

or a pharmaceutically acceptable salt thereof, stereoisomer thereof or a pharmaceutically acceptable salt of the stereoisomer.

2. A compound according to claim 1 wherein

R represents hydrogen or a $-C_{1-4}$ alkyl, $-C_{3-8}$ cycloalkyl, $-C_{1-4}$ halogenalkyl or halogenphenyl group;

R' represents hydrogen or

R and R' represent together with the carbon atom attached a $C_4$ aliphatic ring;

$R^1$ represents a group selected from the group consisting of

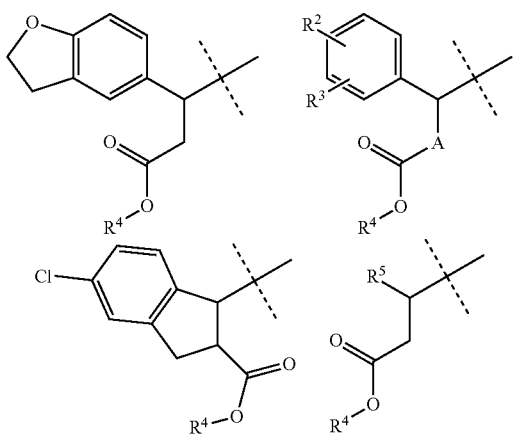

wherein
A represents a direct bond or a $CH_2$, $CH(CH_3)$, $C(CH_3)_2$ or $C(CH_2)_2$ group;
$R_2$ represents Cl, Me or —$CF_3$;
$R_3$ represents hydrogen, Cl or F;
$R_4$ represents hydrogen or a —$C_{1-4}$ alkyl group;
$R_5$ represents heteroaryl group selected from the group consisting of

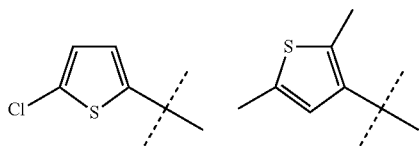

X represents O, S or $CH_2$;
Y represents a halogen or a —$C_{1-4}$ alkyl or —$C_{1-4}$ alkoxy group; and
Z represents a $(CH_2)_2$, $CH_2N(CH)_3$ or $CH=CH—N(CH_3)$ group.

3. A compound according to claim 1, wherein $R^4$ represents hydrogen.

4. A compound according to claim 1, wherein $R^1$ represents a group selected from the group consisting of

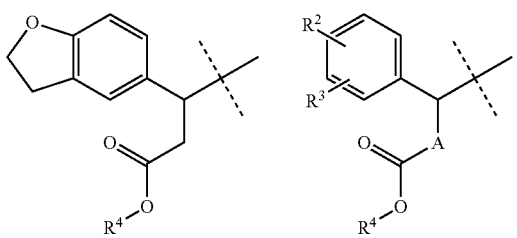

wherein A represents $CH_2$;
$R_2$ represents Cl, Me or —$CF_3$;
$R_3$ represents hydrogen, Cl or F; and
$R_4$ represents hydrogen.

5. A compound according to claim 1, wherein $R^1$ represents a group

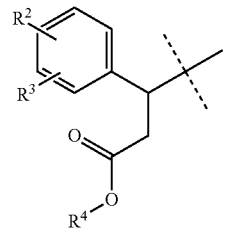

wherein $R_2$ represents Cl;
$R_3$ represents hydrogen, Cl or F; and
$R_4$ represents hydrogen.

6. A compound according to claim 1, wherein X represents an O atom.

7. A compound according to claim 1, wherein Y represents halogen or a —$CH_3$, —$C_2H_5$ or —$OCH_3$ group.

8. A compound according to claim 7, wherein Y represents Cl, F or a —$CH_3$, —$C_2H_5$ or —$OCH_3$ group.

9. A compound according to claim 1, wherein Z represents a $(CH_2)_2$, $CH_2N(CH_3)$ or $CH=N(CH_3)$ group.

10. A compound according to claim 9, wherein Z represents a $(CH_2)_2$ group.

11. A compound according to claim 1, wherein
R represents hydrogen or a —$C_{1-4}$ alkyl, —$C_{3-6}$ cycloalkyl or fluorophenyl group; and
R' represents hydrogen.

12. A compound according to claim 1, wherein
R represents hydrogen or a —$C_{1-4}$ alkyl, —$C_{3-6}$ cycloalkyl or fluorophenyl group;
R' represents hydrogen; and
$R^1$ represents a group selected from the group consisting of

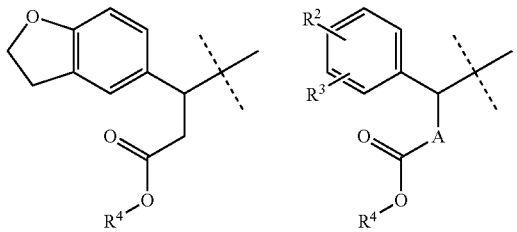

wherein A represents a $CH_2$ group;
$R_2$ represents Cl, Me or —$CF_3$;
$R_3$ represents hydrogen, Cl or F;
$R_4$ represents hydrogen;
X represents O, S or $CH_2$;
Y halogen or a —$CH_3$, —$C_2H_5$ or —$OCH_3$ group; and
Z represents a $(CH_2)_2$, $CH_2N(CH)_3$ or $CH=CH—N(CH_3)$ group.

13. A compound according to claim 1 selected from the group consisting of
3-(2,3-Dihydro-benzofuran-5-yl)-3-({4[2-(2,5-dioxo-pyrrolidin-1-yl)-ethoxy]-3-methoxy-benzyl}-isobutyl-amino)-propionic acid;
3-(4-Chloro-phenyl)-3-({4[2-(2,5-dioxo-pyrrolidin-1-yl)-ethoxy]-3-methoxy-benzyl}-isobutyl-amino)-propionic acid;
3-(Cyclopentylmethyl-{4-[2-(2,5-dioxo-pyrrolidin-1-yl)-ethoxy]-3-methoxy-benzyl}-amino)-3-(2,4-dichloro-phenyl)-propionic acid;

3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid;

(S)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid;

(R)-3-(4-Chloro-phenyl)-3-(isobutyl-{3-methoxy-4-[2-(3-methyl-2,6-dioxo-3,6-dihydro-2H-pyrimidin-1-yl)-ethoxy]-benzyl}-amino)-propionic acid;

3-(4-Chloro-phenyl)-3-(cyclobutyl-{3-methyl-4-[2-(3-methyl-2,6-dioxo-3,6-dihydro-2H-pyrimidin-1-yl-ethoxy]-benzyl}-amino)-propionic acid;

1-[(4-Chloro-phenyl)-({4-[2-(2,5-dioxo-pyrrolidin-1-yl)-ethoxy]-3-methyl-benzyl}-propyl-amino)-methyl]-cyclopropanecarboxylic acid;

(S)-3-(4-Chloro-phenyl)-3-({4-[2-(2,5-dioxo-pyrrolidin-1-yl) -ethoxy]-3-methyl-benzyl}-propyl-amino)-propionic acid;

(R)-3-(4-Chloro-phenyl)-3-({4-[2-(2,5-dioxo-pyrrolidin-1-yl)-ethoxy]-3-methyl-benzyl}-propyl-amino)-propionic acid;

(S)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid;

(R)-3-(4-Chloro-3-fluoro-phenyl)-3-(cyclopropylmethyl-{4-[2-(2,5-dioxo-pyrrolidin-1-yl)-ethoxy]-3-methoxy-benzyl}-amino)-propionic acid;

(S)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid;

(R)-3-(Cyclopropylmethyl-{4-[2-(2,5-dioxo-pyrrolidin-1-yl)-ethoxy]-3-fluoro-benzyl}-amino)-3-(3,4-dichloro-phenyl)-propionic acid;

(S)-3-({3-Chloro-4-[2-(2,5-dioxo-pyrrolidin-1-yl)-ethoxy]-benzyl}-cyclopropyl-ethyl-amino)-3-(4-chloro-3-fluoro-phenyl)-propionic acid;

(R)-3-({3-Chloro-4-[2-(2,5-dioxo-pyrrolidin-1-yl)-ethoxy]-benzyl}-cyclopropyl-ethyl-amino)-3-(4-chloro-3-fluoro-phenyl)-propionic acid;

(S)-3-(4-Chloro-3-fluoro-phenyl)-3-(cyclopentylmethyl-{4-[2(2,5-dioxo-pyrrolidin-1-yl)-ethoxy]-3-methoxy-benzyl}-amino)-propionic acid;

(R)-3-(4-Chloro-3-fluoro-phenyl)-3-(cyclopentylmethyl-{4-[2-(2,5-dioxo-pyrrolidin-1-yl)-ethoxy]-3-methoxy-benzyl}-amino)-propionic acid;

(S)-3-(4-Chloro-3-fluoro-phenyl)-3-(cyclopropylmethyl-{4-[2-(2,5-dioxo-pyrrolidin-1-yl)-ethoxy]-3-fluoro-benzyl}-amino)-propionic acid;

(R)-3-(4-Chloro-3-fluoro-phenyl)-3-(cyclopropylmethyl-{4-[2-(2,5-dioxo-pyrrolidin-1-yl)-ethoxy]-3-fluoro-benzyl}-amino)-propionic acid;

(S)-3-(4-Chloro-3-fluoro-phenyl)-3-({4-[2-(2,5-dioxo-pyrrolidin-1-yl-ethoxy]-3-fluoro-benzyl}-isobutyl-amino)-propionic acid;

(R)-3-(4-Chloro-3-fluoro-phenyl)-3-({4-[2-(2,5-dioxo-pyrrolidin-1-yl)-ethoxy]-3-fluoro-benzyl}-isobutyl-amino)-propionic acid;

(S)-3-(4-Chloro-phenyl)-3-(cyclopropylmethyl-{4-[2-(2,5-dioxo-pyrrolidin-1-yl)-ethoxy]-3-methyl-benzyl}-amino)-propionic acid;

(S)-3-(4-Chloro-3-fluoro-phenyl)-3-({4-[2-(2,5-dioxo-pyrrolidin-1-yl)-ethoxy]-3-methyl-benzyl}-isobutyl-amino)-propionic acid;

(R)-3-(4-Chloro-3-fluoro-phenyl)-3-({4-[2-(2,5-dioxo-pyrrolidin-1-yl)-ethoxy]-3-methyl-benzyl}-isobutyl-amino)-propionic acid;

(S)-3-(Cyclopropylmethyl-{4-[2-(2,5-dioxo-pyrrolidin-1-yl)-ethoxy]-3-methyl-benzyl}-amino)-3-(3,4-dichloro-phenyl)-propionic acid;

(R)-3-(Cyclopropylmethyl-{4-[2-(2,5-dioxo-pyrrolidin-1-yl)-ethoxy]-3-methyl-benzyl}-amino)-3-(3,4-dichloro-phenyl)-propionic acid;

(S)-3-(4-Chloro-phenyl)-3-(cyclopentylmethyl-{4-[2-(2,5-dioxo-pyrrolidin-1-yl)-ethoxy]-3-ethyl-benzyl}-amino)-propionic acid;

(R)-3-(4-Chloro-phenyl)-3-(cyclopentylmethyl-{4-[2-(2,5-dioxo-pyrrolidin-1-yl)-ethoxy]-3-ethyl-benzyl}-amino)-propionic acid;

(S)-3-(4-Chloro-phenyl)-3-(cyclohexylmethyl-{3-methyl-4-[2-(3-methyl-2,5-dioxo-imidazolidin-1-yl)-ethoxy]-benzyl}-amino)-propionic acid;

(R)-3-(4-Chloro-phenyl)-3-(cyclohexylmethyl-{3-methyl-4-[2-(3-methyl-2,5-dioxo-imidazolidin-1-yl)-ethoxy]-benzyl}-amino)-propionic acid;

(S)-3-(4-Chloro-3-fluoro-phenyl)-3-(cyclopentylmethyl-{3-methyl-4-[2-(3-methyl-2,5-dioxo-imidazolidin-1-yl)-ethoxy]-benzyl}-amino)-propionic acid;

(R)-3-(4-Chloro-3-fluoro-phenyl)-3-(cyclopentylmethyl-{3-methyl-4-[2-(3-methyl-2,5-dioxo-imidazolidin-1-yl)-ethoxy]-benzyl}-amino)-propionic acid;

(S)-3-(4-Chloro-3-fluoro-phenyl)-3-(cyclohexylmethyl-{3-methyl-4-[2-(3-methyl-2,5-dioxo-imidazolidin-1-yl)-ethoxy]-benzyl}-amino)-propionic acid;

(R)-3-(4-Chloro-3-fluoro-phenyl)-3-(cyclohexylmethyl-{3-methyl-4-[2-(3-methyl-2,5-dioxo-imidazolidin-1-yl)-ethoxy]-benzyl}-amino)-propionic acid;

3-(4-Chloro-phenyl)-3-(cyclopropylmethyl-{4-[2-(2,5-dioxo-pyrrolidin-1-yl)-ethoxy]-3-methoxy-benzyl}-amino)-propionic acid;

3-(4-Chloro-phenyl)-3-({4-[2-(2,5-dioxo-pyrrolidin-1-yl)-ethoxy]-3-methoxy-benzyl}-propyl-amino)-propionic acid;

3-(Butyl-{4-[2-(2,5-dioxo-pyrrolidin-1-yl)-ethoxy]-3-methoxy-benzyl}-amino)-3-(4-chloro-phenyl)-propionic acid;

3-(4-Chloro-phenyl)-3-(cyclopentylmethyl-{4-[2-(2,5-dioxo-pyrrolidin-1-yl)-ethoxy]-3-methoxy-benzyl}-amino)-propionic acid;

3-(4-Chloro-phenyl)-3-(cyclohexylmethyl-{4-[2-(2,5-dioxo-pyrrolidin-1-yl)-ethoxy]-3-methoxy-benzyl}-amino)-propionic acid;

3-(4-Chloro-3-fluoro-phenyl)-3-({4-[2-(2,5-dioxo-pyrrolidin-1-yl)-ethoxy]-3-methoxy-benzyl}-propyl-amino)-propionic acid;

3-(4-Chloro-3-fluoro-phenyl)-3-({4-[2-(2,5-dioxo-pyrrolidin-1-yl)-ethoxy]-3-methoxy-benzyl}-isobutyl-amino)-propionic acid;

3-(Butyl-{4-[2-(2,5-dioxo-pyrrolidin-1-yl)-ethoxy]-3-methoxy-benzyl}-amino)-3-(4-chloro-3-fluoro-phenyl)-propionic acid;

3-(4-Chloro-3-fluoro-phenyl)-3-(cyclohexylmethyl-{4-[2-(2,5-dioxo-pyrrolidin-1-yl)-ethoxy]-3-methoxy-benzyl}-amino)-propionic acid;

3-(Cyclopropylmethyl-{4-[2-(2,5-dioxo-pyrrolidin-1-yl)-ethoxy]-3-methoxy-benzyl}-amino)-3-(3,4-dichloro-phenyl)-propionic acid;

3-(3,4-Dichloro-phenyl)-3-({4-[2-(2,5-dioxo-pyrrolidin-1-yl)-ethoxy]-3-methoxy-benzyl}-propyl-amino)-propionic acid;

3-(3,4-Dichloro-phenyl)-3-({4-[2-(2,5-dioxo-pyrrolidin-1-yl)-ethoxy]-3-methoxy-benzyl}-isobutyl-amino)-propionic acid;

3-(Butyl-{4-[2-(2,5-dioxo-pyrrolidin-1-yl)-ethoxy]-3-methoxy-benzyl}-amino)-3-(3,4-dichloro-phenyl)-propionic acid;
3-(Cyclopentylmethyl-{4-[2-(2,5-dioxo-pyrrolidin-1-yl)-ethoxy]-3-methoxy-benzyl}-amino)-3-(3,4-dichloro-phenyl)-propionic acid;
3-(Cyclohexylmethyl-{4-[2-(2,5-dioxo-pyrrolidin-1-yl)-ethoxy]-3-methoxy-benzyl}-amino)-3-(3,4-dichloro-phenyl)-propionic acid;
3-(4-Chloro-phenyl)-3-(cyclopropylmethyl-{4-[2-(2,5-dioxo-pyrrolidin-1-yl)-ethoxy]-3-fluoro-benzyl}-amino)-propionic acid;
(R)-3-(4-Chloro-phenyl)-3-({4-[2-(2,5-dioxo-pyrrolidin-1-yl)-ethoxy]-3-fluoro-benzyl}-propyl-amino)-propionic acid;
3-(4-Chloro-phenyl)-3-({4-[2-(2,5-dioxo-pyrrolidin-1-yl)-ethoxy]-3-fluoro-benzyl}-isobutyl-amino)-propionic acid;
3-(Butyl-{4-[2-(2,5-dioxo-pyrrolidin-1-yl)-ethoxy]-3-fluoro-benzyl}-amino)-3-(4-chloro-phenyl)-propionic acid;
(R)-3-(4-Chloro-phenyl)-3-(cyclobutylmethyl-{4-[2-(2,5-dioxo-pyrrolidin-1-yl)-ethoxy]-3-fluoro-benzyl}-amino)-propionic acid;
3-(4-Chloro-phenyl)-3-(cyclopentylmethyl-{4-[2-(2,5-dioxo-pyrrolidin-1-yl)-ethoxy]-3-fluoro-benzyl}-amino)-propionic acid;
3-(4-Chloro-phenyl)-3-(cyclohexylmethyl-{4-[2-(2,5-dioxo-pyrrolidin-1-yl)-ethoxy]-3-fluoro-benzyl}-amino)-propionic acid;
3-(4-Chloro-3-fluoro-phenyl)-3-({4-[2-(2,5-dioxo-pyrrolidin-1-yl)-ethoxy]-3-fluoro-benzyl}-propyl-amino)-propionic acid;
3-(Butyl-{4-[2-(2,5-dioxo-pyrrolidin-1-yl)-ethoxy]-3-fluoro-benzyl}-amino)-3-(4-chloro-3-fluoro-phenyl)-propionic acid;
3-(4-Chloro-3-fluoro-phenyl)-3-(cyclopentylmethyl-{4-[2-(2,5-dioxo-pyrrolidin-1-yl)-ethoxy]-3-fluoro-benzyl}-amino)-propionic acid;
3-(4-Chloro-3-fluoro-phenyl)-3-(cyclohexylmethyl-{4-[2-(2,5-dioxo-pyrrolidin-1-yl)-ethoxy]-3-fluoro-benzyl}-amino)-propionic acid;
3-(3,4-Dichloro-phenyl)-3-({4-[2-(2,5-dioxo-pyrrolidin-1-yl)-ethoxy]-3-fluoro-benzyl}-propyl-amino)-propionic acid;
3-(3,4-Dichloro-phenyl)-3-({4-[2-(2,5-dioxo-pyrrolidin-1-yl)-ethoxy]-3-fluoro-benzyl}-isobutyl-amino)-propionic acid;
3-(Butyl-{4-[2-(2,5-dioxo-pyrrolidin-1-yl)-ethoxy]-3-fluoro-benzyl}-amino)-3-(3,4-dichloro-phenyl)-propionic acid;
3-(Cyclopentylmethyl-{4-[2-(2,5-dioxo-pyrrolidin-1-yl)-ethoxy]-3-fluoro-benzyl}-amino)-3-(3,4-dichloro-phenyl)-propionic acid;
3-(Cyclohexylmethyl-{4-[2-(2,5-dioxo-pyrrolidin-1-yl)-ethoxy]-3-fluoro-benzyl}-amino)-3-(3,4-dichloro-phenyl)-propionic acid;
3-(4-Chloro-phenyl)-3-({4-[2-(2,5-dioxo-pyrrolidin-1-yl)-ethoxy]-3-methyl-benzyl}-ethyl-amino)-propionic acid;
3-(4-Chloro-phenyl)-3-(cyclobutyl-{4-[2-(2,5-dioxo-pyrrolidin-1-yl)-ethoxy]-3-methyl-benzyl}-amino)-propionic acid;
3-(4-Chloro-phenyl)-3-({4-[2-(2,5-dioxo-pyrrolidin-1-yl)-ethoxy]-3-methyl-benzyl}-isobutyl-amino)-propionic acid;
3-(Butyl-{4-[2-(2,5-dioxo-pyrrolidin-1-yl)-ethoxy]-3-methyl-benzyl}-amino)-3-(4-chloro-phenyl)-propionic acid;
(S)-3-(4-Chloro-phenyl)-3-(cyclobutylmethyl-{4-[2-(2,5-dioxo-pyrrolidin-1-yl)-ethoxy]-3-methyl-benzyl}-amino)-propionic acid;
3-(4-Chloro-phenyl)-3-(cyclopentylmethyl-{4-[2-(2,5-dioxo-pyrrolidin-1-yl)-ethoxy]-3-methyl-benzyl}-amino)-propionic acid;
3-(4-Chloro-phenyl)-3-(cyclohexylmethyl-{4-[2-(2,5-dioxo-pyrrolidin-1-yl)-ethoxy]-3-methyl-benzyl}-amino)-propionic acid;
3-(4-Chloro-3-fluoro-phenyl)-3-(cyclopropylmethyl-{4-[2-(2,5-dioxo-pyrrolidin-1-yl)-ethoxy]-3-methyl-benzyl}-amino)-propionic acid;
3-(4-Chloro-3-fluoro-phenyl)-3-({4-[2-(2,5-dioxo-pyrrolidin-1-yl)-ethoxy]-3-methyl-benzyl}-propyl-amino)-propionic acid;
3-(Butyl-{4-[2-(2,5-dioxo-pyrrolidin-1-yl)-ethoxy]-3-methyl-benzyl}-amino)-3-(4-chloro-3-fluoro-phenyl)-propionic acid;
3-(4-Chloro-3-fluoro-phenyl)-3-(cyclopentylmethyl-{4-[2-(2,5-dioxo-pyrrolidin-1-yl)-ethoxy]-3-methyl-benzyl}-amino)-propionic acid;
3-(4-Chloro-3-fluoro-phenyl)-3-(cyclohexylmethyl-{4-[2-(2,5-dioxo-pyrrolidin-1-yl)-ethoxy]-3-methyl-benzyl}-amino)-propionic acid;
3-(3,4-Dichloro-phenyl)-3-({4-[2-(2,5-dioxo-pyrrolidin-1-yl)-ethoxy]-3-methyl-benzyl}-propyl-amino)-propionic acid;
3-(3,4-Dichloro-phenyl)-3-({4-[2-(2,5-dioxo-pyrrolidin-1-yl)-ethoxy]-3-methyl-benzyl}-isobutyl-amino)-propionic acid;
3-(Butyl-{4-[2-(2,5-dioxo-pyrrolidin-1-yl)-ethoxy]-3-methyl-benzyl}-amino)-3-(3,4-dichloro-phenyl)-propionic acid;
3-(Cyclopentylmethyl-{4-[2-(2,5-dioxo-pyrrolidin-1-yl)-ethoxy]-3-methyl-benzyl}-amino)-3-(3,4-dichloro-phenyl)-propionic acid;
3-(Cyclohexylmethyl-{4-[2-(2,5-dioxo-pyrrolidin-1-yl)-ethoxy]-3-methyl-benzyl}-amino)-3-(3,4-dichloro-phenyl)-propionic acid;
3-(4-Chloro-phenyl)-3-(cyclopropylmethyl-{4-[2-(2,5-dioxo-pyrrolidin-1-yl)-ethoxy]-3-ethyl-benzyl}-amino)-propionic acid;
3-(4-Chloro-phenyl)-3-({4-[2-(2,5-dioxo-pyrrolidin-1-yl)-ethoxy]-3-ethyl-benzyl}-propyl-amino)-propionic acid;
3-(4-Chloro-phenyl)-3-({4-[2-(2,5-dioxo-pyrrolidin-1-yl)-ethoxy]-3-ethyl-benzyl}-isobutyl-amino)-propionic acid;
3-(Butyl-{4-[2-(2,5-dioxo-pyrrolidin-1-yl)-ethoxy]-3-ethyl-benzyl}-amino)-3-(4-chloro-phenyl)-propionic acid;
(S)-3-(4-Chloro-phenyl)-3-(cyclobutylmethyl-{4-[2-(2,5-dioxo-pyrrolidin-1-yl)-ethoxy]-3-ethyl-benzyl}-amino)-propionic acid;
3-(4-Chloro-phenyl)-3-(cyclohexylmethyl-{4-[2-(2,5-dioxo-pyrrolidin-1-yl)-ethoxy]-3-ethyl-benzyl}-amino)-propionic acid;
3-(4-Chloro-3-fluoro-phenyl)-3-(cyclopropylmethyl-{4-[2-(2,5-dioxo-pyrrolidin-1-yl)-ethoxy]-3-ethyl-benzyl}-amino)-propionic acid;
3-(4-Chloro-3-fluoro-phenyl)-3-({4-[2-(2,5-dioxo-pyrrolidin-1-yl)-ethoxy]-3-ethyl-benzyl}-propyl-amino)-propionic acid;

3-(4-Chloro-3-fluoro-phenyl)-3-({4-[2-(2,5-dioxo-pyrrolidin-1-yl)-ethoxy]-3-ethyl-benzyl}-isobutyl-amino)-propionic acid;

3-(Butyl-{4-[2-(2,5-dioxo-pyrrolidin-1-yl)-ethoxy]-3-ethyl-benzyl}-amino)-3-(4-chloro-3-fluoro-phenyl)-propionic acid;

3-(4-Chloro-3-fluoro-phenyl)-3-(cyclopentylmethyl-{4-[2-(2,5-dioxo-pyrrolidin-1-yl)-ethoxy]-3-ethyl-benzyl}-amino)-propionic acid;

3-(4-Chloro-3-fluoro-phenyl)-3-(cyclohexylmethyl-{4-[2-(2,5-dioxo-pyrrolidin-1-yl)-ethoxy]-3-ethyl-benzyl}-amino)-propionic acid;

3-(Cyclopropylmethyl-{4-[2-(2,5-dioxo-pyrrolidin-1-yl)-ethoxy]-3-ethyl-benzyl}-amino)-3-(3,4-dichloro-phenyl)-propionic acid;

3-(3,4-Dichloro-phenyl)-3-({4-[2-(2,5-dioxo-pyrrolidin-1-yl)-ethoxy]-3-ethyl-benzyl}-propyl-amino)-propionic acid;

3-(3,4-Dichloro-phenyl)-3-({4-[2-(2,5-dioxo-pyrrolidin-1-yl)-ethoxy]-3-ethyl-benzyl}-isobutyl-amino)-propionic acid;

3-(Butyl-{4-[2-(2,5-dioxo-pyrrolidin-1-yl)-ethoxy]-3-ethyl-benzyl}-amino)-3-(3,4-dichloro-phenyl)-propionic acid;

3-(Cyclopentylmethyl-{4-[2-(2,5-dioxo-pyrrolidin-1-yl)-ethoxy]-3-ethyl-benzyl}-amino)-3-(3,4-dichloro-phenyl)-propionic acid;

3-(Cyclohexylmethyl-{4-[2-(2,5-dioxo-pyrrolidin-1-yl)-ethoxy]-3-ethyl-benzyl}-amino)-3-(3,4-dichloro-phenyl)-propionic acid;

3-({3-Chloro-4-[2-(2,5-dioxo-pyrrolidin-1-yl)-ethoxy]-benzyl}-cyclopropylmethyl-amino)-3-(4-chloro-phenyl)-propionic acid;

3-({3-Chloro-4-[2-(2,5-dioxo-pyrrolidin-1-yl)-ethoxy]-benzyl}-propyl-amino)-3-(4-chloro-phenyl)-propionic acid;

(S)-3-({3-Chloro-4-[2-(2,5-dioxo-pyrrolidin-1-yl)-ethoxy]-benzyl}-cyclobutylmethyl-amino)-3-(4-chloro-phenyl)-propionic acid;

3-({3-Chloro-4-[2-(2,5-dioxo-pyrrolidin-1-yl)-ethoxy]-benzyl}-propyl-amino)-3-(4-chloro-3-fluoro-phenyl)-propionic acid;

3-({3-Chloro-4-[2-(2,5-dioxo-pyrrolidin-1-yl)-ethoxy]-benzyl}-cyclopropylmethyl-amino)-3-(3,4-dichloro-phenyl)-propionic acid;

3-({3-Chloro-4-[2-(2,5-dioxo-pyrrolidin-1-yl)-ethoxy]-benzyl}-propyl-amino)-3-(3,4-dichloro-phenyl)-propionic acid;

(S)-(Cyclopropylmethyl-{4-[2-(2,5-dioxo-pyrrolidin-1-yl)-ethoxy]-3-methoxy-benzyl}-amino)-(3,4-dichloro-phenyl)-acetic acid;

(S)-(3,4-Dichloro-phenyl)-({4-[2-(2,5-dioxo-pyrrolidin-1-yl)-ethoxy]-3-methoxy-benzyl}-propyl-amino)-acetic acid;

(R)-(3,4-Dichloro-phenyl)-({4-[2-(2,5-dioxo-pyrrolidin-1-yl)-ethoxy]-3-methoxy-benzyl}-isobutyl-amino)-acetic acid;

(R)-(Cyclopropylmethyl-{4-[2-(2,5-dioxo-pyrrolidin-1-yl)-ethoxy]-3-methoxy-benzyl}-amino)-(3,4-dichloro-phenyl)-acetic acid;

3-(4-Chloro-phenyl)-3-(ethyl-{3-methyl-4-[2-(3-methyl-2,6-dioxo-3,6-dihydro-2H-pyrimidin-1-yl)-ethoxy]-benzyl}-amino)-propionic acid;

3-(4-Chloro-phenyl)-3-({3-methyl-4-[2-(3-methyl-2,6-dioxo-3,6-dihydro-2H-pyrimidin-1-yl)-ethoxy]-benzyl}-propyl-amino)-propionic acid;

3-(4-Chloro-phenyl)-3-(cyclopropylmethyl-{3-methyl-4-[2-(3-methyl-2,6-dioxo-3,6-dihydro-2H-pyrimidin-1-yl)-ethoxy]-benzyl}-amino)-propionic acid;

3-(4-Chloro-phenyl)-3-(ethyl-{3-methoxy-4-[2-(3-methyl-2,6-dioxo-3,6-dihydro-2H-pyrimidin-1-yl)-ethoxy]-benzyl}-amino)-propionic acid;

3-(4-Chloro-phenyl)-3-(cyclopropylmethyl-{3-methoxy-4-[2-(3-methyl-2,6-dioxo-3,6-dihydro-2H-pyrimidin-1-yl)-ethoxy]-benzyl}-amino)-propionic acid;

3-(4-Chloro-phenyl)-3-({3-methoxy-4-[2-(3-methyl-2,6-dioxo-3,6-dihydro-2H-pyrimidin-1-yl)-ethoxy]-benzyl}-propyl-amino)-propionic acid;

3-(Butyl-{3-methoxy-4-[2-(3-methyl-2,6-dioxo-3,6-dihydro-2H-pyrimidin-1-yl)-ethoxy]-benzyl}-amino)-3-(4-chloro-phenyl)-propionic acid;

3-(4-Chloro-phenyl)-3-(cyclobutyl-{3-methoxy-4-[2-(3-methyl-2,6-dioxo-3,6-dihydro-2H-pyrimidin-1-yl)-ethoxy]-benzyl}-amino)-propionic acid;

3-(Cyclopropylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(2,3-Dihydro-benzofuran-5-yl)-3-(isobutyl-{3-methoxy-4-[2-(3-methyl-2,6-dioxo-3,6-dihydro-2H-pyrimidin-1-yl)-ethoxy]-benzyl}-amino)-propionic acid;

3-(Butyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(2,3-Dihydro-benzofuran-5-yl)-3-({3-methoxy-4-[2-(3-methyl-2,6-dioxo-3,6-dihydro-2H-pyrimidin-1-yl)-ethoxy]-benzyl}-propyl-amino)-propionic acid;

3-(Cyclopropylmethyl-{3-methoxy-4-[2-(3-methyl-2,6-dioxo-3,6-dihydro-2H-pyrimidin-1-yl)-ethoxy]-benzyl}-amino)-3-(3,4-dichloro-phenyl)-propionic acid;

3-(3,4-Dichloro-phenyl)-3-({3-methoxy-4-[2-(3-methyl-2,6-dioxo-3,6-dihydro-2H-pyrimidin-1-yl)-ethoxy]-benzyl}-propyl-amino)-propionic acid;

3-(3,4-Dichloro-phenyl)-3-(ethyl-{3-methoxy-4-[2-(3-methyl-2,6-dioxo-3,6-dihydro-2H-pyrimidin-1-yl)-ethoxy]-benzyl}-amino)-propionic acid;

3-(Cyclopentylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(Cyclohexylmethyl-{3-methoxy-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(4-Chloro-phenyl)-3-[{3-methyl-4-[2-(3-methyl-2,6-dioxo-3,6-dihydro-2H-pyrimidin-1-yl)-ethoxy]-benzyl}-(3,3,3-trifluoro-propyl)-amino]-propionic acid;

3-(4-Chloro-phenyl)-3-[{3-methoxy-4-[2-(3-methyl-2,6-dioxo-3,6-dihydro-2H-pyrimidin-1-yl)-ethoxy]-benzyl}-(3,3,3-trifluoro-propyl)-amino]-propionic acid;

3-(Cyclopropylmethyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(4-Chloro-phenyl)-3-(cyclopropylmethyl-{4-[3-(2,5-dioxo-pyrrolidin-1-yl)-propyl]-3-methoxy-benzyl}-amino)-propionic acid;

3-(4-Chloro-phenyl)-3-({4-[3-(2,5-dioxo-pyrrolidin-1-yl)-propyl]-3-methoxy-benzyl}-propyl-amino)-propionic acid;

3-(4-Chloro-phenyl)-3-({4-[3-(2,5-dioxo-pyrrolidin-1-yl)-propyl]-3-methoxy-benzyl}-isobutyl-amino)-propionic acid;

3-(Butyl-{4-[3-(2,5-dioxo-pyrrolidin-1-yl)-propyl]-3-methoxy-benzyl}-amino)-3-(4-chloro-phenyl)-propionic acid;

3-(4-Chloro-phenyl)-3-(cyclopentylmethyl-{4-[3-(2,5-dioxo-pyrrolidin-1-yl)-propyl]-3-methoxy-benzyl}-amino)-propionic acid;

3-(4-Chloro-phenyl)-3-({4-[3-(2,5-dioxo-pyrrolidin-1-yl)-propyl]-3-methyl-benzyl}-isobutyl-amino)-propionic acid;

3-(4-Chloro-phenyl)-3-(cyclobutyl-{4-[3-(2,5-dioxo-pyrrolidin-1-yl)-propyl]-3-methoxy-benzyl}-amino)-propionic acid;

3-(Cyclopentylmethyl-{4-[3-(2,5-dioxo-pyrrolidin-1-yl)-propyl]-3-methoxy-benzyl}-amino)-3-(2,3-dihydro-benzofuran-5-yl)-propionic acid;

3-(Butyl-{4-[3-(2,5-dioxo-pyrrolidin-1-yl)-propyl]-3-methoxy-benzyl}-amino)-3-(2,3-dihydro-benzofuran-5-yl)-propionic acid;

3-(2,3-Dihydro-benzofuran-5-yl)-3-({4-[3-(2,5-dioxo-pyrrolidin-1-yl)-propyl]-3-methoxy-benzyl}-isobutyl-amino)-propionic acid;

3-(Cyclopropylmethyl-{4-[3-(2,5-dioxo-pyrrolidin-1-yl)-propyl]-3-methyl-benzyl}-amino)-3-(2,3-dihydro-benzofuran-5-yl)-propionic acid;

3-(Cyclohexylmethyl-{4-[3-(2,5-dioxo-pyrrolidin-1-yl)-propyl]-3-methyl-benzyl}-amino)-3-(2,3-dihydro-benzofuran-5-yl)-propionic acid;

3-(2,3-Dihydro-benzofuran-5-yl)-3-({4-[2-(2,5-dioxo-pyrrolidin-1-yl)-ethoxy]-3-methyl-benzyl}-isobutyl-amino)-propionic acid;

3-(Butyl-{4-[2-(2,5-dioxo-pyrrolidin-1-yl)-ethoxy]-3-methyl-benzyl}-amino)-3-(2,3-dihydro-benzofuran-5-yl)-propionic acid;

3-(Cyclopentylmethyl-{4-[2-(2,5-dioxo-pyrrolidin-1-yl)-ethoxy]-3-methoxy-benzyl}-amino)-3-(2,3-dihydro-benzofuran-5-yl)-propionic acid;

3-(Cyclopentylmethyl-{4-[2-(2,5-dioxo-pyrrolidin-1-yl)-ethoxy]-3-methyl-benzyl}-amino)-3-(2,3-dihydro-benzofuran-5-yl)-propionic acid;

3-(Cyclohexylmethyl-{4-[2-(2,5-dioxo-pyrrolidin-1-yl)-ethoxy]-3-methoxy-benzyl}-amino)-3-(2,3-dihydro-benzofuran-5-yl)-propionic acid;

3-(Cyclohexylmethyl-{4-[2-(2,5-dioxo-pyrrolidin-1-yl)-ethoxy]-3-methyl-benzyl}-amino)-3-(2,3-dihydro-benzofuran-5-yl)-propionic acid;

3-(Butyl-{4-[2-(2,5-dioxo-pyrrolidin-1-yl)-ethoxy]-3-methoxy-benzyl}-amino)-3-(2,4-dichloro-phenyl)-propionic acid;

3-(2,4-Dichloro-phenyl)-3-({4-[2-(2,5-dioxo-pyrrolidin-1-yl)-ethoxy]-3-methoxy-benzyl}-isobutyl-amino)-propionic acid;

3-(4-Chloro-phenyl)-3-({3-methoxy-4-[2-(3-methyl-2,6-dioxo-3,6-dihydro-2H-pyrimidin-1-yl)-ethoxy]-benzyl}-methyl-amino)-2-methyl-propionic acid;

3-(4-Chloro-phenyl)-3-(ethyl-{3-methoxy-4-[2-(3-methyl-2,6-dioxo-3,6-dihydro-2H-pyrimidin-1-yl)-ethoxy]-benzyl}-amino)-2-methyl-propionic acid;

3-(2,3-Dihydro-benzofuran-5-yl)-3-(ethyl-{3-methyl-4-[2-(3-methyl-2,6-dioxo-3,6-dihydro-2H-pyrimidin-1-yl)-ethoxy]-benzyl}-amino)-propionic acid;

3-(2,3-Dihydro-benzofuran-5-yl)-3-({3-methyl-4-[2-(3-methyl-2,6-dioxo-3,6-dihydro-2H-pyrimidin-1-yl)-ethoxy]-benzyl}-propyl-amino)-propionic acid;

3-(Cyclopropylmethyl-{3-methoxy-4-[2-(3-methyl-2,6-dioxo-3,6-dihydro-2H-pyrimidin-1-yl)-ethoxy]-benzyl}-amino)-3-(2,4-dichloro-phenyl)-propionic acid;

3-(4-Chloro-phenyl)-3-[{4-[2-(2,5-dioxo-pyrrolidin-1-yl)-ethoxy]-3-methyl-benzyl}-(3,3,3-trifluoro-propyl)-amino]-propionic acid;

3-(2,3-Dihydro-benzofuran-5-yl)-3-(isobutyl-{3-methyl-4-[2-(3-methyl-2,6-dioxo-3,6-dihydro-2H-pyrimidin-1-yl)-ethoxy]-benzyl}-amino)-propionic acid;

3-(2,4-Dichloro-phenyl)-3-({3-methoxy-4-[2-(3-methyl-2,6-dioxo-3,6-dihydro-2H-pyrimidin-1-yl)-ethoxy]-benzyl}-propyl-amino)-propionic acid;

3-(Cyclopentylmethyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(Butyl-{3-methyl-4-[2-(3-methyl-2,6-dioxo-3,6-dihydro-2H-pyrimidin-1-yl)-ethoxy]-benzyl}-amino)-3-(2,3-dihydro-benzofuran-5-yl)-propionic acid;

3-(2,4-Dichloro-phenyl)-3-({4-[2-(2,5-dioxo-pyrrolidin-1-yl)-ethoxy]-3-methyl-benzyl}-isobutyl-amino)-propionic acid;

3-(Cyclopropylmethyl-{4-[2-(2,5-dioxo-pyrrolidin-1-yl)-ethoxy]-3-methyl-benzyl}-amino)-3-(2,4-dichloro-phenyl)-propionic acid;

3-(Butyl-{4-[2-(2,5-dioxo-pyrrolidin-1-yl)-ethoxy]-3-methyl-benzyl}-amino)-3-(2,4-dichloro-phenyl)-propionic acid;

3-(4-Chloro-phenyl)-3-[{4-[2-(2,5-dioxo-pyrrolidin-1-yl)-ethoxy]-3-methoxy-benzyl}-(4-fluoro-benzyl)-amino]-propionic acid;

3-(4-Chloro-phenyl)-3-[{4-[2-(2,5-dioxo-pyrrolidin-1-yl)-ethoxy]-3-methyl-benzyl}-(4-fluoro-benzyl)-amino]-propionic acid;

3-(3,4-Dichloro-phenyl)-3-[{4-[2-(2,5-dioxo-pyrrolidin-1-yl)-ethoxy]-3-methyl-benzyl}-(3,3,3-trifluoro-propyl)-amino]-propionic acid;

1-(Butyl-{4-[2-(2,5-dioxo-pyrrolidin-1-yl)-ethoxy]-3-methoxy-benzyl}-amino)-5-chloro-indan-2-carboxylic acid;

5-Chloro-1-(cyclohexylmethyl-{4-[2-(2,5-dioxo-pyrrolidin-1-yl)-ethoxy]-3-methoxy-benzyl}-amino)-indan-2-carboxylic acid;

5-Chloro-1-({4-[2-(2,5-dioxo-pyrrolidin-1-yl)-ethoxy]-3-methoxy-benzyl}-isobutyl-amino)-indan-2-carboxylic acid;

5-Chloro-1-(cyclopentylmethyl-{4-[2-(2,5-dioxo-pyrrolidin-1-yl)-ethoxy]-3-methoxy-benzyl}-amino)-indan-2-carboxylic acid;

5-Chloro-1-({4-[2-(2,5-dioxo-pyrrolidin-1-yl)-ethoxy]-3-methyl-benzyl}-propyl-amino)-indan-2-carboxylic acid;

1-(Butyl-{4-[2-(2,5-dioxo-pyrrolidin-1-yl)-ethoxy]-3-methyl-benzyl}-amino)-5-chloro-indan-2-carboxylic acid;

5-Chloro-1-({4-[2-(2,5-dioxo-pyrrolidin-1-yl)-ethoxy]-3-methyl-benzyl}-isobutyl-amino)-indan-2-carboxylic acid;

3-(4-Chloro-phenyl)-3-({4-[2-(2,5-dioxo-pyrrolidin-1-yl)-ethoxy]-3-methyl-benzyl}-ethyl-amino)-2-methyl-propionic acid;

3-(4-Chloro-phenyl)-3-({4-[2-(2,5-dioxo-pyrrolidin-1-yl)-ethoxy]-3-methyl-benzyl}-ethyl-amino)-2-methyl-propionic acid;

3-(Butyl-{4-[3-(2,5-dioxo-pyrrolidin-1-yl)-propyl]-3-methyl-benzyl}-amino)-3-(2,3-dihydro-benzofuran-5-yl)-propionic acid;

3-({4-[2-(2,5-Dioxo-pyrrolidin-1-yl)-ethoxy]-3-methyl-benzyl}-propyl-amino)-3-p-tolyl-propionic acid;
3-(Cyclopentylmethyl-{4-[2-(2,5-dioxo-pyrrolidin-1-yl)-ethoxy]-3-methoxy-benzyl}-amino)-3-p-tolyl-propionic acid;
3-(Cyclopentylmethyl-{4-[2-(2,5-dioxo-pyrrolidin-1-yl)-ethoxy]-3-methoxy-benzyl}-amino)-3-(4-trifluoromethyl-phenyl)-propionic acid;
3-(Cyclohexylmethyl-{4-[2-(2,5-dioxo-pyrrolidin-1-yl)-ethoxy]-3-methoxy-benzyl}-amino)-3-(4-trifluoromethyl-phenyl)-propionic acid;
(4-Chloro-phenyl)-({4-[2-(2,5-dioxo-pyrrolidin-1-yl)-ethoxy]-3-methoxy-benzyl}-ethyl-amino)-acetic acid;
(4-Chloro-phenyl)-({4-[2-(2,5-dioxo-pyrrolidin-1-yl)-ethoxy]-3-methoxy-benzyl}-propyl-amino)-acetic acid;
Butyl-{4-[2-(2,5-dioxo-pyrrolidin-1-yl)-ethoxy]-3-methoxy-benzyl}-amino)-(4-chloro-phenyl)-acetic acid;
(4-Chloro-phenyl)-(cyclopentylmethyl-{4-[2-(2,5-dioxo-pyrrolidin-1-yl)-ethoxy]-3-methoxy-benzyl}-amino)-acetic acid;
3-(4-Chloro-phenyl)-3-({4-[2-(2,5-dioxo-pyrrolidin-1-yl)-ethoxy]-3-methoxy-benzyl}-propyl-amino)-2-methyl-propionic acid;
3-(4-Chloro-phenyl)-3-(cyclopropylmethyl-{4-[2-(2,5-dioxo-pyrrolidin-1-yl)-ethoxy]-3-methoxy-benzyl}-amino)-2-methyl-propionic acid;
3-(4-Chloro-phenyl)-3-(cyclopentylmethyl-{4-[2-(2,5-dioxo-pyrrolidin-1-yl)-ethylsulfanyl]-3-methoxy-benzyl}-amino)-propionic acid;
3-(4-Chloro-3-fluoro-phenyl)-3-(cyclopropylmethyl-{4-[2-(2,5-dioxo-pyrrolidin-1-yl)-ethylsulfanyl]-3-methoxy-benzyl}-amino)-propionic acid;
3-(4-Chloro-3-fluoro-phenyl)-3-(cyclopentylmethyl-{4-[2-(2,5-dioxo-pyrrolidin-1-yl)-ethylsulfanyl]-3-methoxy-benzyl}-amino)-propionic acid;
3-(Cyclopropylmethyl-{4-[2-(2,5-dioxo-pyrrolidin-1-yl)-ethylsulfanyl]-3-methoxy-benzyl}-amino)-3-(3,4-dichloro-phenyl)-propionic acid;
3-(3,4-Dichloro-phenyl)-3-({4-[2-(2,5-dioxo-pyrrolidin-1-yl)-ethylsulfanyl]-3-methoxy-benzyl}-propyl-amino)-propionic acid;
3-(3,4-Dichloro-phenyl)-3-({4-[2-(2,5-dioxo-pyrrolidin-1-yl)-ethylsulfanyl]-3-methoxy-benzyl}-isobutyl-amino)-propionic acid;
3-(4-Chloro-phenyl)-3-({4-[2-(2,5-dioxo-pyrrolidin-1-yl)-ethoxy]-3-methyl-benzyl}-propyl-amino)-2-methyl-propionic acid;
3-(4-Chloro-phenyl)-3-({4-[2-(2,5-dioxo-pyrrolidin-1-yl)-ethoxy]-3-fluoro-benzyl}-propyl-amino)-2-methyl-propionic acid;
1-[(4-Chloro-phenyl)-({4-[2-(2,5-dioxo-pyrrolidin-1-yl)-ethoxy]-3-ethyl-benzyl}-propyl-amino)-methyl]-cyclopropanecarboxylic acid;
3-(4-Chloro-phenyl)-3-({4-[2-(2,5-dioxo-pyrrolidin-1-yl)-ethoxy]-3-methoxy-benzyl}-ethyl-amino)-2,2-dimethyl-propionic acid;
(S)-3-(Cyclohexylmethyl-{3-methoxy-4-[2-(3-methyl-2,5-dioxo-imidazolidin-1-yl)-ethoxy]-benzyl}-amino)-3-(3,4-dichloro-phenyl)-propionic acid;
(S)-3-(4-Chloro-phenyl)-3-(cyclopentylmethyl-{3-methyl-4-[2-(3-methyl-2,5-dioxo-imidazolidin-1-yl)-ethoxy]-benzyl}-amino)-propionic acid;
(S)-3-(Cyclopentylmethyl-{3-methyl-4-[2-(3-methyl-2,5-dioxo-imidazolidin-1-yl)-ethoxy]-benzyl}-amino)-3-(3,4-dichloro-phenyl)-propionic acid;
(R)-3-({3-Chloro-4-[2-(3-methyl-2,5-dioxo-imidazolidin-1-yl)-ethoxy]-benzyl}-cyclopentylmethyl-amino)-3-(4-chloro-phenyl)-propionic acid;
(R)-3-({3-Chloro-4-[2-(3-methyl-2,5-dioxo-imidazolidin-1-yl)-ethoxy]-benzyl}-cyclohexylmethyl-amino)-3-(4-chloro-phenyl)-propionic acid;
3-(5-Chloro-thiophen-2-yl)-3-({4-[2-(2,5-dioxo-pyrrolidin-1-yl)-ethoxy]-3-methyl-benzyl}-propyl-amino)-propionic acid; and
3-(2,5-Dimethyl-thiophen-3-yl)-3-({4-[2-(2,5-dioxo-pyrrolidin-1-yl)-ethoxy]-3-methoxy-benzyl}-propyl-amino)-propionic acid, or a pharmaceutically acceptable salt or stereoisomer thereof or a pharmaceutically acceptable salt of the stereoisomer.

14. A process for the preparation of a compound according to claim 1, comprising the steps of reductive amination of a benzaldehyde of formula 4

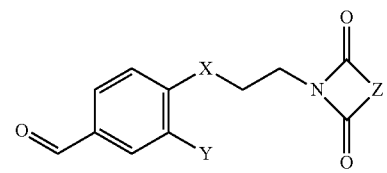

wherein X, Y and Z have the meaning as defined in claim 1—
with a primary amine of formula 5

wherein R¹ has the meaning as defined in claim 1,
reacting the obtained secondary amine of formula 2

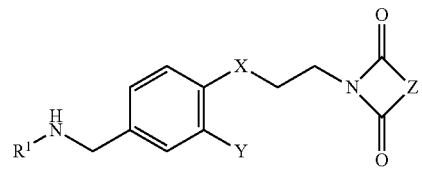

with an aldehyde or cycloalkylketone of formula 3

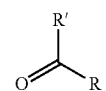

wherein R and R' have the meaning as defined in claim 1,
to obtain an ester of a compound according to claim 1;
and optionally hydrolyzing said ester to obtain a compound according to claim 1.

15. A method for the therapeutic treatment of a disease or disorder selected from the group consisting of COPD, psoriasis, graft/transplant rejection, ophthalmological disease, celiac disease, inflammatory bowel disease (IBD), type 1 diabetes, myasthenia gravis (MG), multiplesclerosis (MS), lupus, rheumatoid arthritis (RA) and lichen planus, the method comprising administering to a patient in need thereof a pharmaceutically effective amount of a compound according to claim 1.

16. A pharmaceutical composition comprising at least one compound according to claim 1 and at least one pharmaceutically acceptable excipient.

17. A compound of formula 2

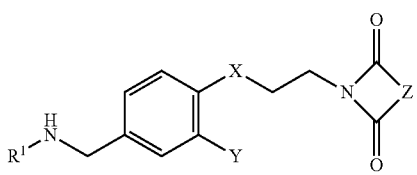

2 wherein

R$^1$ represents a group selected from the group consisting of

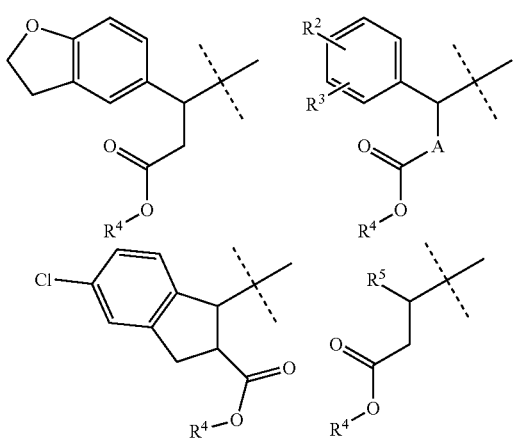

wherein

A represents a direct bond or a CH$_2$, CH(CH$_3$), C(CH$_3$)$_2$ or C(CH$_2$)$_2$ group;

R$_2$ represents Cl, Me or —CF$_3$;

R$_3$ represents hydrogen, Cl or F;

R$_4$ represents hydrogen or a —C$_{1-4}$ alkyl group;

R$_5$ represents a heteroaryl group selected from the group consisting of

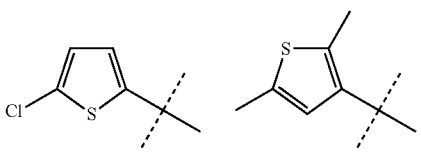

X represents O, S or a CH$_2$ group;

Y represents halogen or a —C$_{1-4}$ alkyl, or —C$_{1-4}$ alkoxy group; and

Z represents a (CH$_2$)$_2$, CH$_2$N(CH$_3$) or CH═CH—N(CH$_3$) group;

or a salt thereof.

* * * * *